US011820996B2

(12) United States Patent
Poirot et al.

(10) Patent No.: US 11,820,996 B2
(45) Date of Patent: *Nov. 21, 2023

(54) METHOD FOR GENERATING T-CELLS COMPATIBLE FOR ALLOGENIC TRANSPLANTATION

(71) Applicant: CELLECTIS, Paris (FR)

(72) Inventors: Laurent Poirot, Paris (FR); David Sourdive, Levallois-Perret (FR); Philippe Duchateau, Dravell (FR); Jean-Pierre Cabaniols, Saint Lau la Foret (FR)

(73) Assignee: CELLECTIS, Paris (FR)

( * ) Notice: Subject to any disclaimer, the term of this patent is extended or adjusted under 35 U.S.C. 154(b) by 1336 days.

This patent is subject to a terminal disclaimer.

(21) Appl. No.: 16/138,908

(22) Filed: Sep. 21, 2018

(65) Prior Publication Data

US 2019/0010514 A1 Jan. 10, 2019

Related U.S. Application Data

(62) Division of application No. 15/123,974, filed as application No. PCT/EP2015/055097 on Mar. 11, 2015, now abandoned.

(30) Foreign Application Priority Data

Mar. 11, 2014 (DK) .............................. PA201470119

(51) Int. Cl.
| | |
|---|---|
| A61K 35/17 | (2015.01) |
| A61K 48/00 | (2006.01) |
| C12N 5/0783 | (2010.01) |
| C12N 5/00 | (2006.01) |
| C07K 14/005 | (2006.01) |
| C07K 14/705 | (2006.01) |
| C07K 14/74 | (2006.01) |
| C07K 16/28 | (2006.01) |
| C12N 9/22 | (2006.01) |
| C12N 15/11 | (2006.01) |
| A61K 39/00 | (2006.01) |
| C12N 15/85 | (2006.01) |
| C12N 15/113 | (2010.01) |
| C12N 15/90 | (2006.01) |

(52) U.S. Cl.
CPC ........ *C12N 15/85* (2013.01); *C07K 14/70503* (2013.01); *C07K 14/70539* (2013.01); *C12N 5/0636* (2013.01); *C12N 15/1138* (2013.01); *C12N 15/907* (2013.01); *C07K 2317/24* (2013.01); *C07K 2317/622* (2013.01)

(58) Field of Classification Search
CPC ........ C07K 14/70503; C07K 14/70539; C07K 2317/24; C07K 2317/622; C07K 14/7051; C07K 14/705; C12N 5/0636; C12N 15/1138; A61K 2039/5158; A61K 39/0011; A61K 35/17

See application file for complete search history.

(56) References Cited

U.S. PATENT DOCUMENTS

| | | |
|---|---|---|
| 9,587,237 B2 | 3/2017 | Hyde et al. |
| 10,370,452 B2 | 8/2019 | Themeli et al. |

(Continued)

FOREIGN PATENT DOCUMENTS

| | | |
|---|---|---|
| WO | 93/02188 A1 | 2/1993 |
| WO | 95/17911 A1 | 12/1994 |

(Continued)

OTHER PUBLICATIONS

Joung et al. Nat Rev Mol Cell Biol, 2013, 14: 49-55 (Year: 2013).*
Cunningham,B.A., Wang,J.L., Berggard,I. and Peterson,P.A. The complete amino acid sequence of beta 2-microglobulin. Biochemistry 1973, 12 (24)4811-4822 (Year: 1973).*
Zijlstra et al. Beta 2 Microglobulin deficient mice lack CD4 -8+ cytolytic T cells, Nature 344:742-746, 1990 (Year: 1990).*
Beurdeley et al. Compact designer TALENs for efficient genome engineering. Nature Communications. 2013. pp 1-8.
Bix et al. Rejection of class I MHC-deficient haemopoietic cells by irridiated MHC-matched mice, Letters to Nature, 1991, vol. 349, pp. 329-331.

(Continued)

*Primary Examiner* — Arthur S Leonard
*Assistant Examiner* — Masudur Rahman
(74) *Attorney, Agent, or Firm* — Arrigo, Lee, Guttman & Mouta-Bellum LLP

(57) ABSTRACT

The present invention pertains to engineered T-cells, method for their preparation and their use as medicament, particularly for immunotherapy. The engineered T-cells of the invention are characterized in that the expression of beta 2-microglobulin (B2M) and/or class II major histocompatibility complex transactivator (CIITA) is inhibited, e.g., by using rare-cutting endonucleases able to selectively inactivating by DNA cleavage the gene encoding B2M and/or CIITA or by using nucleic acid molecules which inhibit the expression of B2M and/or CIITA. In order to further render the T-cell non-alloreactive, at least one gene encoding a component of the T-cell receptor is inactivated, e.g., by using a rare-cutting endonucleases able to selectively inactivating by DNA cleavage the gene encoding said TCR component. In addition, expression of immunosuppressive polypeptide can be performed on those modified T-cells in order to prolong the survival of these modified T cells in host organism. Such modified T-cell is particularly suitable for allogeneic transplantations, especially because it reduces both the risk of rejection by the host's immune system and the risk of developing graft versus host disease. The invention opens the way to standard and affordable adoptive immunotherapy strategies using T-Cells for treating cancer, infections and auto-immune diseases.

14 Claims, 9 Drawing Sheets

Specification includes a Sequence Listing.

(56) References Cited

U.S. PATENT DOCUMENTS

| | | | |
|---|---|---|---|
| 11,186,824 B2* | 11/2021 | Duchateau | A61K 35/17 |
| 2006/0222633 A1 | 10/2006 | Shlomchik et al. | |
| 2007/0036773 A1 | 2/2007 | Cooper et al. | |
| 2014/0349402 A1* | 11/2014 | Cooper | A61K 39/001106 435/325 |
| 2016/0222633 A1 | 8/2016 | Kang | |
| 2018/0141992 A1* | 5/2018 | Cowan | C12N 15/11 |
| 2019/0010514 A1 | 1/2019 | Poirot et al. | |

FOREIGN PATENT DOCUMENTS

| | | | |
|---|---|---|---|
| WO | 95/17911 A1 | 7/1995 | |
| WO | 2005/097160 A2 | 10/2005 | |
| WO | 2008/102274 A2 | 8/2008 | |
| WO | 2009/141729 A2 | 11/2009 | |
| WO | 2012/138927 A2 | 10/2012 | |
| WO | 2012/145384 A1 | 10/2012 | |
| WO | 2013/049459 A2 | 4/2013 | |
| WO | 2013/074916 A1 | 5/2013 | |
| WO | 2013/158292 A1 | 10/2013 | |
| WO | 2013/176915 A1 | 11/2013 | |
| WO | 2014/138315 A1 | 9/2014 | |
| WO | 2014/159435 A1 | 10/2014 | |
| WO | 2014/165707 A2 | 10/2014 | |
| WO | WO2014165707 A2 † | 10/2014 | |
| WO | 2015/136001 A1 | 9/2015 | |

OTHER PUBLICATIONS

Bix and Raulet. Functionally conformed free class I heavy chains exist on the surface of β2 microglobulin negative cells. J Exp Med, vol. 176, 829-834.

Campoli and Ferrone. Tumor escape mechanisms: potential role of soluble HLA antigens and NK cells activating ligands. Tissue Antigens, 2008, 72(4), 321-334.

Carroll Dana. A CRISPR approach to gene targeting. The American Society of Gene and Cell Therapy, 20(9), 1658-1660.

Beurdeley et al. Cellectis bioresearch launches Compact TALEN the next generation of TAL effector nucleases. 2013. Cellectic Bioresearch, pp. 1-2.

Depil et al. 'Off-the-shelf allogeneic CAR T cells: development and challenges. Nature Reviews. vol 19, 2020, pp. 185-199.

Williams et al. Evaluation of engineering strategies allowing efficient adoptive transfer of CAR T-cells in an allogeneic setting, Keystone, 2018, pp. 1-10.

Dammeyer et al. Vaccination with β2-Microglobulin-Deficient dendritic cells protects again growth of B2-Microglobulin-Deficient tumours. Scandinavian Journal of Immunology, vol. 70, pp. 44-52.

Figueiredo et al. MHC Universal cels survuce in an allogeneic environment after incompatible transplantation. BioMed Research International, 2013, pp. 1-13.

Figueiredo et al. Regulating MHC expression for cellular therapeutics. Transplantation and Cellular Engineering. 2007, vol. 47, pp. 18-27.

Gaj et al. ZFN, TALEN and CRISPR/Cas-based methods for genome engineering. Trends in Biotechnology, 2013, 31 (7), pp. 397-405.

Glas et al. Major histocompatibility complex class I-specific and -restricted killing of β2-microglobulin-deficient cells by CD8+ cytotoxic T lymphocytes, Proc Natl Acad Sci, 1992, 89, pp. 11381-11385.

Gonzalez et al. Amplification of RNAi-Trageting HLA mRNAs. Molecular Therapy, 2005, 11(5), pp. 811-818.

Guo et al. Mutant β2M-HLA-E and B2M-HLA-G fusion proteins protects universal chimeric antigen receptor-modified T cells from allogeneic NK cell-mediated lysis, European Journal of Immunology, 2021, 51, 2513-2521.

John et al. Anti-PD-1 antibody therapy potently enhances the eradication of established tumors by gene-modified T cells. Clinical Cancer Research. 2013, 19(20), pp. 5636-5646.

John et al. Blockade of PD-1 immunosuppression boosts CAR T-cell therapy. Oncoimmunology, 2013, pp. 1-3.

Kayoga et al. Genetic ablation of HLA class I, class II, and the T-cell receptor enables allogeneic T cells to be used for adoptive T cell therapy. American Association for Cancer Research Journals. 2021, pp. 926-936.

Karre et al. Pillars Article: Selective rejection of H-2 deficient lymphoma variants suggests alternative immune defence strategy, Nature, 2986, pp. 675-678.

Kim et al. Human cytomegalovirus UL18 utilizes US6 for evading the NK and T-cell responses, PLOS Phatogens, 2008, 4(8), pp. 1-11.

Le et al. CIITA transformation rescues the apoptotic function of MHC class II melanoma cells. Anticancer Research, 2005, 25, 3889-3892.

Liu et al. CRISPR-Cas9-mediated multiplex gene editing in CAR-T cells. Cell Research (2017) 27, pp. 154-157.

Ljunggren and Karre. In search of the 'missing self': MHC molecules and NK cell recognition. Immunology Today, 11(7), 1990, pp. 237-244.

Lloyd et al. Beyond the antigen receptor: editing the genome of T-cells for cancer adoptive cellular therapies. Frontiers in Immunology, 2013, 4, 1-7.

Lu et al. Generating hypoimmunogenic human embryonic stem cells by the disruption of Beta 2-Microglobulin, Stem Cell Rec and Rep, 2013, 9, pp. 806-813.

Mach et al. MHC Class II-Deficient combined immunodefiency: A disease of gene regulation. Immunological Reviews, 1994, 138, pp. 207-221.

Mandal and Viswanathan. Natural killer cells: in health and disease. Hematl Oncol Stem Cell Ther, 2015, 8(2), 47-55.

Masternak et al. CIITA is a transcriptional coactivator that is recruited to MHC class II promoters by multiple synergistic interactions with an enhanceosome complex. Genes and Development. 2000, 14, 1156-1166.

Matsunaga et al. Activation of antigen-specific cytotoxic T lymphocytes by B2-microglobulin or TAP1 gene disruption and the introduction of recipient-matched MHC class I gene in allogeneic embrypnic stem cell-derived dendritic cells. Journal of Immunology, 2008, 181, 6635-6643.

McCreedy et al. Off the shelf T cell therapies for hematologic malignancies. Best Practices and Research in Clinical Hematology, 2018, pp. 1-11.

Meissner et al. Genome editing for human gene therapy. Methods in Enzymology, 546, pp. 273-295.

Oberg et al. Loss and mismatch of MHC class I is sifficient to trigger NK cell-mediated rejection of resting lymphocytes in vivo-role of KARAP/DAP12-dependent and -independent pathways. Eur J Immunol, 204, 34, pp. 1646-1653.

Valton Julien. Evaluation of engineering strategies allowing efficient allogeneic adoptive transfer of CAR T cells in an immunocompetent in vivo model. Keystone Symposia Conference. 2018.

Provasi et al. Editing T cell specificity towards leukemia by zinc finger nucleases and lentiviral gene transfer. Nature Medicine, 2012, 18(5), pp. 807-815.

Ren et al. Multiplex genome editing to generate universal CAR T cells resistant to PD1 inhibition. Clinical Cancer Research, 2016, 23(9), pp. 2255-2266.

Reyburn et al. The class I MHC homologue of human cytomegalovirus inhibits attack by natural killer cells. Nature, 1997, 286, pp. 514-517.

Riolobos et al. HLA Engineering of human pluripotent stem cells, Molecular Therapy, 2013, 21(6), pp. 1232-1241.

Salih et al. Functional expression and release of ligands for the activating immunoreceptor NKG2D in leukemia. Blood, 2003, 102(4), pp. 1389-1396.

Scharenberg et al. Genome engineering with TAL-effector nucleases and alternative modular nuclease technologies. Current Gene Tehrapy, 2013, 13, pp. 291-303.

Soland et al. Modulation of human mesenchymal stem cell immunogenicity through forced expression of human cytomegalovirus US proteins. PLOS One, 2012, 7(5), pp. 1-15.

(56) References Cited

OTHER PUBLICATIONS

Cellectis, TALEN Solutions is a comprehensive package of solutions for all gene editing projects from Cellectic bioresearch, cell engineering expert since 1999. http://www.cellectis-bioresearch.com/talen-solutions.
Themeli et al. Generation of tumor-targeted human T lymphocytes from induced pluripotent stem cells for cancer therapy. Nature Biotechnology 2013, 31(10), pp. 928-933.
Torikai et al. Engineering T cells to target tumor cells. Engineering in Translational Medicine, 2014, vol. 1, pp. 71-101.
Torikai et al. Toward eliminating HLA class I expression to generate universal cells from allogeneic donors, Blood, 2013, 122(8), pp. 1341-1349.
Torikai et al. A foundation for universal T-cell immunotherapy: T cells engineered to express a CD19-specific chimeric-antigen-receptor and eliminate expression fo endogenous TCR. Blood, 2012, 119(24), pp. 5697-5705.
Trichet et al. Complex interplay of activating and inhibitory signals received by Vγ9Vδ2 T cells revealed by target cell δ 32 microglobulin knockdown, Journal of Immunology, 2006, 177, pp. 6129-6136.
Wieczorek and Uharek. Genetically modified T cells for the treatment of malignant disease. Ttransfusion Medicine and Hemotherapy. 2013, 40, pp. 388-402.
Wilkinson et al. Modulation of natural killer cells nby human cytomegalovirus, J Clin VIrol, 2008, 41(3), pp. 206-212.
Zhang et al. Chimeric Antigen Receptor (CAR) Treg: A promising approach to inducing immunological tolerance, Frontiers in Immunology, 9, 1-8.
Ren et al. Multiplex genome editing to generate universal CAR T cells resistant to PD1 inhibition. Clinical Cancer Research, 2017, 23, 2255-2266.
Hirano et al., Blockade of B7-H1 and PD-1 by Monoclonal Antibodies Potentiates Cancer Therapeutic Immunity, Cancer Res (2005); 65(3): 1089-1096.
Guha P. et al. Frontline Science: Functionally impaired geriatric CAR-T cells rescued by increased α5β1 integrin expression, Journal of leukocyte biology, 2017. vol. 102, No. 2, pp. 201-208.
Yee J. K. Off-target effects of engineered nucleases, The FEBS Journal, 2016, vol. 283, No. 17, pp. 3239-3248.
Tsai S. et al. Guide-seq enables genome wide profiling of off-target cleavage by CRISPR-Cas nucleases, Nature biotechnology, 2015, vol. 33, No. 2, pp. 187-197.
Tilova L. R. et al. Molekulárno genetičeskie narušeniâ v patogeneze opuholej sistemy krovi [Molecular genetic abnormalities in the pathogenesis of hematologic malignancies and corresponding changes in cell signaling systems], Kliničeskaâ onkogematologiâ, 2017, vol. 10, No. 2, pp. 235-249.
Maus M. V. et al. T cells expressing chimeric antigen receptors can cause anaphylaxis in humans, Cancer immunology research, 2013, vol. 1, No. 1, pp. 26-31.
Turtle C. J. et al. CD19 CAR-T cells of defined CD4+: CD8+ composition in adult B cell ALL patients, The Journal of clinical investigation, 2016, vol. 126, No. 6, pp. 2123-2138.
Burns W. R. et al. A high molecular weight melanoma-associated antigen-specific chimeric antigen receptor redirects lymphocytes to target human melanomas, Cancer research, 2010, vol. 70, No. 8, pp. 3027-3033.
Richman S. A. et al. High-affinity GD2-specific CAR T cells induce fatal encephalitis in a preclinical neuroblastoma model, Cancer immunology research, 2018, vol. 6, No. 1, pp. 36-46.
Teplyakov A. et al., Antibody modeling assessment II. Structures and models, Proteins: Structure, Function, and Bioinformatics, 2014, vol. 82, No. 8, pp. 1563-1582.
Chen X. et al. Fusion protein linkers: property, design and functionality, Advanced drug delivery reviews, 2013, vol. 65, No. 10, pp. 1357-1369.
Maeda Y. et al. Engineering of functional chimeric protein G-VargulaLuciferase, Analytical biochemistry, 1997, vol. 249, No. 2, pp. 147-152.

Dolezal O. et al. ScFv multimers of the anti-neuraminidase antibody NC10: shortening of the linker in single-chain Fv fragment assembled in VL to VH orientation drives the formation of dimers, trimers, tetramers and higher molecular mass multimers, Protein engineering, 2000, vol. 13, No. 8, pp. 565-574.
Long A. H. et al. 4-1BB costimulation ameliorates T cell exhaustion induced by tonic signaling of chimeric antigen receptors, Nature Medicine, 2015, vol. 21, No. 6, pp. 581-590.
Srivastava S. et al. Engineering CAR-T cells: design concepts, Trends in immunology, 2015, vol. 36, No. 8, pp. 494-502.
Hudecek M. et al. The nonsignaling extracellular spacer domain of chimeric antigen receptors is decisive for in vivo antitumor activity, Cancer immunology research, 2015, vol. 3, No. 2, pp. 125-135.
Hege K. M. et al. Safety, tumor trafficking and immunogenicity of chimeric antigen receptor (CAR)-T cells specific for TAG-72 in colorectal cancer, Journal for immunotherapy of cancer, 2017, vol. 5, No. 1, pp. 1-14.
Guedan S. et al. Enhancing CAR T cell persistence through ICOS and 4-1BB costimulation, JCI insight, 2018, vol. 3, No. 1, pp. 11-13.
Poirot et al., T-Cell Engineering For "off-The-shelf" Adoptive Immunotherapy, Blood; 122(21) :1661 (Abstract).
Poirot al., T-Cell Engineering For "off-The-shelf" Adoptive Immunotherapy, Blood, 2013, 122(21) :1661 (Abstract).
Torika et al., Toward eliminating HLA class I expression to generate universal cells from allogeneic donors, Blood, 2013, 122(8), 1341-1349.
Cellectis. Cellectis bioresearch launches Compact TALEN the next generation of TAL effector nucleases. Cellectis Bioresearch, 2013, pp. 1-2. https://www.cellectis.com/en/press/cellectis-bioresearch-launches-compact-talen-the-next-generation-of-tal-effector-nucleases/.
Williams et al. Evaluation of engineering strategies allowing efficient adoptive transfer of CAR T-cells in an allogeneic setting, Presented at The Keystone Symposia Conference entitled "Emerging Cellular Therapies: T Cells and Beyond," Feb. 11-15, 2018, poster 3020, pp. 1-10.
Dammeyer et al. Vaccination with 32-Microglobulin-Deficient dendritic cells protects again growth of B2-Microglobulin-Deficient tumours. Scandinavian Journal of Immunology, 2009, 70, 44-52.
Figueiredo et al. MHC Universal cells survive in an allogeneic environment after incompatible transplantation. BioMed Research International, 2013, vol. 2013, article 796046, pp. 1-12. doi: 10.1155/2013/796046.
John et al. Blockade of PD-1 immunosuppression boosts CAR T-cell therapy. Oncoimmunology, 2013, 19(20), pp. 1-3.
Kayoga et al. Genetic ablation of HLA class I, class II, and the T-cell receptor enables allogeneic T cells to be used for adoptive T cell therapy. American Association for Cancer Research Journals. 2020, 8, pp. 926-936.
Karre et al. Pillars Article: Selective rejection of H-2 deficient lymphoma variants suggests alternative immune defence strategy, Nature, 1986, vol. 319, pp. 675-678.
McCreedy et al. Off the shelf T cell therapies for hematologic malignancies. Best Practices and Research in Clinical Hematology, 2018, 31(2), pp. 166-175.
Meissner et al. Genome editing for human gene therapy. Methods in Enzymology, 2014, 546, ISSN 0076-6879, pp. 273-295.
Cellectis, TALEN Solutions is a comprehensive package of solutions for all gene editing projects from Cellectic bioresearch, cell engineering expert since 1999. 2013, p. 1-3. http://www.cellectis-bioresearch.com/talen-solutions.
Zhang et al. Chimeric Antigen Receptor (CAR) Treg: A promising approach to inducing immunological tolerance, Frontiers in Immunology, 2018, 9, 2359, 1-8.
Beurdeley et al. Compact designer TALENs for efficient genome engineering. Nature Communications. 2013. 4, 1762 pp. 1-8.
Bix and Raulet. Functionally conformed free class I heavy chains exist on the surface of β2 microglobulin negative cells. J Exp Med, 1992, vol. 176, 829-834.
Carroll Dana. A CRISPR approach to gene targeting. The American Society of Gene and Cell Therapy, 2012, 20(9), 1658-1660.

(56) References Cited

OTHER PUBLICATIONS

Oberg et al. Loss and mismatch of MHC class I is sifficient to trigger NK cell-mediated rejection of resting lymphocytes in vivo-role of KARAP/DAP12-dependent and -independent pathways. Eur J Immunol, 2004, 34, pp. 1646-1653.
Torikai et al. Blood, 2012. 119(24)5697-5705.
Hirani et al. Cancer Res 2005; 65(3)1089.
Carroll, D., Molecular Therapy 2012, 20(9)1658-1660.
Champsaur et al., Immunological Reviews 2010, 235:267-285.
Dammeyer et al, "Vaccination with $\beta$2-Microglobulin-Deficient Dendritic Cells Protects Against Growth of $\beta$2-Microglobulin-Deficient Tumours," Scandinavin Journal of Immunology, Apr. 25, 2009, pp. 44-52, vol. 701 No. 1, Blackwell Science Publ., Oxford, GB.
Gaj et al, ZFN, TALEN, and CRISPR/Cas-based methods for genome Trends in Biotechnology, May 9, 2013, pp. 397-405, vol. 31, No. 7, Elsevier Publications, Cambridge, GB.
Höglund et al., "Recognition of $\beta$2-microglobulin-negative ($\beta$2m$^-$) T-cell blasts by natural killer cells from normal but not from $\beta$2m$^-$ mice: Nonresponsiveness controlled by $\beta$2m$^-$ bone marrow in chimeric mice, Proceedings of the National Academy of Sciences," Nov. 15, 1991, pp. 10332-10336, vol. 88, p. 22.
Holling et al., "Epigenetic silencing of MHC2TA transcription in cancer," Biochemical Pharmacology, Nov. 30, 2006, pp. 1570-1576, vol. 72, No. 11, Elsevier, US.
International Search Report and Written Opinion issued in PCT/EP2015/055097 dated May 15, 2015.
Matsunaga et al., Activation of Antigen-Specific Cytotoxic T Lymphocytes by $\beta$2-Microglobulin or TAPI Gene Disruption and the Introduction of Recipient-Matched MHC Class I Gene in Allogeneic Embryonic Stem Cell-Derived Dendritic Cells, The Journal of Immunology, Oct. 20, 2008, pp. 6635-6643, vol. 181. pp. 9.
Riolobos et al., "HI-A Engineering of Human Pluripotent Stem Cells," Molecular Therapy, Apr. 301, 2013, pp. 1232-1241, vol. 21, No. 6.
Soland et al., "Modulation of Human Mesenchymal Stem Cell Immunogenicity through Forced Expression of Human Cytomegalovirus US Proteins," PLoS One, May 301, 2012, pp. 1-15, vol. 7, No. 5.
Trichet et al., "Complex Interplay of Activating and Inhibitory Signals Received by V Y9Vö2 T Cells Revealed by Target Cell $\beta$2—Microglobulin Knockdowns" The Journal of Immunology, Oct. 18, 2006, pp. 6129-6136, vol. 177, No. 9.
Wieczorek et al., "Genetically Modified T Cells for the Treatment of Malignant Disease," Transfusion Medicine and Hemotherapy, Nov. 29, 2013, pp. 388-402, vol. 40, No. 6.
Torika Blood (2013) "Toward eliminating HLA class I expression to generate universalcells from allogeneic donors"; The Blood Journal; May 24, 2018.
Gonzalez et al. Molecular Therapy, "Amplification of RNAi-Targeting HLA mRNAs," vol. 11, No. 5, May 2005.†

\* cited by examiner
† cited by third party

SEQUENCE LISTING

<160> NUMBER OF SEQ ID NOS: 97

<210> SEQ ID NO 1
<211> LENGTH: 119
<212> TYPE: PRT
<213> ORGANISM: Homo sapiens

<400> SEQUENCE: 1

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 2
<211> LENGTH: 6673
<212> TYPE: DNA
<213> ORGANISM: Homo sapiens

<400> SEQUENCE: 2
aatataagtg gaggcgtcgc gctggcgggc attcctgaag ctgacagcat tcgggccgag    60
atgtctcgct ccgtggcctt agctgtgctc gcgctactct ctctttctgg cctggaggct   120
atccagcgtg agtctctcct accctcccgc tctggtcctt cctctcccgc tctgcaccct   180
ctgtggccct cgctgtgctc tctcgctccg tgacttccct tctccaagtt ctccttggtg   240
gcccgccgtg gggctagtcc agggctggat ctcggggaag cggcggggtg gcctgggagt   300
ggggaagggg gtgcgcaccc gggacgcgcg ctacttgccc ctttcggcgg ggagcagggg   360
agacctttgg cctacggcga cgggagggtc gggacaaagt ttagggcgtc gataagcgtc   420
agagcgccga ggttggggga gggtttctct tccgctcttt cgcggggcct ctggctcccc   480
cagcgcagct ggagtggggg acgggtaggc tcgtcccaaa ggcgcggcgc tgaggtttgt   540
gaacgcgtgg agggcgcttg gggtctgggg gaggcgtcg cccgggtaag cctgtctgct   600
gcggctctgc ttcccttaga ctggagagct gtggacttcg tctaggcgcc cgctaagttc   660
gcatgtccta gcacctctgg gtctatgtgg ggccacaccg tggggaggaa acagcacgcg   720
acgtttgtag aatgcttggc tgtgatacaa agcggtttcg aataattaac ttatttgttc   780
ccatcacatg tcacttttaa aaaattataa gaactacccg ttattgacat cttctgtgt   840
gccaaggact ttatgtgctt tgcgtcattt aattttgaaa acagttatct tccgccatag   900
ataactacta tggttatctt ctgcctctca cagatgaaga aactaaggca ccgagatttt   960
aagaaactta attacacagg ggataaatgg cagcaatcga gattgaagtc aagcctaacc  1020
agggcttttg cggagcgca tgcctttggg ctgtaattcg tgcatttttt tttaagaaaa  1080
acgcctgcct tctgcgtgag attctccaga gcaaactggg cggcatgggc cctgtggtct  1140

```
tttcgtacag agggcttcct ctttggctct ttgcctggtt gtttccaaga tgtactgtgc    1200
ctcttacttt cggttttgaa acatgagggg ggttgggcgt ggtagcttac gcctgtaatc    1260
ccagcactta gggaggccga ggcgggagga tggcttgagg tccgtagttg agaccagcct    1320
ggccaacatg gtgaagcctg gtctctacaa aaataataaa caaaaattag ccgggtgtgg    1380
tggctcgtgc ctgtggtccc agctgctccg gtggctgagg cgggaggatc tcttgagctt    1440
aggcttttga gctatcatgg cgccagtgca ctccagcgtg gcaacagagc gagaccctg    1500 tctctcaaaa aagaaaaaaa aaaaaaaaga aagagaaaag aaaagaaaga aagaagtgaa    1560
ggtttgtcag tcaggggagc tgtaaaaacca ttaataaaga taatccaaga tggttaccaa    1620
gactgttgag gacgccagag atcttgagca ctttctaagt acctggcaat acactaagcg    1680
cgctcacctt ttcctctggc aaaacatgat cgaaagcaga atgttttgat catgagaaaa    1740
ttgcatttaa tttgaataca atttatttac aacataaagg ataatgtata tatcaccacc    1800
attactggta tttgctggtt atgttagatg tcattttaaa aaataacaat ctgatattta    1860
aaaaaaaatc ttattttgaa aatttccaaa gtaatacatg ccatgcatag accatttctg    1920
gaagatacca aagaaacat gtaatgatga ttgcctctga aggtctattt tcctcctctg    1980
acctgtgtgt gggttttgtt tttgttttac tgtgggcata aattaatttt tcagttaagt    2040
tttggaagct taaataactc tccaaaagtc ataaagccag taactggttg agcccaaatt    2100
caaacccagc ctgtctgata cttgtcctct tcttagaaaa gattacagtg atgctctcac    2160
aaaatcttgc cgccttccct caaacagaga gttccaggca ggatgaatct gtgctctgat    2220
ccctgaggca tttaatatgt tcttattatt agaagctcag atgcaaagag ctctcttagc    2280
ttttaatgtt atgaaaaaaa tcaggtcttc attagattcc ccaatccacc tcttgatggg    2340
gctagtagcc tttccttaat gatagggtgt ttctagagag atatatctgg tcaaggtggc    2400
ctggtactcc tccttctccc cacagcctcc cagacaagga ggagtagctg ccttttagtg    2460
atcatgtacc ctgaatataa gtgtatttaa aagaattttta tacacatata tttagtgtca    2520
atctgtatat ttagtagcac taacacttct cttcattttc aatgaaaaat atagagttta    2580 taatatttc ttcccacttc cccatggatg gtctagtcat gcctctcatt ttggaaagta    2640
ctgtttctga acattaggc aatatattcc caacctggct agtttacagc aatcacctgt    2700
ggatgctaat taaaacgcaa atcccactgt cacatgcatt actccatttg atcataatgg    2760
aaagtatgtt ctgtcccatt tgccatagtc ctcacctatc cctgttgtat tttatcgggt    2820
ccaactcaac catttaaggt atttgccagc tcttgtatgc atttaggttt tgtttctttg    2880
ttttttagct catgaaatta ggtacaaagt cagagagggg tctggcatat aaaacctcag    2940
cagaaataaa gaggttttgt tgtttggtaa gaacatacct tgggttggtt gggcacggtg    3000
gctcgtgcct gtaatcccaa cactttggga ggccaaggca ggctgatcac ttgaagttgg    3060
gagttcaaga ccagcctggc caacatggtg aaatcccgtc tctactgaaa atacaaaaat    3120
taaccaggca tggtggtgtg tgcctgtagt cccaggaatc acttgaaccc aggaggcgga    3180
ggttgcagtg agctgagatc tcaccactgc acactgcact ccagcctggg caatggaatg    3240
agattccatc ccaaaaaata aaaaaataaa aaataaaga acataccttg ggttgatcca    3300
cttaggaacc tcagataata acatctgcca cgtatagagc aattgctatg tcccaggcac    3360
tctactagac acttcataca gtttagaaaa tcagatgggt gtagatcaag gcaggagcag    3420
gaaccaaaaa gaaaggcata acataagaa aaaaaatgga agggtggaa acagagtaca    3480
```

```
ataacatgag taatttgatg ggggctatta tgaactgaga aatgaacttt gaaaagtatc    3540
ttggggccaa atcatgtaga ctcttgagtg atgtgttaag gaatgctatg agtgctgaga    3600
gggcatcaga agtccttgag agcctccaga gaaaggctct taaaaatgca gcgcaatctc    3660
cagtgacaga agatactgct agaaatctgc tagaaaaaaa acaaaaaagg catgtataga    3720
ggaattatga gggaaagata ccaagtcacg gtttattctt caaaatggag gtggcttgtt    3780
gggaaggtgg aagctcattt ggccagagtg gaaatggaat tgggagaaat cgatgaccaa    3840
atgtaaacac ttggtgcctg atatagcttg acaccaagtt agccccaagt gaaataccct    3900
ggcaatatta atgtgtcttt tcccgatatt cctcaggtac tccaaagatt caggtttact    3960
cacgtcatcc agcagagaat ggaaagtcaa atttcctgaa ttgctatgtg tctgggtttc    4020
atccatccga cattgaagtt gacttactga agaatggaga gagaattgaa aaagtggagc    4080
attcagactt gtctttcagc aaggactggt ctttctatct cttgtactac actgaattca    4140
cccccactga aaaagatgag tatgcctgcc gtgtgaacca tgtgactttg tcacagccca    4200
agatagttaa gtggggtaag tcttacattc ttttgtaagc tgctgaaagt tgtgtatgag    4260
tagtcatatc ataaagctgc tttgatataa aaaggtcta tggccatact accctgaatg    4320
agtcccatcc catctgatat aaacaatctg catattggga ttgtcaggga atgttcttaa    4380
agatcagatt agtggcacct gctgagatac tgatgcacag catggtttct gaaccagtag    4440
tttccctgca gttgagcagg gagcagcagc agcacttgca caaatacata tacactctta    4500
acacttctta cctactggct tcctctagct tttgtggcag cttcaggtat atttagcact    4560
gaacgaacat ctcaagaagg tataggcctt tgtttgtaag tcctgctgtc ctagcatcct    4620
ataatcctgg acttctccag tactttctgg ctggattggt atctgaggct agtaggaagg    4680
gcttgttcct gctgggtagc tctaaacaat gtattcatgg gtaggaacag cagcctattc    4740
tgccagcctt atttctaacc attttagaca tttgttagta catggtattt taaaagtaaa    4800
acttaatgtc ttcctttttt ttctccactg tcttttttcat agatcgagac atgtaagcag    4860
catcatggag gtaagttttt gaccttgaga aaatgttttt gtttcactgt cctgaggact    4920
atttatagac agctctaaca tgataaccct cactatgtgg agaacattga cagagtaaca    4980
ttttagcagg gaaagaagaa tcctacaggg tcatgttccc ttctcctgtg gagtggcatg    5040
aagaaggtgt atggcccag gtatggccat attactgacc ctctacagag agggcaaagg     5100
aactgccagt atggtattgc aggataaagg caggtggtta cccacattac ctgcaaggct    5160
ttgatctttc ttctgccatt tccacattgg acatctctgc tgaggagaga aaatgaacca    5220
ctctttcct ttgtataatg ttgttttatt cttcagacag aagagaggag ttatacagct     5280
ctgcagacat cccattcctg tatggggact gtgtttgcct cttagaggtt cccaggccac    5340
tagaggagat aaagggaaac agattgttat aacttgatat aatgatacta taatagatgt    5400
aactacaagg agctccagaa gcaagagaga gggaggaact tggacttctc tgcatcttta    5460
gttggagtcc aaaggctttt caatgaaatt ctactgccca gggtacattg atgctgaaac    5520
cccattcaaa tctcctgtta tattctagaa cagggaattg atttgggaga gcatcaggaa    5580
ggtggatgat ctgcccagtc acactgttag taaattgtag agccaggacc tgaactctaa    5640
tatagtcatg tgttacttaa tgacggggac atgttctgag aaatgcttac acaaacctag    5700
gtgttgtagc ctactacacg cataggctac atggtatagc ctattgctcc tagactacaa    5760
acctgtacag cctgttactg tactgaatac tgtgggcagt tgtaacacaa tggtaagtat    5820
ttgtgtatct aaacatagaa gttgcagtaa aaatatgcta ttttaatctt atgagaccac    5880
```

| | |
|---|---:|
| tgtcatatat acagtccatc attgaccaaa acatcatatc agcattttt cttctaagat | 5940 |
| tttgggagca ccaaagggat acactaacag gatatactct ttataatggg tttggagaac | 6000 |
| tgtctgcagc tacttctttt aaaaaggtga tctacacagt agaaattaga caagtttggt | 6060 |
| aatgagatct gcaatccaaa taaaataaat tcattgctaa cctttttctt ttcttttcag | 6120 |
| gtttgaagat gccgcatttg gattggatga attccaaatt ctgcttgctt gcttttaat | 6180 |
| attgatatgc ttatacactt acactttatg cacaaaatgt agggttataa taatgttaac | 6240 |
| atggacatga tcttctttat aattctactt tgagtgctgt ctccatgttt gatgtatctg | 6300 |
| agcaggttgc tccacaggta gctctaggag ggctggcaac ttagaggtgg ggagcagaga | 6360 |
| attctcttat ccaacatcaa catcttggtc agatttgaac tcttcaatct cttgcactca | 6420 |
| aagcttgtta agatagttaa gcgtgcataa gttaacttcc aatttacata ctctgcttag | 6480 |
| aatttggggg aaaatttaga aatataattg acaggattat tggaaatttg ttataatgaa | 6540 |
| tgaaacattt tgtcatataa gattcatatt tacttcttat acatttgata agtaaggca | 6600 |
| tggttgtggt taatctggtt tatttttgtt ccacaagtta ataaatcat aaaacttgat | 6660 |
| gtgttatctc tta | 6673 |

<210> SEQ ID NO 3
<211> LENGTH: 987
<212> TYPE: DNA
<213> ORGANISM: Homo sapiens

<400> SEQUENCE: 3

| | |
|---|---:|
| aatataagtg gaggcgtcgc gctggcgggc attcctgaag ctgacagcat tcgggccgag | 60 |
| atgtctcgct ccgtggcctt agctgtgctc gcgctactct ctctttctgg cctggaggct | 120 |
| atccagcgta ctccaaagat tcaggtttac tcacgtcatc cagcagagaa tggaaagtca | 180 |
| aatttcctga attgctatgt gtctgggttt catccatccg acattgaagt tgacttactg | 240 |
| aagaatggag agagaattga aaaagtggag cattcagact tgtctttcag caaggactgg | 300 |
| tctttctatc tcttgtacta cactgaattc accccccactg aaaaagatga gtatgcctgc | 360 |
| cgtgtgaacc atgtgacttt gtcacagccc aagatagtta gtgggatcg agacatgtaa | 420 |
| gcagcatcat ggaggtttga agatgccgca tttggattgg atgaattcca aattctgctt | 480 |
| gcttgctttt taatattgat atgcttatac acttacactt tatgcacaaa atgtagggtt | 540 |
| ataataatgt taacatggac atgatcttct ttataattct actttgagtg ctgtctccat | 600 |
| gtttgatgta tctgagcagg ttgctccaca ggtagctcta ggagggctgg caacttagag | 660 |
| gtggggagca gagaattctc ttatccaaca tcaacatctt ggtcagattt gaactcttca | 720 |
| atctcttgca ctcaaagctt gttaagatag ttaagcgtgc ataagttaac ttccaattta | 780 |
| catactctgc ttagaatttg ggggaaaatt tagaaatata attgacagga ttattggaaa | 840 |
| tttgttataa tgaatgaaac attttgtcat ataagattca tatttacttc ttatacattt | 900 |
| gataaagtaa ggcatggttg tggttaatct ggtttatttt tgttccacaa gttaaataaa | 960 |
| tcataaaact tgatgtgtta tctctta | 987 |

<210> SEQ ID NO 4
<211> LENGTH: 1130
<212> TYPE: PRT
<213> ORGANISM: Homo sapiens

<400> SEQUENCE: 4

```
Met Arg Cys Leu Ala Pro Arg Pro Ala Gly Ser Tyr Leu Ser Glu Pro
1               5                   10                  15

Gln Gly Ser Ser Gln Cys Ala Thr Met Glu Leu Gly Pro Leu Glu Gly
            20                  25                  30

Gly Tyr Leu Glu Leu Leu Asn Ser Asp Ala Asp Pro Leu Cys Leu Tyr
        35                  40                  45

His Phe Tyr Asp Gln Met Asp Leu Ala Gly Glu Glu Ile Glu Leu
    50                  55                  60

Tyr Ser Glu Pro Asp Thr Asp Thr Ile Asn Cys Asp Gln Phe Ser Arg
65                  70                  75                  80

Leu Leu Cys Asp Met Glu Gly Asp Glu Glu Thr Arg Glu Ala Tyr Ala
                85                  90                  95

Asn Ile Ala Glu Leu Asp Gln Tyr Val Phe Gln Asp Ser Gln Leu Glu
            100                 105                 110

Gly Leu Ser Lys Asp Ile Phe Lys His Ile Gly Pro Asp Glu Val Ile
        115                 120                 125

Gly Glu Ser Met Glu Met Pro Ala Glu Val Gly Gln Lys Ser Gln Lys
    130                 135                 140

Arg Pro Phe Pro Glu Glu Leu Pro Ala Asp Leu Lys His Trp Lys Pro
145                 150                 155                 160

Ala Glu Pro Pro Thr Val Val Thr Gly Ser Leu Leu Val Gly Pro Val
                165                 170                 175

Ser Asp Cys Ser Thr Leu Pro Cys Leu Pro Leu Pro Ala Leu Phe Asn
            180                 185                 190

Gln Glu Pro Ala Ser Gly Gln Met Arg Leu Glu Lys Thr Asp Gln Ile
        195                 200                 205

Pro Met Pro Phe Ser Ser Ser Leu Ser Cys Leu Asn Leu Pro Glu
    210                 215                 220

Gly Pro Ile Gln Phe Val Pro Thr Ile Ser Thr Leu Pro His Gly Leu
225                 230                 235                 240

Trp Gln Ile Ser Glu Ala Gly Thr Gly Val Ser Ser Ile Phe Ile Tyr
                245                 250                 255

His Gly Glu Val Pro Gln Ala Ser Gln Val Pro Pro Ser Gly Phe
            260                 265                 270

Thr Val His Gly Leu Pro Thr Ser Pro Asp Arg Pro Gly Ser Thr Ser
        275                 280                 285

Pro Phe Ala Pro Ser Ala Thr Asp Leu Pro Ser Met Pro Glu Pro Ala
    290                 295                 300

Leu Thr Ser Arg Ala Asn Met Thr Glu His Lys Thr Ser Pro Thr Gln
305                 310                 315                 320

Cys Pro Ala Ala Gly Glu Val Ser Asn Lys Leu Pro Lys Trp Pro Glu
                325                 330                 335

Pro Val Glu Gln Phe Tyr Arg Ser Leu Gln Asp Thr Tyr Gly Ala Glu
            340                 345                 350

Pro Ala Gly Pro Asp Gly Ile Leu Val Glu Val Asp Leu Val Gln Ala
        355                 360                 365

Arg Leu Glu Arg Ser Ser Lys Ser Leu Glu Arg Glu Leu Ala Thr
    370                 375                 380

Pro Asp Trp Ala Glu Arg Gln Leu Ala Gln Gly Gly Leu Ala Glu Val
385                 390                 395                 400

Leu Leu Ala Ala Lys Glu His Arg Arg Pro Arg Glu Thr Arg Val Ile
                405                 410                 415

Ala Val Leu Gly Lys Ala Gly Gln Gly Lys Ser Tyr Trp Ala Gly Ala
```

```
            420                 425                 430
Val Ser Arg Ala Trp Ala Cys Gly Arg Leu Pro Gln Tyr Asp Phe Val
            435                 440                 445

Phe Ser Val Pro Cys His Cys Leu Asn Arg Pro Gly Asp Ala Tyr Gly
450                 455                 460

Leu Gln Asp Leu Leu Phe Ser Leu Gly Pro Gln Pro Leu Val Ala Ala
465                 470                 475                 480

Asp Glu Val Phe Ser His Ile Leu Lys Arg Pro Asp Arg Val Leu Leu
                    485                 490                 495

Ile Leu Asp Gly Phe Glu Glu Leu Ala Gln Asp Gly Phe Leu His
                500                 505                 510

Ser Thr Cys Gly Pro Ala Pro Ala Glu Pro Cys Ser Leu Arg Gly Leu
            515                 520                 525

Leu Ala Gly Leu Phe Gln Lys Lys Leu Leu Arg Gly Cys Thr Leu Leu
            530                 535                 540

Leu Thr Ala Arg Pro Arg Gly Arg Leu Val Gln Ser Leu Ser Lys Ala
545                 550                 555                 560

Asp Ala Leu Phe Glu Leu Ser Gly Phe Ser Met Glu Gln Ala Gln Ala
                    565                 570                 575

Tyr Val Met Arg Tyr Phe Glu Ser Ser Gly Met Thr Glu His Gln Asp
                580                 585                 590

Arg Ala Leu Thr Leu Leu Arg Asp Arg Pro Leu Leu Leu Ser His Ser
            595                 600                 605

His Ser Pro Thr Leu Cys Arg Ala Val Cys Gln Leu Ser Glu Ala Leu
        610                 615                 620

Leu Glu Leu Gly Glu Asp Ala Lys Leu Pro Ser Thr Leu Thr Gly Leu
625                 630                 635                 640

Tyr Val Gly Leu Leu Gly Arg Ala Ala Leu Asp Ser Pro Pro Gly Ala
                    645                 650                 655

Leu Ala Glu Leu Ala Lys Leu Ala Trp Glu Leu Gly Arg Arg His Gln
                660                 665                 670

Ser Thr Leu Gln Glu Asp Gln Phe Pro Ser Ala Asp Val Arg Thr Trp
            675                 680                 685

Ala Met Ala Lys Gly Leu Val Gln His Pro Pro Arg Ala Ala Glu Ser
        690                 695                 700

Glu Leu Ala Phe Pro Ser Phe Leu Leu Gln Cys Phe Leu Gly Ala Leu
705                 710                 715                 720

Trp Leu Ala Leu Ser Gly Glu Ile Lys Asp Lys Glu Leu Pro Gln Tyr
                    725                 730                 735

Leu Ala Leu Thr Pro Arg Lys Lys Arg Pro Tyr Asp Asn Trp Leu Glu
                740                 745                 750

Gly Val Pro Arg Phe Leu Ala Gly Leu Ile Phe Gln Pro Pro Ala Arg
            755                 760                 765

Cys Leu Gly Ala Leu Leu Gly Pro Ser Ala Ala Ser Val Asp Arg
        770                 775                 780

Lys Gln Lys Val Leu Ala Arg Tyr Leu Lys Arg Leu Gln Pro Gly Thr
785                 790                 795                 800

Leu Arg Ala Arg Gln Leu Leu Glu Leu Leu His Cys Ala His Glu Ala
                    805                 810                 815

Glu Glu Ala Gly Ile Trp Gln His Val Val Gln Glu Leu Pro Gly Arg
                820                 825                 830

Leu Ser Phe Leu Gly Thr Arg Leu Thr Pro Pro Asp Ala His Val Leu
            835                 840                 845
```

Gly Lys Ala Leu Glu Ala Ala Gly Gln Asp Phe Ser Leu Asp Leu Arg
850                 855                 860

Ser Thr Gly Ile Cys Pro Ser Gly Leu Gly Ser Leu Val Gly Leu Ser
865                 870                 875                 880

Cys Val Thr Arg Phe Arg Ala Ala Leu Ser Asp Thr Val Ala Leu Trp
            885                 890                 895

Glu Ser Leu Gln Gln His Gly Glu Thr Lys Leu Leu Gln Ala Ala Glu
        900                 905                 910

Glu Lys Phe Thr Ile Glu Pro Phe Lys Ala Lys Ser Leu Lys Asp Val
    915                 920                 925

Glu Asp Leu Gly Lys Leu Val Gln Thr Gln Arg Thr Arg Ser Ser Ser
930                 935                 940

Glu Asp Thr Ala Gly Glu Leu Pro Ala Val Arg Asp Leu Lys Lys Leu
945                 950                 955                 960

Glu Phe Ala Leu Gly Pro Val Ser Gly Pro Gln Ala Phe Pro Lys Leu
            965                 970                 975

Val Arg Ile Leu Thr Ala Phe Ser Ser Leu Gln His Leu Asp Leu Asp
        980                 985                 990

Ala Leu Ser Glu Asn Lys Ile Gly Asp Glu Gly Val Ser Gln Leu Ser
        995                 1000                1005

Ala Thr Phe Pro Gln Leu Lys Ser Leu Glu Thr Leu Asn Leu Ser
    1010                1015                1020

Gln Asn Asn Ile Thr Asp Leu Gly Ala Tyr Lys Leu Ala Glu Ala
    1025                1030                1035

Leu Pro Ser Leu Ala Ala Ser Leu Leu Arg Leu Ser Leu Tyr Asn
    1040                1045                1050

Asn Cys Ile Cys Asp Val Gly Ala Glu Ser Leu Ala Arg Val Leu
    1055                1060                1065

Pro Asp Met Val Ser Leu Arg Val Met Asp Val Gln Tyr Asn Lys
    1070                1075                1080

Phe Thr Ala Ala Gly Ala Gln Gln Leu Ala Ala Ser Leu Arg Arg
    1085                1090                1095

Cys Pro His Val Glu Thr Leu Ala Met Trp Thr Pro Thr Ile Pro
    1100                1105                1110

Phe Ser Val Gln Glu His Leu Gln Gln Gln Asp Ser Arg Ile Ser
    1115                1120                1125

Leu Arg
    1130

<210> SEQ ID NO 5
<211> LENGTH: 4654
<212> TYPE: DNA
<213> ORGANISM: Homo sapiens

<400> SEQUENCE: 5
ggttagtgat gaggctagtg atgaggctgt gtgcttctga gctgggcatc cgaaggcatc    60
cttggggaag ctgagggcac gaggaggggc tgccagactc cgggagctgc tgcctggctg   120
ggattcctac acaatgcgtt gcctggctcc acgccctgct gggtcctacc tgtcagagcc   180
ccaaggcagc tcacagtgtg ccaccatgga gttggggccc tagaaggtg gctacctgga    240 gcttcttaac agcgatgctg acccctgtg cctctaccac ttctatgacc agatggacct    300
ggctggagaa gaagagattg agctctactc agaacccgac acagacacca tcaactgcga   360
ccagttcagc aggctgttgt gtgacatgga aggtgatgaa gagaccaggg aggcttatgc   420

```
caatatcgcg gaactggacc agtatgtctt ccaggactcc cagctggagg gcctgagcaa      480
ggacattttc aagcacatag gaccagatga agtgatcggt gagagtatgg agatgccagc      540
agaagttggg cagaaaagtc agaaaagacc cttcccagag gagcttccgg cagacctgaa      600
gcactggaag ccagctgagc cccccactgt ggtgactgga agtctcctag tgggaccagt      660
gagcgactgc tccaccctgc cctgcctgcc actgcctgcg ctgttcaacc aggagccagc      720
ctccggccag atgcgcctgg agaaaaccga ccagattccc atgcctttct ccagttcctc      780
gttgagctgc ctgaatctcc ctgagggacc catccagttt gtccccacca tctccactct      840
gccccatggg ctctggcaaa tctctgaggc tggaacaggg gtctccagta tattcatcta      900
ccatggtgag gtgccccagg ccagccaagt accccctccc agtggattca ctgtccacgg      960
cctcccaaca tctccagacc ggccaggctc caccagcccc ttcgctccat cagccactga     1020
cctgcccagc atgcctgaac ctgccctgac ctcccgagca acatgacag agcacaagac     1080 gtcccccacc caatgcccgg cagctggaga ggtctccaac aagcttccaa aatggcctga     1140
gccggtggag cagttctacc gctcactgca ggacacgtat ggtgccgagc ccgcaggccc     1200
ggatggcatc ctagtggagg tggatctggt gcaggccagg ctggagagga gcagcagcaa     1260
gagcctggag cgggaactgg ccaccccgga ctgggcagaa cggcagctgg cccaaggagg     1320
cctggctgag gtgctgttgg ctgccaagga gcaccggcgg ccgcgtgaga cacgagtgat     1380
tgctgtgctg ggcaaagctg gtcagggcaa gagctattgg gctggggcag tgagccgggc     1440
ctgggcttgt ggccggcttc cccagtacga ctttgtcttc tctgtcccct gccattgctt     1500
gaaccgtccg ggggatgcct atggcctgca ggatctgctc ttctccctgg gcccacagcc     1560
actcgtggcg gccgatgagg ttttcagcca catcttgaag agacctgacc gcgttctgct     1620
catcctagac ggcttcgagg agctggaagc gcaagatggc ttcctgcaca gcacgtgcgg     1680
accggcaccg gcggagccct gctccctccg ggggctgctg gccggccttt tccagaagaa     1740
gctgctccga ggttgcaccc tcctcctcac agcccggccc cggggccgcc tggtccagag     1800
cctgagcaag gccgacgccc tatttgagct gtccggcttc tccatggagc aggcccaggc     1860
atacgtgatg cgctactttg agagctcagg gatgacagag caccaagaca gagccctgac     1920
gctcctccgg gaccggccac ttcttctcag tcacagccac agccctactt tgtgccgggc     1980
agtgtgccac ctctcagagg ccctgctgga gcttggggag gacgccaagc tgccctccac     2040
gctcacggga ctctatgtcg gcctgctggg ccgtgcagcc ctcgacagcc ccccggggc     2100 cctggcagag ctggccaagc tggcctggga gctgggccgc agacatcaaa gtaccctaca     2160
ggaggaccag ttcccatccg cagacgtgag gacctgggcg atggccaaag cttagtcca      2220 acacccaccg cgggccgcag agtccgagct ggccttcccc agcttcctcc tgcaatgctt     2280
cctgggggcc ctgtggctgg ctctgagtgg cgaaatcaag gacaaggagc tcccgcagta     2340
cctagcattg acccccaagga agaagaggcc ctatgacaac tggctggagg gcgtgccacg     2400
ctttctggct gggctgatct tccagcctcc cgcccgctgc ctgggagccc tactcgggcc     2460
atcggcggct gcctcggtgg acaggaagca gaaggtgctt gcgaggtacc tgaagcggct     2520
gcagccgggg acactgcggg cgcggcagct gctggagctg ctgcactgcg cccacgaggc     2580
cgaggaggct ggaatttggc agcacgtggt acaggagctc cccggccgcc tctcttttct     2640
gggcacccgc ctcacgcctc ctgatgcaca tgtactgggc aaggccttgg aggcggcggg     2700
ccaagacttc tccctggacc tccgcagcac tggcatttgc ccctctggat tggggagcct     2760
```

```
cgtgggactc agctgtgtca cccgtttcag ggctgccttg agcgacacgg tggcgctgtg    2820
ggagtccctg cagcagcatg gggagaccaa gctacttcag gcagcagagg agaagttcac    2880
catcgagcct ttcaaagcca agtccctgaa ggatgtggaa gacctgggaa agcttgtgca    2940
gactcagagg acgagaagtt cctcggaaga cacagctggg gagctccctg ctgttcggga    3000
cctaaagaaa ctggagtttg cgctgggccc tgtctcaggc cccaggcttt ccccaaaact    3060
ggtgcggatc ctcacggcct tttcctccct gcagcatctg gacctggatg cgctgagtga    3120
gaacaagatc ggggacgagg gtgtctcgca gctctcagcc accttccccc agctgaagtc    3180
cttggaaacc ctcaatctgt cccagaacaa catcactgac ctgggtgcct acaaactcgc    3240
cgaggccctg ccttcgctcg ctgcatccct gctcaggcta agcttgtaca ataactgcat    3300
ctgcgacgtg ggagccgaga gcttggctcg tgtgcttccg gacatggtgt ccctccgggt    3360
gatggacgtc cagtacaaca agttcacggc tgccggggcc cagcagctcg ctgccagcct    3420
tcggaggtgt cctcatgtgg agacgctggc gatgtggacg cccaccatcc cattcagtgt    3480
ccaggaacac ctgcaacaac aggattcacg gatcagcctg agatgatccc agctgtgctc    3540
tggacaggca tgttctctga ggacactaac cacgctggac cttgaactgg gtacttgtgg    3600
acacagctct tctccaggct gtatcccatg agcctcagca tcctggcacc cggccctgc    3660
tggttcaggg ttggcccctg cccggctgcg gaatgaacca catcttgctc tgctgacaga    3720
cacaggcccg gctccaggct cctttagcgc ccagttgggt ggatgcctgg tggcagctgc    3780
ggtccaccca ggagccccga ggccttctct gaaggacatt gcggacagcc acggccaggc    3840
cagagggagt gacagaggca gccccattct gcctgcccag gcccctgcca ccctggggag    3900
aaagtacttc tttttttta ttttttagaca gagtctcact gttgcccagg ctggcgtgca    3960
gtggtgcgat ctgggttcac tgcaacctcc gcctcttggg ttcaagcgat tcttctgctt    4020
cagcctcccg agtagctggg actacaggca cccaccatca tgtctggcta atttttcatt    4080
tttagtagag acagggtttt gccatgttgg ccaggctggt ctcaaactct tgacctcagg    4140
tgatccaccc acctcagcct cccaaagtgc tgggattaca agcgtgagcc actgcaccgg    4200
gccacagaga aagtacttct ccaccctgct ctccgaccag acaccttgac agggcacacc    4260
gggcactcag aagacactga tgggcaaccc ccagcctgct aattccccag attgcaacag    4320
gctgggcttc agtggcagct gcttttgtct atgggactca atgcactgac attgttggcc    4380
aaagccaaag ctaggcctgg ccagatgcac cagcccttag cagggaaaca gctaatggga    4440
cactaatggg gcggtgagag gggaacagac tggaagcaca gcttcatttc ctgtgtcttt    4500
tttcactaca ttataaatgt ctctttaatg tcacaggcag gtccagggtt tgagttcata    4560
ccctgttacc attttggggt acccactgct ctggttatct aatatgtaac aagccacccc    4620
aaatcatagt ggcttaaaac aacactcaca ttta                                 4654
```

```
<210> SEQ ID NO 6
<211> LENGTH: 495
<212> TYPE: PRT
<213> ORGANISM: Artificial Sequence
<220> FEATURE:
<223> OTHER INFORMATION: anti-CD19 Cimeric Antigen Receptor

<400> SEQUENCE: 6

Met Glu Thr Asp Thr Leu Leu Leu Trp Val Leu Leu Leu Trp Val Pro
1               5                   10                  15

Gly Ser Thr Gly Glu Val Gln Leu Gln Gln Ser Gly Pro Glu Leu Ile
            20                  25                  30
```

```
Lys Pro Gly Ala Ser Val Lys Met Ser Cys Lys Ala Ser Gly Tyr Thr
             35                  40                  45

Phe Thr Ser Tyr Val Met His Trp Val Lys Gln Lys Pro Gly Gln Gly
 50                      55                  60

Leu Glu Trp Ile Gly Tyr Ile Asn Pro Tyr Asn Asp Gly Thr Lys Tyr
 65                  70                  75                  80

Asn Glu Lys Phe Lys Gly Lys Ala Thr Leu Thr Ser Asp Lys Ser Ser
                 85                  90                  95

Ser Thr Ala Tyr Met Glu Leu Ser Ser Leu Thr Ser Glu Asp Ser Ala
             100                 105                 110

Val Tyr Tyr Cys Ala Arg Gly Thr Tyr Tyr Gly Ser Arg Val Phe
             115                 120                 125

Asp Tyr Trp Gly Gln Gly Thr Thr Leu Thr Val Ser Ser Gly Gly Gly
             130                 135                 140

Gly Ser Gly Gly Gly Ser Gly Gly Gly Ser Asp Ile Val Met
 145                 150                 155                 160

Thr Gln Ala Ala Pro Ser Ile Pro Val Thr Pro Gly Glu Ser Val Ser
                 165                 170                 175

Ile Ser Cys Arg Ser Ser Lys Ser Leu Leu Asn Ser Asn Gly Asn Thr
             180                 185                 190

Tyr Leu Tyr Trp Phe Leu Gln Arg Pro Gly Gln Ser Pro Gln Leu Leu
         195                 200                 205

Ile Tyr Arg Met Ser Asn Leu Ala Ser Gly Val Pro Asp Arg Phe Ser
         210                 215                 220

Gly Ser Gly Ser Gly Thr Ala Phe Thr Leu Arg Ile Ser Arg Val Glu
 225                 230                 235                 240

Ala Glu Asp Val Gly Val Tyr Tyr Cys Met Gln His Leu Glu Tyr Pro
             245                 250                 255

Phe Thr Phe Gly Ala Gly Thr Lys Leu Glu Leu Lys Arg Ser Asp Pro
             260                 265                 270

Thr Thr Thr Pro Ala Pro Arg Pro Pro Thr Pro Ala Pro Thr Ile Ala
         275                 280                 285

Ser Gln Pro Leu Ser Leu Arg Pro Glu Ala Cys Arg Pro Ala Ala Gly
     290                 295                 300

Gly Ala Val His Thr Arg Gly Leu Asp Phe Ala Cys Asp Ile Tyr Ile
 305                 310                 315                 320

Trp Ala Pro Leu Ala Gly Thr Cys Gly Val Leu Leu Leu Ser Leu Val
                 325                 330                 335

Ile Thr Leu Tyr Cys Lys Arg Gly Arg Lys Lys Leu Leu Tyr Ile Phe
             340                 345                 350

Lys Gln Pro Phe Met Arg Pro Val Gln Thr Thr Gln Glu Glu Asp Gly
             355                 360                 365

Cys Ser Cys Arg Phe Pro Glu Glu Glu Gly Gly Cys Glu Leu Arg
 370                 375                 380

Val Lys Phe Ser Arg Ser Ala Asp Ala Pro Ala Tyr Gln Gln Gly Gln
 385                 390                 395                 400

Asn Gln Leu Tyr Asn Glu Leu Asn Leu Gly Arg Arg Glu Glu Tyr Asp
                 405                 410                 415

Val Leu Asp Lys Arg Arg Gly Arg Asp Pro Glu Met Gly Gly Lys Pro
             420                 425                 430

Arg Arg Lys Asn Pro Gln Glu Gly Leu Tyr Asn Glu Leu Gln Lys Asp
             435                 440                 445
```

```
Lys Met Ala Glu Ala Tyr Ser Glu Ile Gly Met Lys Gly Glu Arg Arg
        450                 455                 460

Arg Gly Lys Gly His Asp Gly Leu Tyr Gln Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 7
<211> LENGTH: 17
<212> TYPE: PRT
<213> ORGANISM: Artificial Sequence
<220> FEATURE:
<223> OTHER INFORMATION: ANti-CD19 CAR

<400> SEQUENCE: 7

Ala Ala Ala Ala Ala Ala Ala Ala Ala Ala Ala Ala Ala Ala Ala Ala
1               5                   10                  15

Ala

<210> SEQ ID NO 8
<211> LENGTH: 23
<212> TYPE: DNA
<213> ORGANISM: Homo sapiens

<400> SEQUENCE: 8
gagaatcaaa atcggtgaat agg                                           23

<210> SEQ ID NO 9
<211> LENGTH: 23
<212> TYPE: DNA
<213> ORGANISM: Homo sapiens

<400> SEQUENCE: 9
ttcaaaacct gtcagtgatt ggg                                           23

<210> SEQ ID NO 10
<211> LENGTH: 23
<212> TYPE: DNA
<213> ORGANISM: Homo sapiens

<400> SEQUENCE: 10
tgtgctagac atgaggtcta tgg                                           23

<210> SEQ ID NO 11
<211> LENGTH: 23
<212> TYPE: DNA
<213> ORGANISM: Homo sapiens

<400> SEQUENCE: 11
cgtcatgagc agattaaacc cgg                                           23

<210> SEQ ID NO 12
<211> LENGTH: 23
<212> TYPE: DNA
<213> ORGANISM: Homo sapiens

<400> SEQUENCE: 12
tcagggttct ggatatctgt ggg                                           23

<210> SEQ ID NO 13
<211> LENGTH: 23
<212> TYPE: DNA
<213> ORGANISM: Homo sapiens
```

```
<400> SEQUENCE: 13
gtcagggttc tggatatctg tgg                                            23

<210> SEQ ID NO 14
<211> LENGTH: 23
<212> TYPE: DNA
<213> ORGANISM: Homo sapiens

<400> SEQUENCE: 14
ttcggaaccc aatcactgac agg                                            23

<210> SEQ ID NO 15
<211> LENGTH: 23
<212> TYPE: DNA
<213> ORGANISM: Homo sapiens

<400> SEQUENCE: 15
taaacccggc cactttcagg agg                                            23

<210> SEQ ID NO 16
<211> LENGTH: 23
<212> TYPE: DNA
<213> ORGANISM: Homo sapiens

<400> SEQUENCE: 16
aaagtcagat ttgttgctcc agg                                            23

<210> SEQ ID NO 17
<211> LENGTH: 23
<212> TYPE: DNA
<213> ORGANISM: Homo sapiens

<400> SEQUENCE: 17
aacaaatgtg tcacaaagta agg                                            23

<210> SEQ ID NO 18
<211> LENGTH: 23
<212> TYPE: DNA
<213> ORGANISM: Homo sapiens

<400> SEQUENCE: 18
tggatttaga gtctctcagc tgg                                            23

<210> SEQ ID NO 19
<211> LENGTH: 23
<212> TYPE: DNA
<213> ORGANISM: Homo sapiens

<400> SEQUENCE: 19
taggcagaca gacttgtcac tgg                                            23

<210> SEQ ID NO 20
<211> LENGTH: 23
<212> TYPE: DNA
<213> ORGANISM: Homo sapiens

<400> SEQUENCE: 20
agctggtaca cggcagggtc agg                                            23

<210> SEQ ID NO 21
<211> LENGTH: 23
<212> TYPE: DNA
```

<213> ORGANISM: Homo sapiens

<400> SEQUENCE: 21
gctggtacac ggcagggtca ggg                                              23

<210> SEQ ID NO 22
<211> LENGTH: 23
<212> TYPE: DNA
<213> ORGANISM: Homo sapiens

<400> SEQUENCE: 22
tctctcagct ggtacacggc agg                                              23

<210> SEQ ID NO 23
<211> LENGTH: 23
<212> TYPE: DNA
<213> ORGANISM: Homo sapiens

<400> SEQUENCE: 23
tttcaaaacc tgtcagtgat tgg                                              23

<210> SEQ ID NO 24
<211> LENGTH: 23
<212> TYPE: DNA
<213> ORGANISM: Homo sapiens

<400> SEQUENCE: 24
gattaaaccc ggccactttc agg                                              23

<210> SEQ ID NO 25
<211> LENGTH: 23
<212> TYPE: DNA
<213> ORGANISM: Homo sapiens

<400> SEQUENCE: 25
ctcgaccagc ttgacatcac agg                                              23

<210> SEQ ID NO 26
<211> LENGTH: 23
<212> TYPE: DNA
<213> ORGANISM: Homo sapiens

<400> SEQUENCE: 26
agagtctctc agctggtaca cgg                                              23

<210> SEQ ID NO 27
<211> LENGTH: 23
<212> TYPE: DNA
<213> ORGANISM: Homo sapiens

<400> SEQUENCE: 27
ctctcagctg gtacacggca ggg                                              23

<210> SEQ ID NO 28
<211> LENGTH: 23
<212> TYPE: DNA
<213> ORGANISM: Homo sapiens

<400> SEQUENCE: 28
aagttcctgt gatgtcaagc tgg                                              23

<210> SEQ ID NO 29
<211> LENGTH: 23

```
<212> TYPE: DNA
<213> ORGANISM: Homo sapiens

<400> SEQUENCE: 29
atcctcctcc tgaaagtggc cgg                                              23

<210> SEQ ID NO 30
<211> LENGTH: 23
<212> TYPE: DNA
<213> ORGANISM: Homo sapiens

<400> SEQUENCE: 30
tgctcatgac gctgcggctg tgg                                              23

<210> SEQ ID NO 31
<211> LENGTH: 23
<212> TYPE: DNA
<213> ORGANISM: Homo sapiens

<400> SEQUENCE: 31
acaaaactgt gctagacatg agg                                              23

<210> SEQ ID NO 32
<211> LENGTH: 23
<212> TYPE: DNA
<213> ORGANISM: Homo sapiens

<400> SEQUENCE: 32
atttgtttga gaatcaaaat cgg                                              23

<210> SEQ ID NO 33
<211> LENGTH: 23
<212> TYPE: DNA
<213> ORGANISM: Homo sapiens

<400> SEQUENCE: 33
catcacagga actttctaaa agg                                              23

<210> SEQ ID NO 34
<211> LENGTH: 23
<212> TYPE: DNA
<213> ORGANISM: Homo sapiens

<400> SEQUENCE: 34
gtcgagaaaa gctttgaaac agg                                              23

<210> SEQ ID NO 35
<211> LENGTH: 23
<212> TYPE: DNA
<213> ORGANISM: Homo sapiens

<400> SEQUENCE: 35
ccactttcag gaggaggatt cgg                                              23

<210> SEQ ID NO 36
<211> LENGTH: 23
<212> TYPE: DNA
<213> ORGANISM: Homo sapiens

<400> SEQUENCE: 36
ctgacaggtt ttgaaagttt agg                                              23

<210> SEQ ID NO 37
```

```
<211> LENGTH: 23
<212> TYPE: DNA
<213> ORGANISM: Homo sapiens

<400> SEQUENCE: 37
agctttgaaa caggtaagac agg                                              23

<210> SEQ ID NO 38
<211> LENGTH: 23
<212> TYPE: DNA
<213> ORGANISM: Homo sapiens

<400> SEQUENCE: 38
tggaataatg ctgttgttga agg                                              23

<210> SEQ ID NO 39
<211> LENGTH: 23
<212> TYPE: DNA
<213> ORGANISM: Homo sapiens

<400> SEQUENCE: 39
agagcaacag tgctgtggcc tgg                                              23

<210> SEQ ID NO 40
<211> LENGTH: 23
<212> TYPE: DNA
<213> ORGANISM: Homo sapiens

<400> SEQUENCE: 40
ctgtggtcca gctgaggtga ggg                                              23

<210> SEQ ID NO 41
<211> LENGTH: 23
<212> TYPE: DNA
<213> ORGANISM: Homo sapiens

<400> SEQUENCE: 41
ctgcggctgt ggtccagctg agg                                              23

<210> SEQ ID NO 42
<211> LENGTH: 23
<212> TYPE: DNA
<213> ORGANISM: Homo sapiens

<400> SEQUENCE: 42
tgtggtccag ctgaggtgag ggg                                              23

<210> SEQ ID NO 43
<211> LENGTH: 23
<212> TYPE: DNA
<213> ORGANISM: Homo sapiens

<400> SEQUENCE: 43
cttcttcccc agcccaggta agg                                              23

<210> SEQ ID NO 44
<211> LENGTH: 23
<212> TYPE: DNA
<213> ORGANISM: Homo sapiens

<400> SEQUENCE: 44
acacggcagg gtcagggttc tgg                                              23
```

-continued

```
<210> SEQ ID NO 45
<211> LENGTH: 23
<212> TYPE: DNA
<213> ORGANISM: Homo sapiens

<400> SEQUENCE: 45
cttcaagagc aacagtgctg tgg                                                23

<210> SEQ ID NO 46
<211> LENGTH: 23
<212> TYPE: DNA
<213> ORGANISM: Homo sapiens

<400> SEQUENCE: 46
ctggggaaga aggtgtcttc tgg                                                23

<210> SEQ ID NO 47
<211> LENGTH: 23
<212> TYPE: DNA
<213> ORGANISM: Homo sapiens

<400> SEQUENCE: 47
tcctcctcct gaaagtggcc ggg                                                23

<210> SEQ ID NO 48
<211> LENGTH: 23
<212> TYPE: DNA
<213> ORGANISM: Homo sapiens

<400> SEQUENCE: 48
ttaatctgct catgacgctg cgg                                                23

<210> SEQ ID NO 49
<211> LENGTH: 23
<212> TYPE: DNA
<213> ORGANISM: Homo sapiens

<400> SEQUENCE: 49
acccggccac tttcaggagg agg                                                23

<210> SEQ ID NO 50
<211> LENGTH: 23
<212> TYPE: DNA
<213> ORGANISM: Homo sapiens

<400> SEQUENCE: 50
ttcttcccca gcccaggtaa ggg                                                23

<210> SEQ ID NO 51
<211> LENGTH: 23
<212> TYPE: DNA
<213> ORGANISM: Homo sapiens

<400> SEQUENCE: 51
cttacctggg ctggggaaga agg                                                23

<210> SEQ ID NO 52
<211> LENGTH: 23
<212> TYPE: DNA
<213> ORGANISM: Homo sapiens

<400> SEQUENCE: 52
gacaccttct tccccagccc agg                                                23
```

<210> SEQ ID NO 53
<211> LENGTH: 23
<212> TYPE: DNA
<213> ORGANISM: Homo sapiens

<400> SEQUENCE: 53
gctgtggtcc agctgaggtg agg                                         23

<210> SEQ ID NO 54
<211> LENGTH: 23
<212> TYPE: DNA
<213> ORGANISM: Homo sapiens

<400> SEQUENCE: 54
ccgaatcctc ctcctgaaag tgg                                         23

<210> SEQ ID NO 55
<211> LENGTH: 49
<212> TYPE: DNA
<213> ORGANISM: Homo sapiens

<400> SEQUENCE: 55
ttccctccca ggcagctcac agtgtgccac catggagttg gggcccta              49

<210> SEQ ID NO 56
<211> LENGTH: 49
<212> TYPE: DNA
<213> ORGANISM: Homo sapiens

<400> SEQUENCE: 56
tgcctctacc acttctatga ccagatggac ctggctggag aagaagaga             49

<210> SEQ ID NO 57
<211> LENGTH: 49
<212> TYPE: DNA
<213> ORGANISM: Homo sapiens

<400> SEQUENCE: 57
tcttcatcca agggactttt cctcccagaa cccgacacag acaccatca             49

<210> SEQ ID NO 58
<211> LENGTH: 49
<212> TYPE: DNA
<213> ORGANISM: Homo sapiens

<400> SEQUENCE: 58
tgttgtgtga catggaaggt gatgaagaga ccagggaggc ttatgccaa             49

<210> SEQ ID NO 59
<211> LENGTH: 47
<212> TYPE: DNA
<213> ORGANISM: Homo sapiens

<400> SEQUENCE: 59
ccaaagattc aggtttactc acgtcatcca gcagagaatg gaaagtc               47

<210> SEQ ID NO 60
<211> LENGTH: 49
<212> TYPE: DNA
<213> ORGANISM: Homo sapiens

<400> SEQUENCE: 60
ttgtcccaca gatatccaga accctgaccc tgccgtgtac cagctgaga             49

<210> SEQ ID NO 61
<211> LENGTH: 49
<212> TYPE: DNA
<213> ORGANISM: Homo sapiens

<400> SEQUENCE: 61
tgtgtttgag ccatcagaag cagagatctc ccacacccaa aaggccaca        49

<210> SEQ ID NO 62
<211> LENGTH: 50
<212> TYPE: DNA
<213> ORGANISM: Homo sapiens

<400> SEQUENCE: 62
ttcccacccg aggtcgctgt gtttgagcca tcagaagcag agatctccca        50

<210> SEQ ID NO 63
<211> LENGTH: 49
<212> TYPE: DNA
<213> ORGANISM: Homo sapiens

<400> SEQUENCE: 63
tttagaaagt tcctgtgatg tcaagctggt cgagaaaagc tttgaaaca        49

<210> SEQ ID NO 64
<211> LENGTH: 49
<212> TYPE: DNA
<213> ORGANISM: Homo sapiens

<400> SEQUENCE: 64
tccagtgaca agtctgtctg cctattcacc gattttgatt ctcaaacaa        49

<210> SEQ ID NO 65
<211> LENGTH: 49
<212> TYPE: DNA
<213> ORGANISM: Homo sapiens

<400> SEQUENCE: 65
tatatcacag acaaaactgt gctagacatg aggtctatgg acttcaaga        49

<210> SEQ ID NO 66
<211> LENGTH: 49
<212> TYPE: DNA
<213> ORGANISM: Homo sapiens

<400> SEQUENCE: 66
tgaggtctat ggacttcaag agcaacagtg ctgtggcctg gagcaacaa        49

<210> SEQ ID NO 67
<211> LENGTH: 2814
<212> TYPE: DNA
<213> ORGANISM: Artificial Sequence
<220> FEATURE:
<223> OTHER INFORMATION: TALE-nuclease sequence

<400> SEQUENCE: 67
atgggcgatc ctaaaaagaa acgtaaggtc atcgattacc catacgatgt tccagattac        60
gctatcgata tcgccgatct acgcacgctc ggctacagcc agcagcaaca ggagaagatc       120
aaaccgaagg ttcgttcgac agtggcgcag caccacgagg cactggtcgg ccacgggttt       180
acacacgcgc acatcgttgc gttaagccaa caccccggcag cgttagggac cgtcgctgtc       240

```
aagtatcagg acatgatcgc agcgttgcca gaggcgacac acgaagcgat cgttggcgtc      300
ggcaaacagt ggtccggcgc acgcgctctg gaggccttgc tcacggtggc gggagagttg      360
agaggtccac cgttacagtt ggacacaggc caacttctca agattgcaaa acgtggcggc      420
gtgaccgcag tggaggcagt gcatgcatgg cgcaatgcac tgacgggtgc ccgctcaac       480 ttgaccccgg agcaggtggt ggccatcgcc agccacgatg gcggcaagca ggcgctggag      540
acggtccagc ggctgttgcc ggtgctgtgc caggcccacg gcttgacccc ggagcaggtg      600
gtggccatcg ccagccacga tggcggcaag caggcgctgg agacggtcca gcggctgttg      660
ccggtgctgt gccaggccca cggcttgacc ccggagcagg tggtggccat cgccagcaat      720
attggtggca agcaggcgct ggagacggtg caggcgctgt gccggtgct gtgccaggcc       780 cacggcttga ccccggagca ggtggtggcc atcgccagca atattggtgg caagcaggcg      840
ctggagacgg tgcaggcgct gttgccggtg ctgtgccagg cccacggctt gaccccggag      900
caggtggtgg ccatcgccag caatattggt ggcaagcagg cgctggagac ggtgcaggcg      960
ctgttgccgg tgctgtgcca ggcccacggc ttgaccccc agcaggtggt ggccatcgcc      1020
agcaataatg gtggcaagca ggcgctggag acggtccagc ggctgttgcc ggtgctgtgc     1080
caggcccacg gcttgacccc ggagcaggtg gtggccatcg ccagcaatat tggtggcaag     1140
caggcgctgg agacggtgca ggcgctgttg ccggtgctgt gccaggccca cggcttgacc     1200
ccccagcagg tggtggccat cgccagcaat ggcggtggca agcaggcgct ggagacggtc     1260
cagcggctgt tgccggtgct gtgccaggcc cacggcttga ccccccagca ggtggtggcc     1320
atcgccagca atggcggtgg caagcaggcg ctggagacgg tccagcggct gttgccggtg     1380
ctgtgccagg cccacggctt gaccccggag caggtggtgg ccatcgccag ccacgatggc     1440
ggcaagcagg cgctggagac ggtccagcgg ctgttgccgg tgctgtgcca ggcccacggc     1500
ttgaccccgg agcaggtggt ggccatcgcc agcaatattg gtggcaagca ggcgctggag     1560
acggtgcagg cgctgttgcc ggtgctgtgc caggcccacg gcttgacccc ccagcaggtg     1620
gtggccatcg ccagcaataa tggtggcaag caggcgctgg agacggtcca gcggctgttg     1680
ccggtgctgt gccaggccca cggcttgacc ccccagcagg tggtggccat cgccagcaat     1740
aatggtggca agcaggcgct ggagacggtc cagcggctgt tgccggtgct gtgccaggcc     1800
cacggcttga ccccccagca ggtggtggcc atcgccagca atggcggtgg caagcaggcg     1860
ctggagacgg tccagcggct gttgccggtg ctgtgccagg cccacggctt gaccccccag     1920
caggtggtgg ccatcgccag caatggcggt ggcaagcagg cgctggagac ggtccagcgg     1980
ctgttgccgg tgctgtgcca ggcccacggc ttgacccctc agcaggtggt ggccatcgcc     2040
agcaatggcg gcggcaggcc ggcgctggag agcattgttg cccagttatc tcgccctgat     2100
ccggcgttgg ccgcgttgac caacgaccac ctcgtcgcct tggcctgcct cggcgggcgt     2160
cctgcgctgg atgcagtgaa aaagggattg ggggatccta tcagccgttc ccagctggtg     2220
aagtccgagc tggaggagaa gaaatccgag ttgaggcaca agctgaagta cgtgccccac     2280
gagtacatcg agctgatcga gatcgcccgg aacagcaccc aggaccgtat cctggagatg     2340
aaggtgatga gttcttcat gaaggtgtac ggctacaggg gcaagcacct gggcggctcc      2400
aggaagcccg acggcgccat ctacaccgtg ggctccccca tcgactacgg cgtgatcgtg     2460
gacaccaagg cctactccgg cggctacaac ctgcccatcg ccaggcgga cgaaatgcag      2520 aggtacgtga aggagaacca gaccaggaac aagcacatca cccccaacga gtggtggaag     2580
gtgtacccct ccagcgtgac cgagttcaag ttcctgttcg tgtccggcca cttcaagggc     2640
```

```
aactacaagg cccagctgac caggctgaac cacatcacca actgcaacgg cgccgtgctg    2700
tccgtggagg agctcctgat cggcggcgag atgatcaagg ccggcaccct gaccctggag    2760
gaggtgagga ggaagttcaa caacggcgag atcaacttcg cggccgactg ataa          2814

<210> SEQ ID NO 68
<211> LENGTH: 2832
<212> TYPE: DNA
<213> ORGANISM: Artificial Sequence
<220> FEATURE:
<223> OTHER INFORMATION: TALE-nuclease sequence

<400> SEQUENCE: 68
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccg tcgctgtcaa gtatcaggac atgatcgcag cgttgccaga ggcgacacac     300
gaagcgatct tggcgtcgg caaacagtgg tccggcgcac gcgctctgga ggccttgctc      360
acggtggcgg gagagttgag aggtccaccg ttacagttgg acacaggcca acttctcaag     420
attgcaaaac gtggcggcgt gaccgcagtg gaggcagtgc atgcatggcg caatgcactg     480
acgggtgccc cgctcaactt gaccccccag caggtggtgg ccatcgccag caataatggt     540
ggcaagcagg cgctggagac ggtccagcgg ctgttgccgg tgctgtgcca ggcccacggc     600
ttgaccccgg agcaggtggt ggccatcgcc agcaatattg gtggcaagca ggcgctggag     660
acggtgcagg cgctgttgcc ggtgctgtgc caggcccacg gcttgacccc ggagcaggtg     720
gtggccatcg ccagccacga tggcggcaag caggcgctgg agacggtcca gcggctgttg     780
ccggtgctgt gccaggccca cggcttgacc cccagcagg tggtggccat cgccagcaat      840
ggcggtggca agcaggcgct ggagacggtc cagcggctgt tgccggtgct gtgccaggcc     900
cacggcttga ccccccagca ggtggtggcc atcgccagca atggcggtgg caagcaggcg     960
ctggagacgg tccagcggct gttgccggtg ctgtgccagg cccacggctt gaccccccag    1020
caggtggtgg ccatcgccag caatggcggt ggcaagcagg cgctggagac ggtccagcgg    1080
ctgttgccgg tgctgtgcca ggcccacggc ttgaccccgg agcaggtggt ggccatcgcc    1140
agccacgatg gcggcaagca ggcgctggag acggtccagc ggctgttgcc ggtgctgtgc    1200
caggcccacg gcttgacccc ggagcaggtg gtggccatcg ccagccacga tggcggcaag    1260
caggcgctgg agacggtcca gcggctgttg ccggtgctgt gccaggccca cggcttgacc    1320
ccggagcagg tggtggccat cgccagcaat attggtggca agcaggcgct ggagacggtg    1380
caggcgctgt tgccggtgct gtgccaggcc cacggcttga ccccccagca ggtggtggcc    1440
atcgccagca atggcggtgg caagcaggcg ctggagacgg tccagcggct gttgccggtg    1500
ctgtgccagg cccacggctt gaccccccag caggtggtgg ccatcgccag caatggcggt    1560
ggcaagcagg cgctggagac ggtccagcgg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ccagcaggtg    1740
gtggccatcg ccagcaatgg cggtggcaag caggcgctgg agacggtcca gcggctgttg    1800
ccggtgctgt gccaggccca cggcttgacc ccggagcagg tggtggccat cgccagccac    1860
```

```
gatggcggca agcaggcgct ggagacggtc cagcggctgt tgccggtgct gtgccaggcc    1920
cacggcttga ccccccagca ggtggtggcc atcgccagca atggcggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga atccgagtt gaggcacaag    2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtacccctcc agcgtgaccg agttcaagtt cctgttcgtg    2640
tccggccact tcaagggcaa ctacaaggcc cagctgacca ggctgaacca tcatcaacaac    2700 tgcaacggcg ccgtgctgtc cgtggaggag ctcctgatcg gcggcgagat gatcaaggcc    2760 ggcacccctga ccctggagga ggtgaggagg aagttcaaca acggcgagat caacttcgcg    2820
gccgactgat aa                                                        2832

<210> SEQ ID NO 69
<211> LENGTH: 2814
<212> TYPE: DNA
<213> ORGANISM: Artificial Sequence
<220> FEATURE:
<223> OTHER INFORMATION: TALE-nuclease sequence

<400> SEQUENCE: 69
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa cacccggcag cgttagggac cgtcgctgtc     240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca agattgcaaa acgtggcggc     420
gtgaccgcag tggaggcagt gcatgcatgg cgcaatgcac tgacgggtgc cccgctcaac     480 ttgaccccccc agcaggtggt ggccatcgcc agcaatggcg gtggcaagca ggcgctggag    540
acggtccagc ggctgttgcc ggtgctgtgc caggcccacg gcttgacccc ccagcaggtg     600
gtggccatcg ccagcaataa tggtggcaag caggcgctgg agacggtcca gcggctgttg    660
ccggtgctgt gccaggccca cggcttgacc ccccagcagg tggtggccat cgccagcaat    720
ggcggtggca agcaggcgct ggagacggtc cagcggctgt tgccggtgct gtgccaggcc    780
cacggcttga ccccggagca ggtggtggcc atcgccagcc acgatggcgg caagcaggcg    840
ctggagacgg tccagcggct gttgccggtg ctgtgccagg cccacggctt gaccccggag    900
caggtggtgg ccatcgccag ccacgatggc ggcaagcagg cgctggagac ggtccagcgg   960
ctgttgccgg tgctgtgcca ggcccacggc ttgaccccgg agcaggtggt ggccatcgcc    1020
agccacgatg gcggcaagca ggcgctggag acggtccagc ggctgttgcc ggtgctgtgc    1080
```

-continued

```
caggcccacg gcttgacccc ggagcaggtg gtggccatcg ccagcaatat tggtggcaag      1140
caggcgctgg agacggtgca ggcgctgttg ccggtgctgt gccaggccca cggcttgacc      1200
ccggagcagg tggtggccat cgccagccac gatggcggca agcaggcgct ggagacggtc      1260
cagcggctgt tgccggtgct gtgccaggcc cacggcttga ccccggagca ggtggtggcc      1320
atcgccagca atattggtgg caagcaggcg ctggagacgg tgcaggcgct gttgccggtg      1380
ctgtgccagg cccacggctt gaccccccag caggtggtgg ccatcgccag caataatggt      1440
ggcaagcagg cgctggagac ggtccagcgg ctgttgccgg tgctgtgcca ggcccacggc      1500
ttgaccccgg agcaggtggt ggccatcgcc agcaatattg gtggcaagca ggcgctggag      1560
acggtgcagg cgctgttgcc ggtgctgtgc caggcccacg gcttgacccc cagcaggtg       1620 gtggccatcg ccagcaatgg cggtggcaag caggcgctgg agacggtcca gcggctgttg      1680
ccggtgctgt gccaggccca cggcttgacc ccggagcagg tggtggccat cgccagcaat      1740
attggtggca agcaggcgct ggagacggtg caggcgctgt tgccggtgct gtgccaggcc      1800
cacggcttga ccccccagca ggtggtggcc atcgccagca atggcggtgg caagcaggcg      1860
ctggagacgg tccagcggct gttgccggtg ctgtgccagg cccacggctt gaccccggag      1920
caggtggtgg ccatcgccag ccacgatggc ggcaagcagg cgctggagac ggtccagcgg      1980
ctgttgccgg tgctgtgcca ggcccacggc ttgaccccctc agcaggtggt ggccatcgcc      2040
agcaatggcg gcggcaggcc ggcgctggag agcattgttg cccagttatc tcgccctgat      2100
ccggcgttgg ccgcgttgac caacgaccac ctcgtcgcct tggcctgcct cggcgggcgt      2160
cctgcgctgg atgcagtgaa aaagggattg ggggatccta tcagccgttc ccagctggtg      2220
aagtccgagc tggaggagaa gaaatccgag ttgaggcaca agctgaagta cgtgcccac      2280 gagtacatcg agctgatcga gatcgcccgg aacagcaccc aggaccgtat cctggagatg      2340
aaggtgatgg agttcttcat gaaggtgtac ggctacaggg gcaagcacct gggcggctcc      2400
aggaagcccg acggcgccat ctacaccgtg gctccccca tcgactacgg cgtgatcgtg      2460
gacaccaagg cctactccgg cggctacaac ctgcccatcg ccaggcgca cgaaatgcag      2520 aggtacgtgg aggagaacca gaccaggaac aagcacatca acccaacga gtggtggaag      2580 gtgtaccct ccagcgtgac cgagttcaag ttcctgttcg tgtccggcca cttcaagggc       2640
aactacaagg cccagctgac caggctgaac acatcacca actgcaacgg cgccgtgctg      2700
tccgtggagg agctcctgat cggcggcgag atgatcaagg ccggcaccct gaccctggag      2760
gaggtgagga ggaagttcaa caacggcgag atcaacttcg cggccgactg ataa            2814
```

<210> SEQ ID NO 70
<211> LENGTH: 2832
<212> TYPE: DNA
<213> ORGANISM: Artificial Sequence
<220> FEATURE:
<223> OTHER INFORMATION: TALE-nuclease sequence

<400> SEQUENCE: 70

```
atgggcgatc ctaaaaagaa acgtaaggtc atcgataagg agaccgccgc tgccaagttc        60
gagagacagc acatggacag catcgatatc gccgatctac gcacgctcgg ctacagccag      120
cagcaacagg agaagatcaa accgaaggtt cgttcgacag tggcgcagca ccacgaggca      180
ctggtcggcc acgggtttac acacgcgcac atcgttgcgt taagccaaca cccggcagcg      240
ttagggaccg tcgctgtcaa gtatcaggac atgatcgcag cgttgccaga ggcgacacac      300
```

-continued

```
gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gaccccggag caggtggtgg ccatcgccag ccacgatggc    540
ggcaagcagg cgctggagac ggtccagcgg ctgttgccgg tgctgtgcca ggcccacggc    600
ttgaccccc agcaggtggt ggccatcgcc agcaatggcg gtggcaagca ggcgctggag     660
acggtccagc ggctgttgcc ggtgctgtgc caggcccacg gcttgacccc ggagcaggtg    720
gtggccatcg ccagccacga tggcggcaag caggcgctgg agacggtcca gcggctgttg    780
ccggtgctgt gccaggccca cggcttgacc ccggagcagg tggtggccat cgccagcaat    840
attggtggca agcaggcgct ggagacggtg caggcgctgt tgccggtgct gtgccaggcc    900
cacggcttga ccccccagca ggtggtggcc atcgccagca ataatggtgg caagcaggcg    960
ctggagacgg tccagcggct gttgccggtc tgtgccagg cccacggctt gaccccggag    1020
caggtggtgg ccatcgccag ccacgatggc ggcaagcagg cgctggagac ggtccagcgg    1080
ctgttgccgg tgctgtgcca ggcccacggc ttgaccccc agcaggtggt ggccatcgcc     1140
agcaatggcg gtggcaagca ggcgctggag acggtccagc ggctgttgcc ggtgctgtgc    1200
caggcccacg gcttgacccc cagcaggtg gtggccatcg ccagcaataa tggtggcaag     1260
caggcgctgg agacggtcca gcggctgttg ccggtgctgt gccaggccca cggcttgacc    1320
ccccagcagg tggtggccat cgccagcaat aatggtggca agcaggcgct ggagacggtc    1380
cagcggctgt tgccggtgct gtgccaggcc cacggcttga ccccccagca ggtggtggcc    1440
atcgccagca atggcggtgg caagcaggcg ctggagacgg tccagcggct gttgccggtg    1500
ctgtgccagg cccacggctt gaccccggag caggtggtgg ccatcgccag caatattggt    1560
ggcaagcagg cgctggagac ggtgcaggcg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc ccggagcagg tggtggccat cgccagccac    1860
gatggcggca agcaggcgct ggagacggtc agcggctgt tgccggtgct gtgccaggcc     1920
cacggcttga ccccccagca ggtggtggcc atcgccagca ataatggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga atccgagtt gaggcacaag     2280
ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccctcc agcgtgaccg agttcaagtt cctgttcgtg     2640
tccggccact tcaagggcaa ctacaaggcc cagctgacca ggctgaacca catcaccaac    2700
```

```
tgcaacggcg ccgtgctgtc cgtggaggag ctcctgatcg gcggcgagat gatcaaggcc    2760
ggcaccctga ccctggagga ggtgaggagg aagttcaaca acggcgagat caacttcgcg    2820
gccgactgat aa                                                        2832
```

<210> SEQ ID NO 71
<211> LENGTH: 2814
<212> TYPE: DNA
<213> ORGANISM: Artificial Sequence
<220> FEATURE:
<223> OTHER INFORMATION: TALE-nuclease sequence

<400> SEQUENCE: 71

```
atgggcgatc ctaaaaagaa acgtaaggtc atcgattacc catacgatgt tccagattac     60
gctatcgata tcgccgatct acgcacgctc ggctacagcc agcagcaaca ggagaagatc    120
aaaccgaagg ttcgttcgac agtggcgcag caccacgagg cactggtcgg ccacgggttt    180
acacacgcgc acatcgttgc gttaagccaa caccccggcag cgttagggac cgtcgctgtc    240
aagtatcagg acatgatcgc agcgttgcca gaggcgacac acgaagcgat cgttggcgtc    300
ggcaaacagt ggtccggcgc acgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480
ttgacccccc agcaggtggt ggccatcgcc agcaataatg gtggcaagca ggcgctggag    540
acggtccagc ggctgttgcc ggtgctgtgc caggcccacg gcttgacccc ccagcaggtg    600
gtggccatcg ccagcaatgg cggtggcaag caggcgctgg agacggtcca gcggctgttg    660
ccggtgctgt gccaggccca cggcttgacc ccccagcagg tggtggccat cgccagcaat    720
aatggtggca agcaggcgct ggagacggtc agcggctgt gccggtgct gtgccaggcc    780 cacggcttga ccccccagca ggtggtggcc atcgccagca atggcggtgg caagcaggcg    840
ctggagacgg tccagcggct gttgccggtg ctgtgccagg cccacggctt gaccccccag    900
caggtggtgg ccatcgccag caatggcggt ggcaagcagg cgctggagac ggtccagcgg    960
ctgttgccgg tgctgtgcca ggcccacggc ttgaccccc agcaggtggt ggccatcgcc   1020
agcaatggcg gtggcaagca ggcgctggag acggtccagc ggctgttgcc ggtgctgtgc   1080
caggcccacg gcttgacccc ccagcaggtg gtggccatcg ccagcaataa tggtggcaag   1140
caggcgctgg agacggtcca gcggctgttg ccggtgctgt gccaggccca cggcttgacc   1200
ccggagcagg tggtggccat cgccagcaat attggtggca agcaggcgct ggagacggtg   1260
caggcgctgt gccggtgct gtgccaggcc cacggcttga ccccccagca ggtggtggcc   1320
atcgccagca ataatggtgg caagcaggcg ctggagacgg tccagcggct gttgccggtg   1380
ctgtgccagg cccacggctt gaccccggag caggtggtgg ccatcgccag ccacgatggc   1440
ggcaagcagg cgctggagac ggtccagcgg ctgttgccgg tgctgtgcca ggcccacggc   1500
ttgaccccgg agcaggtggt ggccatcgcc agccacgatg cggcaagca ggcgctggag   1560 acggtccagc ggctgttgcc ggtgctgtgc caggcccacg gcttgacccc ggagcaggtg   1620
gtggccatcg ccagcaatat tggtggcaag caggcgctgg agacggtgca ggcgctgttg   1680
ccggtgctgt gccaggccca cggcttgacc ccccagcagg tggtggccat cgccagcaat   1740
ggcggtggca agcaggcgct ggagacggtc agcggctgt gccggtgct gtgccaggcc   1800 cacggcttga ccccggagca ggtggtggcc atcgccagcc acgatggcgg caagcaggcg   1860
```

```
ctggagacgg tccagcggct gttgccggtg ctgtgccagg cccacggctt gaccccggag    1920
caggtggtgg ccatcgccag caatattggt ggcaagcagg cgctggagac ggtgcaggcg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca gctgaagta cgtgccccac     2280 gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg ggctccccca tcgactacgg cgtgatcgtg    2460
gacaccaagg cctactccgg cggctacaac ctgcccatcg ccaggccga cgaaatgcag     2520 aggtacgtgg aggagaacca gaccaggaac aagcacatca accccaacga gtggtggaag    2580
gtgtaccccc tccagcgtga ccgagttcaag ttcctgttcg tgtccggcca cttcaagggc   2640
aactacaagg cccagctgac caggctgaac cacatcacca actgcaacgg cgccgtgctg    2700
tccgtggagg agctcctgat cggcggcgag atgatcaagg ccggcaccct gacccctgag    2760
gaggtgagga ggaagttcaa caacggcgag atcaacttcg cggccgactg ataa          2814
```

<210> SEQ ID NO 72
<211> LENGTH: 2832
<212> TYPE: DNA
<213> ORGANISM: Artificial Sequence
<220> FEATURE:
<223> OTHER INFORMATION: TALE-nuclease sequence

<400> SEQUENCE: 72

```
atgggcgatc ctaaaaagaa acgtaaggtc atcgataagg agaccgccgc tgccaagttc      60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcag cgttgccaga ggcgacacac    300
gaagcgatcc ttgcgtcgg caaacagtgg tccggcgcac gcgctctgga ggccttgctc     360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gacccccag caggtggtgg ccatcgccag caataatggt     540
ggcaagcagg cgctggagac ggtccagcgg ctgttgccgg tgctgtgcca ggcccacggc    600 ttgaccccc agcaggtggt ggccatcgcc agcaatggcg gtggcaagca ggcgctggag     660
acggtccagc ggctgttgcc ggtgctgtgc caggcccacg gcttgacccc cagcaggtg     720 gtggccatcg ccagcaataa tggtggcaag caggcgctgg agacggtcca gcggctgttg    780
ccggtgctgt gccaggccca cggcttgacc cccagcagg tggtggccat cgccagcaat     840
aatggtggca agcaggcgct ggagacggtc agcggctgt tgccggtgct gtgccaggcc    900
cacggcttga ccccggagca ggtggtggcc atcgccagcc acgatggcgg caagcaggcg    960
ctggagacgg tccagcggct gttgccggtg ctgtgccagg cccacggctt gaccccggag   1020
caggtggtgg ccatcgccag ccacgatggc ggcaagcagg cgctggagac ggtccagcgg   1080
ctgttgccgg tgctgtgcca ggcccacggc ttgaccccc agcaggtggt ggccatcgcc    1140
```

-continued

```
agcaatggcg gtggcaagca ggcgctggag acggtccagc ggctgttgcc ggtgctgtgc    1200
caggcccacg gcttgacccc ccagcaggtg gtggccatcg ccagcaatgg cggtggcaag    1260
caggcgctgg agacggtcca gcggctgttg ccggtgctgt gccaggccca cggcttgacc    1320
ccccagcagg tggtggccat cgccagcaat ggcggtggca agcaggcgct ggagacggtc    1380
cagcggctgt tgccggtgct gtgccaggcc cacggcttga ccccccagca ggtggtggcc    1440
atcgccagca atggcggtgg caagcaggcg ctggagacgg tccagcggct gttgccggtg    1500
ctgtgccagg cccacggctt gacccccag caggtggtgg ccatcgccag caataatggt    1560
ggcaagcagg cgctggagac ggtccagcgg ctgttgccgg tgctgtgcca ggcccacggc    1620
ttgacccccc agcaggtggt ggccatcgcc agcaataatg gtggcaagca ggcgctggag    1680
acggtccagc ggctgttgcc ggtgctgtgc caggcccacg gcttgacccc ccagcaggtg    1740
gtggccatcg ccagcaataa tggtggcaag caggcgctgg agacggtcca gcggctgttg    1800
ccggtgctgt gccaggccca cggcttgacc ccccagcagg tggtggccat cgccagcaat    1860
ggcggtggca agcaggcgct ggagacggtc cagcggctgt tgccggtgct gtgccaggcc    1920
cacggcttga ccccccagca ggtggtggcc atcgccagca ataatggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga atccgagtt gaggcacaag    2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccctcc agcgtgaccg agttcaagtt cctgttcgtg    2640
tccggccact tcaagggcaa ctacaaggcc agctgacca ggctgaacca catcaccaac    2700
tgcaacggcg ccgtgctgtc cgtggaggag ctcctgatcg gcggcgagat gatcaaggcc    2760
ggcaccctga ccctggagga ggtgaggagg aagttcaaca acggcgagat caacttcgcg    2820
gccgactgat aa    2832
```

<210> SEQ ID NO 73
<211> LENGTH: 2814
<212> TYPE: DNA
<213> ORGANISM: Artificial Sequence
<220> FEATURE:
<223> OTHER INFORMATION: TALE-nuclease sequence

<400> SEQUENCE: 73

```
atgggcgatc ctaaaaagaa acgtaaggtc atcgattacc catacgatgt tccagattac    60
gctatcgata tcgccgatct acgcacgctc ggctacagcc agcagcaaca ggagaagatc    120
aaaccgaagg ttcgttcgac agtggcgcag caccacgagg cactggtcgg ccacgggttt    180
acacacgcgc acatcgttgc gttaagccaa cacccggcag cgttagggac cgtcgctgtc    240
aagtatcagg acatgatcgc agcgttgcca gaggcgacac acgaagcgat cgttggcgtc    300
```

| | |
|---|---|
| ggcaaacagt ggtccggcgc acgcgctctg gaggccttgc tcacggtggc gggagagttg | 360 |
| agaggtccac cgttacagtt ggacacaggc caacttctca agattgcaaa acgtggcggc | 420 |
| gtgaccgcag tggaggcagt gcatgcatgg cgcaatgcac tgacgggtgc cccgctcaac | 480 |
| ttgaccccgg agcaggtggt ggccatcgcc agccacgatg gcggcaagca ggcgctggag | 540 |
| acggtccagc ggctgttgcc ggtgctgtgc caggcccacg gcttgacccc ggagcaggtg | 600 |
| gtggccatcg ccagccacga tggcggcaag caggcgctgg agacggtcca gcggctgttg | 660 |
| ccggtgctgt gccaggccca cggcttgacc ccggagcagg tggtggccat cgccagccac | 720 |
| gatggcggca agcaggcgct ggagacggtc agcggctgt tgccggtgct gtgccaggcc | 780 |
| cacggcttga ccccggagca ggtggtggcc atcgccagca atattggtgg caagcaggcg | 840 |
| ctggagacgg tgcaggcgct gttgccggtg ctgtgccagg cccacggctt gaccccggag | 900 |
| caggtggtgg ccatcgccag ccacgatggc ggcaagcagg cgctggagac ggtccagcgg | 960 |
| ctgttgccgg tgctgtgcca ggcccacggc ttgaccccgg agcaggtggt ggccatcgcc | 1020 |
| agccacgatg gcggcaagca ggcgctggag acggtccagc ggctgttgcc ggtgctgtgc | 1080 |
| caggcccacg gcttgacccc ggagcaggtg gtggccatcg ccagccacga tggcggcaag | 1140 |
| caggcgctgg agacggtcca gcggctgttg ccggtgctgt gccaggccca cggcttgacc | 1200 |
| ccccagcagg tggtggccat cgccagcaat aatggtggca agcaggcgct ggagacggtc | 1260 |
| cagcggctgt tgccggtgct gtgccaggcc cacggcttga ccccggagca ggtggtggcc | 1320 |
| atcgccagca atattggtgg caagcaggcg ctggagacgg tgcaggcgct gttgccggtg | 1380 |
| ctgtgccagg cccacggctt gaccccccag caggtggtgg ccatcgccag caataatggt | 1440 |
| ggcaagcagg cgctggagac ggtccagcgg ctgttgccgg tgctgtgcca ggcccacggc | 1500 |
| ttgaccccc agcaggtggt ggccatcgcc agcaataatg gtggcaagca ggcgctggag | 1560 |
| acggtccagc ggctgttgcc ggtgctgtgc caggcccacg gcttgacccc ccagcaggtg | 1620 |
| gtggccatcg ccagcaatgg cggtggcaag caggcgctgg agacggtcca gcggctgttg | 1680 |
| ccggtgctgt gccaggccca cggcttgacc ccggagcagg tggtggccat cgccagccac | 1740 |
| gatggcggca agcaggcgct ggagacggtc agcggctgt tgccggtgct gtgccaggcc | 1800 |
| cacggcttga ccccccagca ggtggtggcc atcgccagca ataatggtgg caagcaggcg | 1860 |
| ctggagacgg tccagcggct gttgccggtg ctgtgccagg cccacggctt gaccccggag | 1920 |
| caggtggtgg ccatcgccag ccacgatggc ggcaagcagg cgctggagac ggtccagcgg | 1980 |
| ctgttgccgg tgctgtgcca ggcccacggc ttgaccccctc agcaggtggt ggccatcgcc | 2040 |
| agcaatggcg gcggcaggcc ggcgctggag agcattgttg cccagttatc tcgccctgat | 2100 |
| ccggcgttgg ccgcgttgac caacgaccac ctcgtcgcct tggcctgcct cggcgggcgt | 2160 |
| cctgcgctgg atgcagtgaa aaagggattg ggggatccta tcagccgttc ccagctggtg | 2220 |
| aagtccgagc tggaggagaa gaaatccgag ttgaggcaca agctgaagta cgtgccccac | 2280 |
| gagtacatcg agctgatcga gatcgcccgg aacagcaccc aggaccgtat cctggagatg | 2340 |
| aaggtgatgg agttcttcat gaaggtgtac ggctacaggg gcaagcacct gggcggctcc | 2400 |
| aggaagcccg acgcgccat ctacaccgtg ggctcccccaa tcgactacgg cgtgatcgtg | 2460 |
| gacaccaagg cctactccgg cggctacaac ctgcccatcg gccaggccga cgaaatgcag | 2520 |
| aggtacgtgg aggagaacca gaccaggaac aagcacatca accccaacga gtggtggaag | 2580 |
| gtgtacccct ccagcgtgac cgagttcaag ttcctgttcg tgtccggcca cttcaagggc | 2640 |
| aactacaagg cccagctgac caggctgaac cacatcacca actgcaacgg cgccgtgctg | 2700 |

```
tccgtggagg agctcctgat cggcggcgag atgatcaagg ccggcaccct gaccctggag    2760
gaggtgagga ggaagttcaa caacggcgag atcaacttcg cggccgactg ataa         2814

<210> SEQ ID NO 74
<211> LENGTH: 2832
<212> TYPE: DNA
<213> ORGANISM: Artificial Sequence
<220> FEATURE:
<223> OTHER INFORMATION: TALE-nuclease sequence

<400> SEQUENCE: 74
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccg tcgctgtcaa gtatcaggac atgatcgcag cgttgccaga ggcgacacac     300
gaagcgatcg ttggcgtcgg caaacagtgg tccggcgcac gcgctctgga ggccttgctc     360
acggtggcgg gagagttgag aggtccaccg ttacagttgg acacaggcca acttctcaag     420
attgcaaaac gtggcggcgt gaccgcagtg gaggcagtgc atgcatggcg caatgcactg     480
acgggtgccc cgctcaactt gaccccccag caggtggtgg ccatcgccag caataatggt     540
ggcaagcagg cgctggagac ggtccagcgg ctgttgccgg tgctgtgcca ggcccacggc     600 ttgaccccc agcaggtggt ggccatcgcc agcaataatg gtggcaagca ggcgctggag     660
acggtccagc ggctgttgcc ggtgctgtgc caggcccacg gcttgacccc ccagcaggtg     720
gtggccatcg ccagcaataa tggtggcaag caggcgctgg agacggtcca gcggctgttg     780
ccggtgctgt gccaggccca cggcttgacc ccggagcagg tggtggccat cgccagcaat     840
attggtggca agcaggcgct ggagacggtg caggcgctgt gccggtgct gtgccaggcc     900 cacggcttga ccccccagca ggtggtggcc atcgccagca ataatggtgg caagcaggcg     960
ctggagacgg tccagcggct gttgccggtg ctgtgccagg cccacggctt gaccccggag    1020
caggtggtgg ccatcgccag caatattggt ggcaagcagg cgctggagac ggtgcaggcg    1080
ctgttgccgg tgctgtgcca ggcccacggc ttgaccccc agcaggtggt ggccatcgcc    1140
agcaatggcg gtggcaagca ggcgctggag acggtccagc ggctgttgcc ggtgctgtgc    1200
caggcccacg gcttgacccc ggagcaggtg gtggccatcg ccagccacga tggcggcaag    1260
caggcgctgg agacggtcca gcggctgttg ccggtgctgt gccaggccca cggcttgacc    1320
ccccagcagg tggtggccat cgccagcaat ggcggtggca agcaggcgct ggagacggtc    1380
cagcggctgt tgccggtgct gtgccaggcc cacggcttga ccccggagca ggtggtggcc    1440
atcgccagcc acgatggcgg caagcaggcg ctggagacgg tccagcggct gttgccggtg    1500
ctgtgccagg cccacggctt gaccccccag caggtggtgg ccatcgccag caatggcggt    1560
ggcaagcagg cgctggagac ggtccagcgg ctgttgccgg tgctgtgcca ggcccacggc    1620 ttgaccccc agcaggtggt ggccatcgcc agcaataatg gtggcaagca ggcgctggag    1680
acggtccagc ggctgttgcc ggtgctgtgc caggcccacg gcttgacccc ggagcaggtg    1740
gtggccatcg ccagccacga tggcggcaag caggcgctgg agacggtcca gcggctgttg    1800
ccggtgctgt gccaggccca cggcttgacc ccccagcagg tggtggccat cgccagcaat    1860
ggcggtggca agcaggcgct ggagacggtc cagcggctgt tgccggtgct gtgccaggcc    1920
```

```
cacggcttga ccccccagca ggtggtggcc atcgccagca atggcggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga aatccgagtt gaggcacaag    2280
ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccccctcc agcgtgaccg agttcaagtt cctgttcgtg    2640
tccggccact tcaagggcaa ctacaaggcc cagctgacca ggctgaacca catcaccaac    2700
tgcaacggcg ccgtgctgtc cgtggaggag ctcctgatcg gcggcgagat gatcaaggcc    2760 ggcacccctga ccctggagga ggtgaggagg aagttcaaca acggcgagat caacttcgcg    2820
gccgactgat aa                                                       2832

<210> SEQ ID NO 75
<211> LENGTH: 21
<212> TYPE: DNA
<213> ORGANISM: Artificial Sequence
<220> FEATURE:
<223> OTHER INFORMATION: PCR primer

<400> SEQUENCE: 75
atcactggca tctggactcc a                                               21

<210> SEQ ID NO 76
<211> LENGTH: 22
<212> TYPE: DNA
<213> ORGANISM: Artificial Sequence
<220> FEATURE:
<223> OTHER INFORMATION: PCR primer

<400> SEQUENCE: 76
agagccccta ccagaaccag ac                                              22

<210> SEQ ID NO 77
<211> LENGTH: 22
<212> TYPE: DNA
<213> ORGANISM: Artificial Sequence
<220> FEATURE:
<223> OTHER INFORMATION: PCR primer

<400> SEQUENCE: 77
ggacctagta acataattgt gc                                              22

<210> SEQ ID NO 78
<211> LENGTH: 20
<212> TYPE: DNA
<213> ORGANISM: Artificial Sequence
<220> FEATURE:
<223> OTHER INFORMATION: PCR primer

<400> SEQUENCE: 78
cctcatgtct agcacagttt                                                 20
```

<210> SEQ ID NO 79
<211> LENGTH: 21
<212> TYPE: DNA
<213> ORGANISM: Artificial Sequence
<220> FEATURE:
<223> OTHER INFORMATION: PCR primer

<400> SEQUENCE: 79
accagctcag ctccacgtgg t                                       21

<210> SEQ ID NO 80
<211> LENGTH: 58
<212> TYPE: DNA
<213> ORGANISM: Homo sapiens

<400> SEQUENCE: 80
tctcgctccg tggccttagc tgtgctcgcg ctactctctc tttctggcct ggaggcta    58

<210> SEQ ID NO 81
<211> LENGTH: 2814
<212> TYPE: DNA
<213> ORGANISM: Artificial Sequence
<220> FEATURE:
<223> OTHER INFORMATION: Beta2M T01- TALEN - LEFT

<400> SEQUENCE: 81
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc acatcgttgc gttaagccaa caccccggcag cgttagggac cgtcgctgtc   240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca agattgcaaa acgtggcggc   420
gtgaccgcag tggaggcagt gcatgcatgg cgcaatgcac tgacgggtgc cccgctcaac   480
ttgacccccc agcaggtggt ggccatcgcc agcaataatg gtggcaagca ggcgctggag   540
acggtccagc ggctgttgcc ggtgctgtgc caggcccacg gcttgacccc ccagcaggtg   600
gtggccatcg ccagcaataa tggtggcaag caggcgctgg agacggtcca gcggctgttg   660
ccggtgctgt gccaggccca cggcttgacc ccggagcagg tggtggccat cgccagccac   720
gatggcggca agcaggcgct ggagacggtc agcggctgt gccggtgct gtgccaggcc   780 cacggcttga ccccggagca ggtggtggcc atcgccagcc acgatggcgg caagcaggcg   840
ctggagacgg tccagcggct gttgccggtg ctgtgccagg cccacggctt gaccccccag   900
caggtggtgg ccatcgccag caatggcggt ggcaagcagg cgctggagac ggtccagcgg   960
ctgttgccgg tgctgtgcca ggcccacggc ttgaccccc agcaggtggt ggccatcgcc   1020
agcaatggcg gtggcaagca ggcgctggag acggtccagc ggctgttgcc ggtgctgtgc   1080
caggcccacg gcttgacccc ggagcaggtg gtggccatcg ccagcaatat tggtggcaag   1140
caggcgctgg agacggtgca ggcgctgttg ccggtgctgt gccaggccca cggcttgacc   1200
ccccagcagg tggtggccat cgccagcaat aatggtggca agcaggcgct ggagacggtc   1260
cagcggctgt tgccggtgct gtgccaggcc cacggcttga ccccggagca ggtggtggcc   1320
atcgccagcc acgatggcgg caagcaggcg ctggagacgg tccagcggct gttgccggtg   1380

| | |
|---|---|
| ctgtgccagg cccacggctt gacccccag caggtggtgg ccatcgccag caatggcggt | 1440 |
| ggcaagcagg cgctggagac ggtccagcgg ctgttgccgg tgctgtgcca ggcccacggc | 1500 |
| ttgaccccc agcaggtggt ggccatcgcc agcaataatg gtggcaagca ggcgctggag | 1560 |
| acggtccagc ggctgttgcc ggtgctgtgc caggcccacg gcttgacccc ccagcaggtg | 1620 |
| gtggccatcg ccagcaatgg cggtggcaag caggcgctgg agacggtcca gcggctgttg | 1680 |
| ccggtgctgt gccaggccca cggcttgacc cccagcagg tggtggccat cgccagcaat | 1740 |
| aatggtggca agcaggcgct ggagacggtc agcggctgt tgccggtgct gtgccaggcc | 1800 |
| cacggcttga ccccggagca ggtggtggcc atcgccagcc acgatggcgg caagcaggcg | 1860 |
| ctggagacgg tccagcggct gttgccggtg ctgtgccagg cccacggctt gacccccag | 1920 |
| caggtggtgg ccatcgccag caatggcggt ggcaagcagg cgctggagac ggtccagcgg | 1980 |
| ctgttgccgg tgctgtgcca ggcccacggc ttgacccctc agcaggtggt ggccatcgcc | 2040 |
| agcaatggcg gcggcaggcc ggcgctggag agcattgttg cccagttatc tcgccctgat | 2100 |
| ccggcgttgg ccgcgttgac caacgaccac ctcgtcgcct tggcctgcct cggcgggcgt | 2160 |
| cctgcgctgg atgcagtgaa aaagggattg ggggatccta tcagccgttc ccagctggtg | 2220 |
| aagtccgagc tggaggagaa gaaatccgag ttgaggcaca gctgaagta cgtgccccac | 2280 |
| gagtacatcg agctgatcga gatcgcccgg aacagcaccc aggaccgtat cctggagatg | 2340 |
| aaggtgatgg agttcttcat gaaggtgtac ggctacaggg gcaagcacct gggcggctcc | 2400 |
| aggaagcccg acggcgccat ctacaccgtg ggctccccca tcgactacgg cgtgatcgtg | 2460 |
| gacaccaagg cctactccgg cggctacaac ctgcccatcg gccaggccga cgaaatgcag | 2520 |
| aggtacgtgg aggagaacca gaccaggaac aagcacatca ccccaacga gtggtggaag | 2580 |
| gtgtacccct ccagcgtgac cgagttcaag ttcctgttcg tgtccggcca cttcaagggc | 2640 |
| aactacaagg cccagctgac caggctgaac cacatcacca actgcaacgg cgccgtgctg | 2700 |
| tccgtggagg agctcctgat cggcggcgag atgatcaagg ccggcaccct gaccctggag | 2760 |
| gaggtgagga ggaagttcaa caacggcgag atcaacttcg cggccgactg ataa | 2814 |

<210> SEQ ID NO 82
<211> LENGTH: 2832
<212> TYPE: DNA
<213> ORGANISM: Artificial Sequence
<220> FEATURE:
<223> OTHER INFORMATION: Beta2M T01 TALEN -RIGHT

<400> SEQUENCE: 82

| | |
|---|---|
| atgggcgatc taaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |
| ttagggaccg tcgctgtcaa gtatcaggac atgatcgcac gttgccaga ggcgacacac | 300 |
| gaagcgatcg ttggcgtcgg caaacagtgg tccggcgcac gcgctctgga ggccttgctc | 360 |
| acggtggcgg gagagttgag aggtccaccg ttacagttgg acacaggcca acttctcaag | 420 |
| attgcaaaac gtggcggcgt gaccgcagtg gaggcagtgc atgcatggcg caatgcactg | 480 |
| acgggtgccc cgctcaactt gacccggag caggtggtgg ccatcgccag caatattggt | 540 |
| ggcaagcagg cgctggagac ggtgcaggcg ctgttgccgg tgctgtgcca ggcccacggc | 600 |
| ttgacccccc agcaggtggt ggccatcgcc agcaataatg gtggcaagca ggcgctggag | 660 |

-continued

```
acggtccagc ggctgttgcc ggtgctgtgc caggcccacg gcttgacccc ggagcaggtg    720
gtggccatcg ccagccacga tggcggcaag caggcgctgg agacggtcca gcggctgttg    780
ccggtgctgt gccaggccca cggcttgacc ccggagcagg tggtggccat cgccagccac    840
gatggcggca agcaggcgct ggagacggtc agcggctgt tgccggtgct gtgccaggcc    900
cacggcttga ccccccagca ggtggtggcc atcgccagca atggcggtgg caagcaggcg    960
ctggagacgg tccagcggct gttgccggtg ctgtgccagg cccacggctt gaccccggag   1020
caggtggtgg ccatcgccag ccacgatggc ggcaagcagg cgctggagac ggtccagcgg   1080
ctgttgccgg tgctgtgcca ggcccacggc ttgaccccgg agcaggtggt ggccatcgcc   1140
agccacgatg gcggcaagca ggcgctggag acggtccagc ggctgttgcc ggtgctgtgc   1200
caggcccacg gcttgacccc ggagcaggtg gtggccatcg ccagcaatat tggtggcaag   1260
caggcgctgg agacggtgca ggcgctgttg ccggtgctgt gccaggccca cggcttgacc   1320
ccccagcagg tggtggccat cgccagcaat aatggtggca agcaggcgct ggagacggtc   1380
cagcggctgt tgccggtgct gtgccaggcc cacggcttga ccccccagca ggtggtggcc   1440
atcgccagca ataatggtgg caagcaggcg ctggagacgg tccagcggct gttgccggtg   1500
ctgtgccagg cccacggctt gaccccggag caggtggtgg ccatcgccag ccacgatggc   1560
ggcaagcagg cgctggagac ggtccagcgg ctgttgccgg tgctgtgcca ggcccacggc   1620
ttgaccccgg agcaggtggt ggccatcgcc agccacgatg gcggcaagca ggcgctggag   1680
acggtccagc ggctgttgcc ggtgctgtgc caggcccacg gcttgacccc ggagcaggtg   1740
gtggccatcg ccagcaatat tggtggcaag caggcgctgg agacggtgca ggcgctgttg   1800
ccggtgctgt gccaggccca cggcttgacc ccccagcagg tggtggccat cgccagcaat   1860
aatggtggca agcaggcgct ggagacggtc agcggctgt tgccggtgct gtgccaggcc   1920
cacggcttga ccccggagca ggtggtggcc atcgccagca atattggtgg caagcaggcg   1980
ctggagacgg tgcaggcgct gttgccggtg ctgtgccagg cccacggctt gacccctcag   2040
caggtggtgg ccatcgccag caatggcggc ggcaggccgg cgctggagag cattgttgcc   2100
cagttatctc gccctgatcc ggcgttggcc gcgttgacca cgaccacct cgtcgccttg   2160 gcctgcctcg gcgggcgtcc tgcgctggat gcagtgaaaa agggattggg ggatcctatc   2220
agccgttccc agctggtgaa gtccgagctg aggagaagaa atccgagtt gaggcacaag   2280 ctgaagtacg tgccccacga gtacatcgag ctgatcgaga tcgcccggaa cagcacccag   2340
gaccgtatcc tggagatgaa ggtgatggag ttcttcatga aggtgtacgg ctacagggc    2400 aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtacccctcc agcgtgaccg agttcaagtt cctgttcgtg   2640
tccggccact tcaagggcaa ctacaaggcc cagctgacca ggctgaacca catcaccaac   2700
tgcaacggcg ccgtgctgtc cgtggaggag ctcctgatcg gcggcgagat gatcaaggcc   2760 ggcacctga ccctggagga ggtgaggagg aagttcaaca cggcgagat caacttcgcg    2820 gccgactgat aa                                                       2832
```

<210> SEQ ID NO 83
<211> LENGTH: 50
<212> TYPE: DNA

```
<213> ORGANISM: Artificial Sequence
<220> FEATURE:
<223> OTHER INFORMATION: B2M T02- TALEN targeting sequence

<400> SEQUENCE: 83
tccaaagatt caggtttact cacgtcatcc agcagagaat ggaaagtcaa            50

<210> SEQ ID NO 84
<211> LENGTH: 2814
<212> TYPE: DNA
<213> ORGANISM: Artificial Sequence
<220> FEATURE:
<223> OTHER INFORMATION: Beta2M T02-TALEN - LEFT

<400> SEQUENCE: 84
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc acatcgttgc gttaagccaa cacccggcag cgttagggac cgtcgctgtc   240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca agattgcaaa acgtggcggc   420
gtgaccgcag tggaggcagt gcatgcatgg cgcaatgcac tgacgggtgc cccgctcaac   480
ttgaccccgg agcaggtggt ggccatcgcc agccacgatg gcggcaagca ggcgctggag   540
acggtccagc ggctgttgcc ggtgctgtgc caggcccacg gcttgacccc ggagcaggtg   600
gtggccatcg ccagccacga tggcggcaag caggcgctgg agacggtcca gcggctgttg   660
ccggtgctgt gccaggccca cggcttgacc ccggagcagg tggtggccat cgccagcaat   720
attggtggca agcaggcgct ggagacggtg caggcgctgt tgccggtgct gtgccaggcc   780
cacggcttga ccccgagca ggtggtggcc atcgccagca atattggtgg caagcaggcg   840
ctggagacgg tgcaggcgct gttgccggtg ctgtgccagg cccacggctt gaccccggag   900
caggtggtgg ccatcgccag caatattggt ggcaagcagg cgctggagac ggtgcaggcg   960
ctgttgccgg tgctgtgcca ggcccacggc ttgacccccc agcaggtggt ggccatcgcc  1020
agcaataatg gtggcaagca ggcgctggag acggtccagc ggctgttgcc ggtgctgtgc  1080
caggcccacg gcttgacccc ggagcaggtg gtggccatcg ccagcaatat tggtggcaag  1140
caggcgctgg agacggtgca ggcgctgttg ccggtgctgt gccaggccca cggcttgacc  1200
ccccagcagg tggtggccat cgccagcaat ggcggtggca agcaggcgct ggagacggtc  1260
cagcggctgt tgccggtgct gtgccaggcc cacggcttga ccccccagca ggtggtggcc  1320
atcgccagca atggcggtgg caagcaggcg ctggagacgg tccagcggct gttgccggtg  1380
ctgtgccagg cccacggctt gaccccggag caggtggtgg ccatcgccag ccacgatggc  1440
ggcaagcagg cgctggagac ggtccagcgg ctgttgccgg tgctgtgcca ggcccacggc  1500
ttgaccccgg agcaggtggt ggccatcgcc agcaatattg gtggcaagca ggcgctggag  1560
acggtgcagg cgctgttgcc ggtgctgtgc caggcccacg gcttgacccc ccagcaggtg  1620
gtggccatcg ccagcaataa tggtggcaag caggcgctgg agacggtcca gcggctgttg  1680
ccggtgctgt gccaggccca cggcttgacc ccccagcagg tggtggccat cgccagcaat  1740
aatggtggca agcaggcgct ggagacggtc cagcggctgt tgccggtgct gtgccaggcc  1800
cacggcttga ccccccagca ggtggtggcc atcgccagca atggcggtgg caagcaggcg  1860
```

```
ctggagacgg tccagcggct gttgccggtg ctgtgccagg cccacggctt gacccccag    1920 caggtggtgg ccatcgccag caatggcggt ggcaagcagg cgctggagac ggtccagcgg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca agctgaagta cgtgccccac    2280
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acgcgccat ctacaccgtg gcctccccca tcgactacgg cgtgatcgtg    2460
gacaccaagg cctactccgg cggctacaac ctgcccatcg ccaggccga cgaaatgcag    2520 aggtacgtgg aggagaacca gaccaggaac aagcacatca cccccaacga gtggtggaag    2580
gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gacccggag    2760 gaggtgagga ggaagttcaa caacggcgag atcaacttcg cggccgactg ataa         2814

<210> SEQ ID NO 85
<211> LENGTH: 2832
<212> TYPE: DNA
<213> ORGANISM: Artificial Sequence
<220> FEATURE:
<223> OTHER INFORMATION: Beta2M T02-TALEN RIGHT

<400> SEQUENCE: 85
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccg tcgctgtcaa gtatcaggac atgatcgcag cgttgccaga ggcgacacac     300
gaagcgatct tggcgtcgg caaacagtgg tccggcgcac gcgctctgga ggccttgctc     360
acggtggcgg gagagttgag aggtccaccg ttacagttgg acacaggcca acttctcaag     420
attgcaaaac gtggcggcgt gaccgcagtg gaggcagtgc atgcatggcg caatgcactg     480
acgggtgccc cgctcaactt gaccccccag caggtggtgg ccatcgccag caataatggt     540
ggcaagcagg cgctggagac ggtccagcgg ctgttgccgg tgctgtgcca ggcccacggc     600
ttgaccccgg agcaggtggt ggccatcgcc agcaatattg gtggcaagca ggcgctggag     660
acggtgcagg cgctgttgcc ggtgctgtgc caggcccacg gcttgacccc ggagcaggtg     720
gtggccatcg ccagccacga tggcggcaag caggcgctgg agacggtcca gcggctgttg     780
ccggtgctgt gccaggccca cggcttgacc cccagcaggt ggtggccat cgccagcaat     840 ggcggtggca agcaggcgct ggagacggtc agcggctgt tgccggtgct gtgccaggcc     900
cacggcttga ccccccagca ggtggtggcc atcgccagca atggcggtgg caagcaggcg     960
ctggagacgg tccagcggct gttgccggtg ctgtgccagg cccacggctt gacccccag    1020 caggtggtgg ccatcgccag caatggcggt ggcaagcagg cgctggagac ggtccagcgg    1080
```

```
ctgttgccgg tgctgtgcca ggcccacggc ttgaccccgg agcaggtggt ggccatcgcc    1140
agccacgatg gcggcaagca ggcgctggag acggtccagc ggctgttgcc ggtgctgtgc    1200
caggcccacg gcttgacccc ggagcaggtg gtggccatcg ccagccacga tggcggcaag    1260
caggcgctgg agacggtcca gcggctgttg ccggtgctgt gccaggccca cggcttgacc    1320
ccggagcagg tggtggccat cgccagcaat attggtggca agcaggcgct ggagacggtg    1380
caggcgctgt tgccggtgct gtgccaggcc acggcttga ccccccagca ggtggtggcc     1440
atcgccagca atggcggtgg caagcaggcg ctggagacgg tccagcggct gttgccggtg    1500
ctgtgccagg cccacggctt gaccccccag caggtggtgg ccatcgccag caatggcggt    1560
ggcaagcagg cgctggagac ggtccagcgg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ccagcaggtg    1740
gtggccatcg ccagcaatgg cggtggcaag caggcgctgg agacggtcca gcggctgttg    1800
ccggtgctgt gccaggccca cggcttgacc ccggagcagg tggtggccat cgccagccac    1860
gatggcggca agcaggcgct ggagacggtc agcggctgt tgccggtgct gtgccaggcc     1920
cacggcttga ccccccagca ggtggtggcc atcgccagca atggcggtgg caagcaggcg    1980
ctggagacgg tccagcggct gttgccggtg ctgtgccagg cccacggctt gaccctcag     2040 caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga atccgagtt gaggcacaag     2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgaca aaatgcagag gtacgtggag gagaaccaga ccaggaacaa gcacatcaac    2580
cccaacgagt ggtggaaggt gtaccctcc agcgtgaccg agttcaagtt cctgttcgtg     2640
tccggccact tcaagggcaa ctacaaggcc agctgacca ggctgaacca catcaccaac      2700
tgcaacggcg ccgtgctgtc cgtggaggag ctcctgatcg gcggcgagat gatcaaggcc    2760 ggcacccctga ccctggagga ggtgaggagg aagttcaaca cggcgagat caacttcgcg    2820 gccgactgat aa                                                        2832
```

<210> SEQ ID NO 86
<211> LENGTH: 47
<212> TYPE: DNA
<213> ORGANISM: Artificial Sequence
<220> FEATURE:
<223> OTHER INFORMATION: B2M T03- TALEN targeting sequence

<400> SEQUENCE: 86

```
ttagctgtgc tcgcgctact ctctctttct ggcctggagg ctatcca                  47
```

<210> SEQ ID NO 87
<211> LENGTH: 2814
<212> TYPE: DNA
<213> ORGANISM: Artificial Sequence
<220> FEATURE:
<223> OTHER INFORMATION: Beta2M T03-TALEN - LEFT

<400> SEQUENCE: 87

```
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa cacccggcag cgttagggac cgtcgctgtc     240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca agattgcaaa acgtggcggc     420
gtgaccgcag tggaggcagt gcatgcatgg cgcaatgcac tgacgggtgc cccgctcaac     480
ttgaccccgg agcaggtggt ggccatcgcc agcaatattg gtggcaagca ggcgctggag     540
acggtgcagg cgctgttgcc ggtgctgtgc caggcccacg gcttgacccc ccagcaggtg     600
gtggccatcg ccagcaataa tggtggcaag caggcgctgg agacggtcca gcggctgttg     660
ccggtgctgt gccaggccca cggcttgacc ccggagcagg tggtggccat cgccagccac     720
gatggcggca agcaggcgct ggagacggtc agcggctgt tgccggtgct gtgccaggcc     780
cacggcttga ccccccagca ggtggtggcc atcgccagca atggcggtgg caagcaggcg     840
ctggagacgg tccagcggct gttgccggtg ctgtgccagg cccacggctt gacccccag     900
caggtggtgg ccatcgccag caataatggt ggcaagcagg cgctggagac ggtccagcgg     960
ctgttgccgg tgctgtgcca ggcccacggc ttgacccccc agcaggtggt ggccatcgcc    1020
agcaatggcg gtggcaagca ggcgctggag acggtccagc ggctgttgcc ggtgctgtgc    1080
caggcccacg gcttgacccc ccagcaggtg gtggccatcg ccagcaataa tggtggcaag    1140
caggcgctgg agacggtcca gcggctgttg ccggtgctgt gccaggccca cggcttgacc    1200
ccggagcagg tggtggccat cgccagccac gatggcggca agcaggcgct ggagacggtc    1260
cagcggctgt tgccggtgct gtgccaggcc cacggcttga ccccccagca ggtggtggcc    1320
atcgccagca atggcggtgg caagcaggcg ctggagacgg tccagcggct gttgccggtg    1380
ctgtgccagg cccacggctt gaccccggag caggtggtgg ccatcgccag ccacgatggc    1440
ggcaagcagg cgctggagac ggtccagcgg ctgttgccgg tgctgtgcca ggcccacggc    1500
ttgaccccc agcaggtggt ggccatcgcc agcaataatg gtggcaagca ggcgctggag    1560
acggtccagc ggctgttgcc ggtgctgtgc caggcccacg gcttgacccc ggagcaggtg    1620
gtggccatcg ccagccacga tggcggcaag caggcgctgg agacggtcca gcggctgttg    1680
ccggtgctgt gccaggccca cggcttgacc cccagcagg tggtggccat cgccagcaat    1740
aatggtggca agcaggcgct ggagacggtc agcggctgt tgccggtgct gtgccaggcc    1800
cacggcttga ccccggagca ggtggtggcc atcgccagcc acgatggcgg caagcaggcg    1860
ctggagacgg tccagcggct gttgccggtg ctgtgccagg cccacggctt gacccccag    1920
caggtggtgg ccatcgccag caatggcggt ggcaagcagg cgctggagac ggtccagcgg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca agctgaagta cgtgccccac    2280
```

| | |
|---|---:|
| gagtacatcg agctgatcga gatcgcccgg aacagcaccc aggaccgtat cctggagatg | 2340 |
| aaggtgatgg agttcttcat gaaggtgtac ggctacaggg gcaagcacct gggcggctcc | 2400 |
| aggaagcccg acggcgccat ctacaccgtg gctcccccca tcgactacgg cgtgatcgtg | 2460 |
| gacaccaagg cctactccgg cggctacaac ctgcccatcg ccaggccga cgaaatgcag | 2520 |
| aggtacgtgg aggagaacca gaccaggaac aagcacatca accccaacga gtggtggaag | 2580 |
| gtgtacccct ccagcgtgac cgagttcaag ttcctgttcg tgtccggcca cttcaagggc | 2640 |
| aactacaagg cccagctgac caggctgaac cacatcacca actgcaacgg cgccgtgctg | 2700 |
| tccgtggagg agctcctgat cggcggcgag atgatcaagg ccggcaccct gaccctggag | 2760 |
| gaggtgagga ggaagttcaa caacggcgag atcaacttcg cggccgactg ataa | 2814 |

<210> SEQ ID NO 88
<211> LENGTH: 2832
<212> TYPE: DNA
<213> ORGANISM: Artificial Sequence
<220> FEATURE:
<223> OTHER INFORMATION: Beta2M T03-TALEN -RIGHT

<400> SEQUENCE: 88

| | |
|---|---:|
| atgggcgatc taaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |
| ttagggaccc tcgctgtcaa gtatcaggac atgatcgcac cgttgccaga ggcgacacac | 300 |
| gaagcgatcg ttggcgtcgg caaacagtgg tccggcgcac gcgctctgga ggccttgctc | 360 |
| acggtggcgg gagagttgag aggtccaccg ttacagttgg acacaggcca acttctcaag | 420 |
| attgcaaaac gtggcggcgt gaccgcagtg gaggcagtgc atgcatggcg caatgcactg | 480 |
| acgggtgccc cgctcaactt gacccccag caggtggtgg ccatcgccag caataatggt | 540 |
| ggcaagcagg cgctggagac ggtccagcgg ctgttgccgg tgctgtgcca ggcccacggc | 600 |
| ttgaccccc agcaggtggt ggccatcgcc agcaataatg gtggcaagca ggcgctggag | 660 |
| acggtccagc ggctgttgcc ggtgctgtgc caggcccacg gcttgacccc ggagcaggtg | 720 |
| gtggccatcg ccagcaatat tggtggcaag caggcgctgg agacggtgca ggcgctgttg | 780 |
| ccggtgctgt gccaggccca cggcttgacc ccccagcagg tggtggccat cgccagcaat | 840 |
| ggcggtggca agcaggcgct ggagacggtc agcggctgt tgccggtgct gtgccaggcc | 900 |
| cacggcttga ccccggagca ggtggtggcc atcgccagca atattggtgg caagcaggcg | 960 |
| ctggagacgg tgcaggcgct gttgccggtg ctgtgccagg cccacggctt gacccccag | 1020 |
| caggtggtgg ccatcgccag caataatggt ggcaagcagg cgctggagac ggtccagcgg | 1080 |
| ctgttgccgg tgctgtgcca ggcccacggc ttgaccccgg agcaggtggt ggccatcgcc | 1140 |
| agccacgatg gcggcaagca ggcgctggag acggtccagc ggctgttgcc ggtgctgtgc | 1200 |
| caggcccacg gcttgacccc ggagcaggtg gtggccatcg ccagccacga tggcggcaag | 1260 |
| caggcgctgg agacggtcca gcggctgttg ccggtgctgt gccaggccca cggcttgacc | 1320 |
| ccccagcagg tggtggccat cgccagcaat ggcggtggca agcaggcgct ggagacggtc | 1380 |
| cagcggctgt tgccggtgct gtgccaggcc cacggcttga ccccggagca ggtggtggcc | 1440 |
| atcgccagcc acgatggcgg caagcaggcg ctggagacgg tccagcggct gttgccggtg | 1500 |
| ctgtgccagg cccacggctt gaccccggag caggtggtgg ccatcgccag ccacgatggc | 1560 |

```
ggcaagcagg cgctggagac ggtccagcgg ctgttgccgg tgctgtgcca ggcccacggc  1620
ttgaccccgg agcaggtggt ggccatcgcc agcaatattg gtggcaagca ggcgctggag  1680
acggtgcagg cgctgttgcc ggtgctgtgc caggcccacg gcttgacccc ccagcaggtg  1740
gtggccatcg ccagcaataa tggtggcaag caggcgctgg agacggtcca gcggctgttg  1800
ccggtgctgt gccaggccca cggcttgacc cccagcagg tggtggccat cgccagcaat  1860
aatggtggca agcaggcgct ggagacggtc agcggctgt gccggtgct gtgccaggcc  1920 cacggcttga ccccggagca ggtggtggcc atcgccagcc acgatggcgg caagcaggcg  1980
ctggagacgg tccagcggct gttgccggtg ctgtgccagg cccacggctt gacccctcag  2040
caggtggtgg ccatcgccag caatggcggc ggcaggccgg cgctggagag cattgttgcc  2100
cagttatctc gccctgatcc ggcgttggcc gcgttgacca acgaccacct cgtcgccttg  2160
gcctgcctcg gcgggcgtcc tgcgctggat gcagtgaaaa agggattggg ggatcctatc  2220
agccgttccc agctggtgaa gtccgagctg gaggagaaga atccgagtt gaggcacaag  2280 ctgaagtacg tgccccacga gtacatcgag ctgatcgaga tcgcccggaa cagcacccag  2340
gaccgtatcc tggagatgaa ggtgatggag ttcttcatga aggtgtacgg ctacaggggc  2400
aagcacctgg gcggctccag gaagcccgac ggcgccatct acaccgtggg ctcccccatc  2460
gactacggcg tgatcgtgga caccaaggcc tactccggcg gctacaacct gcccatcggc  2520
caggccgacg aaatgcagag gtacgtggag gagaaccaga ccaggaacaa gcacatcaac  2580
cccaacgagt ggtggaaggt gtaccccctcc agcgtgaccg agttcaagtt cctgttcgtg  2640
tccggccact tcaagggcaa ctacaaggcc agctgacca ggctgaacca catcaccaac  2700
tgcaacggcg ccgtgctgtc cgtggaggag ctcctgatcg gcggcgagat gatcaaggcc  2760
ggcaccctga ccctggagga ggtgaggagg aagttcaaca cggcgagat caacttcgcg  2820 gccgactgat aa                                                      2832
```

<210> SEQ ID NO 89
<211> LENGTH: 526
<212> TYPE: PRT
<213> ORGANISM: Artificial Sequence
<220> FEATURE:
<223> OTHER INFORMATION: Chimeric B2M-UL18

<400> SEQUENCE: 89

```
Met Ala Leu Pro Val Thr Ala Leu Leu Leu Pro Leu Ala Leu Leu Leu
1               5                   10                  15

His Ala Ala Arg Pro Ser Arg Ser Val Ala Leu Ala Val Leu Ala Leu
            20                  25                  30

Leu Ser Leu Ser Gly Leu Glu Ala Ile Gln Arg Thr Pro Lys Ile Gln
        35                  40                  45

Val Tyr Ser Arg His Pro Ala Glu Asn Gly Lys Ser Asn Phe Leu Asn
    50                  55                  60

Cys Tyr Val Ser Gly Phe His Pro Ser Asp Ile Glu Val Asp Leu Leu
65                  70                  75                  80

Lys Asn Gly Glu Arg Ile Glu Lys Val Glu His Ser Asp Leu Ser Phe
                85                  90                  95

Ser Lys Asp Trp Ser Phe Tyr Leu Leu Tyr Tyr Thr Glu Phe Thr Pro
            100                 105                 110

Thr Glu Lys Asp Glu Tyr Ala Cys Arg Val Asn His Val Thr Leu Ser
        115                 120                 125
```

```
Gln Pro Lys Ile Val Lys Trp Asp Arg Asp Met Gly Gly Gly Ser
130                 135                 140

Gly Gly Gly Gly Ser Gly Gly Gly Ser Gly Gly Gly Ser Met
145                 150                 155                 160

Thr Met Trp Cys Leu Thr Leu Phe Val Leu Trp Met Leu Arg Val Val
                165                 170                 175

Gly Met His Val Leu Arg Tyr Gly Tyr Thr Gly Ile Phe Asp Asp Thr
                180                 185                 190

Ser His Met Thr Leu Thr Val Val Gly Ile Phe Asp Gly Gln His Phe
                195                 200                 205

Phe Thr Tyr His Val Asn Ser Ser Asp Lys Ala Ser Ser Arg Ala Asn
210                 215                 220

Gly Thr Ile Ser Trp Met Ala Asn Val Ser Ala Ala Tyr Pro Thr Tyr
225                 230                 235                 240

Leu Asp Gly Glu Arg Ala Lys Gly Asp Leu Ile Phe Asn Gln Thr Glu
                245                 250                 255

Gln Asn Leu Leu Glu Leu Glu Ile Ala Leu Gly Tyr Arg Ser Gln Ser
                260                 265                 270

Val Leu Thr Trp Thr His Glu Cys Asn Thr Thr Glu Asn Gly Ser Phe
                275                 280                 285

Val Ala Gly Tyr Glu Gly Phe Gly Trp Asp Gly Glu Thr Leu Met Glu
290                 295                 300

Leu Lys Asp Asn Leu Thr Leu Trp Thr Gly Pro Asn Tyr Glu Ile Ser
305                 310                 315                 320

Trp Leu Lys Gln Asn Lys Thr Tyr Ile Asp Gly Lys Ile Lys Asn Ile
                325                 330                 335

Ser Glu Gly Asp Thr Thr Ile Gln Arg Asn Tyr Leu Lys Gly Asn Cys
                340                 345                 350

Thr Gln Trp Ser Val Ile Tyr Ser Gly Phe Gln Thr Pro Val Thr His
                355                 360                 365

Pro Val Val Lys Gly Gly Val Arg Asn Gln Asn Asp Asn Arg Ala Glu
                370                 375                 380

Ala Phe Cys Thr Ser Tyr Gly Phe Phe Pro Gly Glu Ile Asn Ile Thr
385                 390                 395                 400

Phe Ile His Tyr Gly Asn Lys Ala Pro Asp Asp Ser Glu Pro Gln Cys
                405                 410                 415

Asn Pro Leu Leu Pro Thr Phe Asp Gly Thr Phe His Gln Gly Cys Tyr
                420                 425                 430

Val Ala Ile Phe Cys Asn Gln Asn Tyr Thr Cys Arg Val Thr His Gly
                435                 440                 445

Asn Trp Thr Val Glu Ile Pro Ile Ser Val Thr Ser Pro Asp Asp Ser
450                 455                 460

Ser Ser Gly Glu Val Pro Asp His Pro Thr Ala Asn Lys Arg Tyr Asn
465                 470                 475                 480

Thr Met Thr Ile Ser Ser Val Leu Leu Ala Leu Leu Leu Cys Ala Leu
                485                 490                 495

Leu Phe Ala Phe Leu His Tyr Phe Thr Thr Leu Lys Gln Tyr Leu Arg
                500                 505                 510

Asn Leu Ala Phe Ala Trp Arg Tyr Arg Lys Val Arg Ser Ser
                515                 520                 525

<210> SEQ ID NO 90
<211> LENGTH: 310
<212> TYPE: PRT
```

<213> ORGANISM: Artificial Sequence
<220> FEATURE:
<223> OTHER INFORMATION: SP-MICAed

<400> SEQUENCE: 90

```
Met Gly Gly Val Leu Leu Thr Gln Arg Thr Leu Leu Ser Leu Val Leu
1               5                   10                  15

Ala Leu Leu Phe Pro Ser Met Ala Ser Met Glu Pro His Ser Leu Arg
            20                  25                  30

Tyr Asn Leu Thr Val Leu Ser Trp Asp Gly Ser Val Gln Ser Gly Phe
        35                  40                  45

Leu Thr Glu Val His Leu Asp Gly Gln Pro Phe Leu Arg Cys Asp Arg
    50                  55                  60

Gln Lys Cys Arg Ala Lys Pro Gln Gly Gln Trp Ala Glu Asp Val Leu
65                  70                  75                  80

Gly Asn Lys Thr Trp Asp Arg Glu Thr Arg Asp Leu Thr Gly Asn Gly
                85                  90                  95

Lys Asp Leu Arg Met Thr Leu Ala His Ile Lys Asp Gln Lys Glu Gly
            100                 105                 110

Leu His Ser Leu Gln Glu Ile Arg Val Cys Glu Ile His Glu Asp Asn
        115                 120                 125

Ser Thr Arg Ser Ser Gln His Phe Tyr Tyr Asp Gly Glu Leu Phe Leu
    130                 135                 140

Ser Gln Asn Leu Glu Thr Lys Glu Trp Thr Met Pro Gln Ser Ser Arg
145                 150                 155                 160

Ala Gln Thr Leu Ala Met Asn Val Arg Asn Phe Leu Lys Glu Asp Ala
                165                 170                 175

Met Lys Thr Lys Thr His Tyr His Ala Met His Ala Asp Cys Leu Gln
            180                 185                 190

Glu Leu Arg Arg Tyr Leu Lys Ser Gly Val Val Leu Arg Arg Thr Val
        195                 200                 205

Pro Pro Met Val Asn Val Thr Arg Ser Glu Ala Ser Glu Gly Asn Ile
    210                 215                 220

Thr Val Thr Cys Arg Ala Ser Gly Phe Tyr Pro Trp Asn Ile Thr Leu
225                 230                 235                 240

Ser Trp Arg Gln Asp Gly Val Ser Leu Ser His Asp Thr Gln Gln Trp
                245                 250                 255

Gly Asp Val Leu Pro Asp Gly Asn Gly Thr Tyr Gln Thr Trp Val Ala
            260                 265                 270

Thr Arg Ile Cys Gln Gly Glu Glu Gln Arg Phe Thr Cys Tyr Met Glu
        275                 280                 285

His Ser Gly Asn His Ser Thr His Pro Val Pro Ser Gly Lys Val Leu
    290                 295                 300

Val Leu Gln Ser His Trp
305                 310
```

<210> SEQ ID NO 91
<211> LENGTH: 313
<212> TYPE: PRT
<213> ORGANISM: Artificial Sequence
<220> FEATURE:
<223> OTHER INFORMATION: SP-MICBed

<400> SEQUENCE: 91

```
Met Gly Gly Val Leu Leu Thr Gln Arg Thr Leu Leu Ser Leu Val Leu
1               5                   10                  15
```

```
Ala Leu Leu Phe Pro Ser Met Ala Ser Met Ala Glu Pro His Ser Leu
            20                  25                  30

Arg Tyr Asn Leu Met Val Leu Ser Gln Asp Glu Ser Val Gln Ser Gly
            35                  40                  45

Phe Leu Ala Glu Gly His Leu Asp Gly Gln Pro Phe Leu Arg Tyr Asp
50                      55                  60

Arg Gln Lys Arg Ala Lys Pro Gln Gly Gln Trp Ala Glu Asp Val
65                  70                  75                  80

Leu Gly Ala Lys Thr Trp Asp Thr Glu Thr Asp Leu Thr Glu Asn
                85                  90                  95

Gly Gln Asp Leu Arg Arg Thr Leu Thr His Ile Lys Asp Gln Lys Gly
                100                 105                 110

Gly Leu His Ser Leu Gln Glu Ile Arg Val Cys Glu Ile His Glu Asp
            115                 120                 125

Ser Ser Thr Arg Gly Ser Arg His Phe Tyr Tyr Asp Gly Glu Leu Phe
130                 135                 140

Leu Ser Gln Asn Leu Glu Thr Gln Glu Ser Thr Val Pro Gln Ser Ser
145                 150                 155                 160

Arg Ala Gln Thr Leu Ala Met Asn Val Thr Asn Phe Trp Lys Glu Asp
                165                 170                 175

Ala Met Lys Thr Lys Thr His Tyr Arg Ala Met Gln Ala Asp Cys Leu
            180                 185                 190

Gln Lys Leu Gln Arg Tyr Leu Lys Ser Gly Val Ala Ile Arg Arg Thr
        195                 200                 205

Val Pro Pro Met Val Asn Val Thr Cys Ser Glu Val Ser Glu Gly Asn
210                 215                 220

Ile Thr Val Thr Cys Arg Ala Ser Ser Phe Tyr Pro Arg Asn Ile Thr
225                 230                 235                 240

Leu Thr Trp Arg Gln Asp Gly Val Ser Leu Ser His Asn Thr Gln Gln
                245                 250                 255

Trp Gly Asp Val Leu Pro Asp Gly Asn Gly Thr Tyr Gln Thr Trp Val
            260                 265                 270

Ala Thr Arg Ile Arg Gln Gly Glu Glu Gln Arg Phe Thr Cys Tyr Met
        275                 280                 285

Glu His Ser Gly Asn His Gly Thr His Pro Val Pro Ser Gly Lys Val
    290                 295                 300

Leu Val Leu Gln Ser Gln Arg Thr Asp
305                 310

<210> SEQ ID NO 92
<211> LENGTH: 209
<212> TYPE: PRT
<213> ORGANISM: Artificial Sequence
<220> FEATURE:
<223> OTHER INFORMATION: SP-ULBP1ed

<400> SEQUENCE: 92

Met Gly Gly Val Leu Leu Thr Gln Arg Thr Leu Leu Ser Leu Val Leu
1               5                   10                  15

Ala Leu Leu Phe Pro Ser Met Ala Ser Met Gly Trp Val Asp Thr His
            20                  25                  30

Cys Leu Cys Tyr Asp Phe Ile Ile Thr Pro Lys Ser Arg Pro Glu Pro
            35                  40                  45

Gln Trp Cys Glu Val Gln Gly Leu Val Asp Glu Arg Pro Phe Leu His
50                  55                  60
```

Tyr Asp Cys Val Asn His Lys Ala Lys Ala Phe Ser Leu Gly Lys
65                  70                  75                  80

Lys Val Asn Val Thr Lys Thr Trp Glu Glu Gln Thr Glu Thr Leu Arg
                85                  90                  95

Asp Val Val Asp Phe Leu Lys Gly Gln Leu Leu Asp Ile Gln Val Glu
            100                 105                 110

Asn Leu Ile Pro Ile Glu Pro Leu Thr Leu Gln Ala Arg Met Ser Cys
            115                 120                 125

Glu His Glu Ala His Gly His Gly Arg Gly Ser Trp Gln Phe Leu Phe
        130                 135                 140

Asn Gly Gln Lys Phe Leu Leu Phe Asp Ser Asn Asn Arg Lys Trp Thr
145                 150                 155                 160

Ala Leu His Pro Gly Ala Lys Lys Met Thr Glu Lys Trp Glu Lys Asn
                165                 170                 175

Arg Asp Val Thr Met Phe Phe Gln Lys Ile Ser Leu Gly Asp Cys Lys
            180                 185                 190

Met Trp Leu Glu Glu Phe Leu Met Tyr Trp Glu Gln Met Leu Asp Pro
            195                 200                 205

Thr

<210> SEQ ID NO 93
<211> LENGTH: 211
<212> TYPE: PRT
<213> ORGANISM: Artificial Sequence
<220> FEATURE:
<223> OTHER INFORMATION: SP-ULBP2ed

<400> SEQUENCE: 93

Met Gly Gly Val Leu Leu Thr Gln Arg Thr Leu Leu Ser Leu Val Leu
1               5                   10                  15

Ala Leu Leu Phe Pro Ser Met Ala Ser Met Gly Arg Ala Asp Pro His
                20                  25                  30

Ser Leu Cys Tyr Asp Ile Thr Val Ile Pro Lys Phe Arg Pro Gly Pro
            35                  40                  45

Arg Trp Cys Ala Val Gln Gly Gln Val Asp Glu Lys Thr Phe Leu His
    50                  55                  60

Tyr Asp Cys Gly Asn Lys Thr Val Thr Pro Val Ser Pro Leu Gly Lys
65                  70                  75                  80

Lys Leu Asn Val Thr Thr Ala Trp Lys Ala Gln Asn Pro Val Leu Arg
                85                  90                  95

Glu Val Val Asp Ile Leu Thr Glu Gln Leu Arg Asp Ile Gln Leu Glu
            100                 105                 110

Asn Tyr Thr Pro Lys Glu Pro Leu Thr Leu Gln Ala Arg Met Ser Cys
            115                 120                 125

Glu Gln Lys Ala Glu Gly His Ser Ser Gly Ser Trp Gln Phe Ser Phe
        130                 135                 140

Asp Gly Gln Ile Phe Leu Leu Phe Asp Ser Glu Lys Arg Met Trp Thr
145                 150                 155                 160

Thr Val His Pro Gly Ala Arg Lys Met Lys Glu Lys Trp Glu Asn Asp
                165                 170                 175

Lys Val Val Ala Met Ser Phe His Tyr Phe Ser Met Gly Asp Cys Ile
            180                 185                 190

Gly Trp Leu Glu Asp Phe Leu Met Gly Met Asp Ser Thr Leu Glu Pro
            195                 200                 205

Ser Ala Gly

<210> SEQ ID NO 94
<211> LENGTH: 206
<212> TYPE: PRT
<213> ORGANISM: Artificial Sequence
<220> FEATURE:
<223> OTHER INFORMATION: SP-ULBP3ed

<400> SEQUENCE: 94

```
Met Gly Gly Val Leu Leu Thr Gln Arg Thr Leu Leu Ser Leu Val Leu
1               5                   10                  15

Ala Leu Leu Phe Pro Ser Met Ala Ser Met Asp Ala His Ser Leu Trp
            20                  25                  30

Tyr Asn Phe Thr Ile Ile His Leu Pro Arg His Gly Gln Gln Trp Cys
        35                  40                  45

Glu Val Gln Ser Gln Val Asp Gln Lys Asn Phe Leu Ser Tyr Asp Cys
    50                  55                  60

Gly Ser Asp Lys Val Leu Ser Met Gly His Leu Glu Glu Gln Leu Tyr
65                  70                  75                  80

Ala Thr Asp Ala Trp Gly Lys Gln Leu Glu Met Leu Arg Glu Val Gly
                85                  90                  95

Gln Arg Leu Arg Leu Glu Leu Ala Asp Thr Glu Leu Glu Asp Phe Thr
            100                 105                 110

Pro Ser Gly Pro Leu Thr Leu Gln Val Arg Met Ser Cys Glu Cys Glu
        115                 120                 125

Ala Asp Gly Tyr Ile Arg Gly Ser Trp Gln Phe Ser Phe Asp Gly Arg
    130                 135                 140

Lys Phe Leu Leu Phe Asp Ser Asn Asn Arg Lys Trp Thr Val Val His
145                 150                 155                 160

Ala Gly Ala Arg Arg Met Lys Glu Lys Trp Glu Lys Asp Ser Gly Leu
                165                 170                 175

Thr Thr Phe Phe Lys Met Val Ser Met Arg Asp Cys Lys Ser Trp Leu
            180                 185                 190

Arg Asp Phe Leu Met His Arg Lys Lys Arg Leu Glu Pro Thr
        195                 200                 205
```

<210> SEQ ID NO 95
<211> LENGTH: 221
<212> TYPE: PRT
<213> ORGANISM: Artificial Sequence
<220> FEATURE:
<223> OTHER INFORMATION: SP-N2DL4ed

<400> SEQUENCE: 95

```
Met Gly Gly Val Leu Leu Thr Gln Arg Thr Leu Leu Ser Leu Val Leu
1               5                   10                  15

Ala Leu Leu Phe Pro Ser Met Ala Ser Met His Ser Leu Cys Phe Asn
            20                  25                  30

Phe Thr Ile Lys Ser Leu Ser Arg Pro Gly Gln Pro Trp Cys Glu Ala
        35                  40                  45

Gln Val Phe Leu Asn Lys Asn Leu Phe Leu Gln Tyr Asn Ser Asp Asn
    50                  55                  60

Asn Met Val Lys Pro Leu Gly Leu Leu Gly Lys Lys Val Tyr Ala Thr
65                  70                  75                  80

Ser Thr Trp Gly Glu Leu Thr Gln Thr Leu Gly Glu Val Gly Arg Asp
                85                  90                  95
```

```
Leu Arg Met Leu Leu Cys Asp Ile Lys Pro Gln Ile Lys Thr Ser Asp
            100                 105                 110

Pro Ser Thr Leu Gln Val Glu Met Phe Cys Gln Arg Glu Ala Glu Arg
        115                 120                 125

Cys Thr Gly Ala Ser Trp Gln Phe Ala Thr Asn Gly Glu Lys Ser Leu
    130                 135                 140

Leu Phe Asp Ala Met Asn Met Thr Trp Thr Val Ile Asn His Glu Ala
145                 150                 155                 160

Ser Lys Ile Lys Glu Thr Trp Lys Lys Asp Arg Gly Leu Glu Lys Tyr
                165                 170                 175

Phe Arg Lys Leu Ser Lys Gly Asp Cys Asp His Trp Leu Arg Glu Phe
            180                 185                 190

Leu Gly His Trp Glu Ala Met Pro Glu Pro Thr Val Ser Pro Val Asn
        195                 200                 205

Ala Ser Asp Ile His Trp Ser Ser Ser Leu Pro Asp
    210                 215                 220

<210> SEQ ID NO 96
<211> LENGTH: 224
<212> TYPE: PRT
<213> ORGANISM: Artificial Sequence
<220> FEATURE:
<223> OTHER INFORMATION: SP-RET1Ged

<400> SEQUENCE: 96

Met Gly Gly Val Leu Leu Thr Gln Arg Thr Leu Leu Ser Leu Val Leu
1               5                   10                  15

Ala Leu Leu Phe Pro Ser Met Ala Ser Met Gly Leu Ala Asp Pro His
            20                  25                  30

Ser Leu Cys Tyr Asp Ile Thr Val Ile Pro Lys Phe Arg Pro Gly Pro
        35                  40                  45

Arg Trp Cys Ala Val Gln Gly Gln Val Asp Glu Lys Thr Phe Leu His
    50                  55                  60

Tyr Asp Cys Gly Ser Lys Thr Val Thr Pro Val Ser Pro Leu Gly Lys
65                  70                  75                  80

Lys Leu Asn Val Thr Thr Ala Trp Lys Ala Gln Asn Pro Val Leu Arg
                85                  90                  95

Glu Val Val Asp Ile Leu Thr Glu Gln Leu Leu Asp Ile Gln Leu Glu
            100                 105                 110

Asn Tyr Ile Pro Lys Glu Pro Leu Thr Leu Gln Ala Arg Met Ser Cys
        115                 120                 125

Glu Gln Lys Ala Glu Gly His Gly Ser Gly Ser Trp Gln Leu Ser Phe
    130                 135                 140

Asp Gly Gln Ile Phe Leu Leu Phe Asp Ser Glu Asn Arg Met Trp Thr
145                 150                 155                 160

Thr Val His Pro Gly Ala Arg Lys Met Lys Glu Lys Trp Glu Asn Asp
                165                 170                 175

Lys Asp Met Thr Met Ser Phe His Tyr Ile Ser Met Gly Asp Cys Thr
            180                 185                 190

Gly Trp Leu Glu Asp Phe Leu Met Gly Met Asp Ser Thr Leu Glu Pro
        195                 200                 205

Ser Ala Gly Ala Pro Pro Thr Met Ser Ser Gly Thr Ala Gln Pro Arg
    210                 215                 220

<210> SEQ ID NO 97
<211> LENGTH: 211
```

```
<212> TYPE: PRT
<213> ORGANISM: Artificial Sequence
<220> FEATURE:
<223> OTHER INFORMATION: SP-RAETILed

<400> SEQUENCE: 97

Met Gly Gly Val Leu Leu Thr Gln Arg Thr Leu Leu Ser Leu Val Leu
1               5                   10                  15

Ala Leu Leu Phe Pro Ser Met Ala Ser Met Arg Arg Asp Asp Pro His
            20                  25                  30

Ser Leu Cys Tyr Asp Ile Thr Val Ile Pro Lys Phe Arg Pro Gly Pro
            35                  40                  45

Arg Trp Cys Ala Val Gln Gly Gln Val Asp Glu Lys Thr Phe Leu His
    50                  55                  60

Tyr Asp Cys Gly Asn Lys Thr Val Thr Pro Val Ser Pro Leu Gly Lys
65                  70                  75                  80

Lys Leu Asn Val Thr Met Ala Trp Lys Ala Gln Asn Pro Val Leu Arg
                85                  90                  95

Glu Val Val Asp Ile Leu Thr Glu Gln Leu Leu Asp Ile Gln Leu Glu
            100                 105                 110

Asn Tyr Thr Pro Lys Glu Pro Leu Thr Leu Gln Ala Arg Met Ser Cys
        115                 120                 125

Glu Gln Lys Ala Glu Gly His Ser Ser Gly Ser Trp Gln Phe Ser Ile
    130                 135                 140

Asp Gly Gln Thr Phe Leu Leu Phe Asp Ser Glu Lys Arg Met Trp Thr
145                 150                 155                 160

Thr Val His Pro Gly Ala Arg Lys Met Lys Glu Lys Trp Glu Asn Asp
                165                 170                 175

Lys Asp Val Ala Met Ser Phe His Tyr Ile Ser Met Gly Asp Cys Ile
            180                 185                 190

Gly Trp Leu Glu Asp Phe Leu Met Gly Met Asp Ser Thr Leu Glu Pro
        195                 200                 205

Ser Ala Gly
    210
```

METHOD FOR GENERATING T-CELLS COMPATIBLE FOR ALLOGENIC TRANSPLANTATION

FIELD OF THE INVENTION

The present invention pertains to engineered T-cells, method for their preparation and their use as medicament, particularly for immunotherapy. The engineered T-cells of the invention are characterized in that the expression of beta 2-microglobulin (B2M) and/or class II major histocompatibility complex transactivator (CIITA) is inhibited, e.g., by using rare-cutting endonucleases able to selectively inactivating by DNA cleavage the gene encoding B2M and/or CIITA, or by using nucleic acid molecules which inhibit the expression of B2M and/or CIITA. In order to further render the T-cell non-alloreactive, at least one gene encoding a component of the T-cell receptor is inactivated, e.g., by using a rare-cutting endonucleases able to selectively inactivating by DNA cleavage the gene encoding said TCR component. In addition, a step of expression of immunosuppressive polypeptide such as viral MHCI homolog or NKG2D ligand can be performed on those modified T-cells in order to prolong the survival of these modified T cells in host organism. Such modified T-cell is particularly suitable for allogeneic transplantations, especially because it reduces both the risk of rejection by the host's immune system and the risk of developing graft versus host disease. The invention opens the way to standard and affordable adoptive immunotherapy strategies using T-Cells for treating cancer, infections and auto-immune diseases.

BACKGROUND OF THE INVENTION

Adoptive immunotherapy, which involves the transfer of autologous antigen-specific T-cells generated ex vivo, is a promising strategy to treat viral infections and cancer. The T-cells used for adoptive immunotherapy can be generated either by expansion of antigen-specific T-cells or redirection of T-cells through genetic engineering (Park, Rosenberg et al. 2011).

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T-cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors (Jena, Dotti et al. 2010).

The current protocol for treatment of patients using adoptive immunotherapy is based on autologous cell transfer. In this approach, T lymphocytes are recovered from patients, genetically modified or selected ex vivo, cultivated in vitro in order to amplify the number of cells if necessary and finally infused into the patient. In addition to lymphocyte infusion, the host may be manipulated in other ways that support the engraftment of the T cells or their participation in an immune response, for example pre-conditioning (with radiation or chemotherapy) and administration of lymphocyte growth factors (such as IL-2). Each patient receives an individually fabricated treatment, using the patient's own lymphocytes (i.e. an autologous therapy). Autologous therapies face substantial technical and logistic hurdles to practical application, their generation requires expensive dedicated facilities and expert personnel, they must be generated in a short time following a patient's diagnosis, and in many cases, pretreatment of the patient has resulted in degraded immune function, such that the patient's lymphocytes may be poorly functional and present in very low numbers. Because of these hurdles, each patient's autologous cell preparation is effectively a new product, resulting in substantial variations in efficacy and safety.

Ideally, one would like to use a standardized therapy in which allogeneic therapeutic cells could be pre-manufactured, characterized in detail, and available for immediate administration to patients. By allogeneic it is meant that the cells are obtained from individuals belonging to the same species but are genetically dissimilar. However, the use of allogeneic cells presently has many drawbacks. In immune-competent hosts allogeneic cells are rapidly rejected, a process termed host versus graft rejection (HvG), and this substantially limits the efficacy of the transferred cells. In immune-incompetent hosts, allogeneic cells are able to engraft, but their endogenous T-cell receptors (TCR) specificities may recognize the host tissue as foreign, resulting in graft versus host disease (GvHD), which can lead to serious tissue damage and death.

In order to provide allogeneic T-cells, the inventors previously disclosed a method to genetically engineer T-Cells, in which different effector genes, in particular those encoding T-cell receptors, were inactivated by using specific TAL-nucleases, better known under the trade mark TALEN™ (Cellectis, 8, rue de la Croix Jarry, 75013 PARIS). This method has proven to be highly efficient in primary cells using RNA transfection as part of a platform allowing the mass production of allogeneic T-cells (WO 2013/176915).

Beta-2 microglobulin, also known as B2M, is the light chain of MHC class I molecules, and as such an integral part of the major histocompatibility complex In human, B2M is encoded by the b2m gene which is located on chromosome 15, opposed to the other MHC genes which are located as gene cluster on chromosome 6. The human protein is composed of 119 amino acids (SEQ ID NO: 1) and has a molecular weight of 11.800 Daltons. Mice models deficient for beta-2 microglobulin have shown that B2M is necessary for cell surface expression of MHC class I and stability of the peptide binding groove. It was further shown that haemopoietic transplants from mice that are deficient for normal cell-surface MHC I expression are rejected by NK1.1+ cells in normal mice because of a targeted mutation in the beta-2 micorglobulin gene, suggesting that deficient expression of MHC I molecules renders marrow cells susceptible to rejection by the host immune system (Bix et al. 1991).

CIITA protein (SEQ ID NO: 4—NCBI Reference Sequence: NP_000237.2) that acts as a positive regulator of class II major histocompatibility complex gene transcription, including β2m gene transcription, and is often referred to as the "master control factor" for the expression of these genes. CIITA mRNA (SEQ ID NO: 5) can only be detected in human leukocyte antigen (HLA) system class II-positive cell lines and tissues. This highly restricted tissue distribution suggests that expression of HLA class II genes is to a large extent under the control of CIITA (Mach B., et al. 1994).

Adaptive immune response is a complex biological system where numerous cellular components interact. Professional Antigen Presenting Cells (APC) are able to process foreign bodies and expose them to helper T cells in the context of MHC Class II molecules. Activated helper T cells will in turn stimulate B cells response and cytotoxic T (CTL) cells response. CTL recognize foreign peptides presented by MHC Class I molecules but in the case of alloreactivity, recognize and kill cells bearing foreign MHC Class I. MHC Class I molecules are composed of 2 entities: the highly polymorphic, transmembrane heavy chain and a small invariant polypeptide, the beta2-microglobuline (beta2-m) encoded by B2M gene. The expression of the MHC Class I heavy chain at the cell surface requires its association with the beta2-m. Hence, abrogation of beta2-m expression in CAR T cells will impair MHC Class I expression and make them invisible to host CTL However, MHC Class I deficient CAR T cells are susceptible to lysis by host NK cells, which target cells lacking MHC Class I molecules [Ljunggren H G et al. (1990), Immunl Today. 11:237-244].

NK cells exert cytotoxic functions towards the cells they interact with based on the balance between activating and inhibitory signals they received through different monomorphic or polymorphic receptors. One central activating receptor on human NK cells is NKG2D and its ligands include proteins such as MICA, MICB, ULBP1, ULBP2, ULBP3 [Raulet D H, (2003), Nature Reviews Immunology 3 (10): 781-79]. On the other hand, the inhibitory signal is mediated through the interaction between NK receptors like LIR-1/ILT2 and MHC Class I molecules [Ljunggren H G et al. (1990), Immunl Today. 11:237-244]. Some viruses such as cytomegaloviruses have aquired mechanisms to avoid NK cell mediate immune surveillance. HCMV genome encodes proteins that are able to prevent MHC ClassI surface expression (i.e. US2, US3, US6 and US11) while expressing a MHC classI homolog protein (UL18) that acts as a decoy to block NK-mediated cell lysis [Kim, Y et al. (2008), PLOS Pathogens. 4: e1000123, and Wilkinson G. et al. (2010). J Clin Virol. 41(3):206-212]. Moreover, HCMV interferes with the NKG2D pathway by secreting a protein able to bind NKG2D ligands and prevent their surface expression [Welte S A et al. (2003), Eur J Immunol 33 (1): 194-203]. In tumor cells, some mechanisms have evolved to evade NKG2D response by secreting NKG2D ligands such as ULBP2, MICB or MICA (Waldhauer I, Steinle A (2003). Proteolytic release of soluble UL16-binding protein 2 from tumor cells. Cancer Res 2006; 66(5): 2520-2526; Salih H R et al. (2006), Hum Immunol. 2006 March; 67(3):188-95; Salih H R et al. (2003) Blood. 2003 Aug. 15; 102(4):1389-96; Salih H R et al. (2002) J Immunol.; 169(8):4098-102].

The present inventor here provides strategies for immunotherapy by which T-cells, especially allogeneic T-cells, are made particular suitable for allogeneic transplantations, reducing the risk for host versus graft rejections and for developing graft versus host disease and to render the T cells "stealthy", in particular with respect to APC cells or NK cells.

SUMMARY OF THE INVENTION

The present invention concerns methods for preparing engineered T-cells, in particular allogeneic T-cells obtained from a donor, to make them suitable for immunotherapy purposes. The methods of the present invention more particularly allow the precise modulation of expression of certain effector molecules important for immune recognition and histocompatibility.

According to one aspect, the present invention provides a method for preparing an engineered T-cell, preferably an allogeneic T-cell obtained from a donor, comprising the steps of:
  a) providing a T-cell, preferably an allogeneic T-cell obtained from a donor; and
  b) inhibiting the expression of beta 2-microglobulin (B2M) and/or class II major histocompatibility complex transactivator (CIITA) in said T-cell.

According to certain embodiments, inhibition of expression of B2M is achieved by a genome modification, more particularly through the expression in the T-cell of a rare-cutting endonuclease able to selectively inactivate by DNA cleavage the gene encoding B2M, such as the human β2m gene set forth in SEQ ID NO: 2 (NCBI Reference Sequence: NG_012920.1), or a gene having at least 70%, such as at least 80%, at least 90% at least 95%, or at least 99%, sequence identify with the human β2m gene set forth in SEQ ID NO: 2 over the entire length of SEQ ID NO: 2. Such rare-cutting endonuclease may be a TAL-nuclease, meganuclease, zing-finger nuclease (ZFN), or RNA guided endonuclease (such as Cas9).

According to certain other embodiments, inhibition of expression of B2M is achieved by using (e.g., introducing into the T-cell) a nucleic acid molecule that specifically hybridizes (e.g. binds) under cellular conditions with the cellular mRNA and/or genomic DNA encoding B2M, thereby inhibiting transcription and/or translation of the gene. In accordance with particular embodiments, the inhibition of expression of B2M is achieved by using ((e.g., introducing into the T-cell) an antisense oligonucleotide, ribozyme or interfering RNA (RNAi) molecule. Preferably, such nucleic acid molecule comprises at least 10 consecutive nucleotides of the complement of SEQ ID NO: 3 (i.e., the mRNA encoding human B2M; NCBI Reference Sequence: NM_004048).

According to certain embodiments, inhibition of expression of CIITA is achieved by a genome modification, more particularly through the expression in the T-cell of a rare-cutting endonuclease able to selectively inactivate by DNA cleavage the gene encoding CIITA, such as the human CIITA gene (NCBI Reference Sequence: NG_009628.1), or a gene having at least 70%, such as at least 80%, at least 90% at least 95%, or at least 99%, sequence identify with the human CIITA gene according to NG_009628.1 over the entire length of the human CIITA gene according to NG_009628.1. Such rare-cutting endonuclease may be a TAL-nuclease, meganuclease, zing-finger nuclease (ZFN), or RNA guided endonuclease (such as Cas9).

According to certain other embodiments, inhibition of expression of CIITA is achieved by using (e.g., introducing into the T-cell) a nucleic acid molecule that specifically hybridizes (e.g. binds) under cellular conditions with the cellular mRNA and/or genomic DNA encoding CIITA, thereby inhibiting transcription and/or translation of the gene. In accordance with particular embodiments, the inhibition of expression of CIITA is achieved by using ((e.g., introducing into the T-cell) an antisense oligonucleotide, ribozyme or interfering RNA (RNAi) molecule. Preferably, such nucleic acid molecule comprises at least 10 consecutive nucleotides of the complement of SEQ ID NO: 5 (i.e., the mRNA encoding human CIITA isoform 2).

According to particular embodiments, the T-cell may be further engineered to make it non-alloreactive, especially by inactivating one or more genes involved in self-recognition, such as those, for instance, encoding components of T-cell receptors (TCR). This can be achieved by a genome modification, more particularly through the expression in the T-cell of a rare-cutting endonuclease able to selectively inactivate by DNA cleavage, preferably double-strand break, at least one gene encoding a component of the T-Cell receptor (TCR), such as the gene encoding TCR alpha or TCR beta. Such rare-cutting endonuclease may be a TAL-nuclease, meganuclease, zing-finger nuclease (ZFN), or RNA guided endonuclease (such as, Cas9). Preferably, the rare-cutting endonuclease is able to selectively inactivate by DNA cleavage the gene coding for TCR alpha.

According to optional embodiments, the T-cell may be further engineered to express a Chimeric Antigen Receptor (CAR) directed against at least one antigen expressed at the surface of a malignant or infected cell, such as the B-lymphocyte antigen CD19.

The present invention thus provides in a further aspect engineered T-cells, in particular engineered isolated T-cells, characterized in that the expression of beta 2-microglobulin (B2M) is inhibited.

According to certain embodiments, a T-cell is provided which expresses a rare-cutting endonuclease able to selectively inactivate by DNA cleavage the gene encoding B2M. More particularly, such T-cell comprises an exogenous nucleic acid molecule comprising a nucleotide sequence encoding said rare-cutting endonuclease, which may be a TAL-nuclease, meganuclease, zing-finger nuclease (ZFN), or RNA guided endonuclease.

According to certain other embodiments, a T-cell is provided which comprises an exogenous nucleic acid molecule that inhibits the expression of B2M. According to particular embodiments, such nucleic acid molecule is an antisense oligonucleotide, ribozyme or interfering RNA (RNAi) molecule. According to preferred embodiments, such nucleic acid molecule comprises at least 10 consecutive nucleotides of the complement of SEQ ID NO: 3.

The present invention further provides engineered T-cells, in particular engineered isolated T-cells, characterized in that the expression of class II major histocompatibility complex transactivator (CIITA) is inhibited.

According to certain embodiments, a T-cell is provided which expresses a rare-cutting endonuclease able to selectively inactivate by DNA cleavage the gene encoding CIITA. More particularly, such T-cell comprises an exogenous nucleic acid molecule comprising a nucleotide sequence encoding said rare-cutting endonuclease, which may be a TAL-nuclease, meganuclease, zing-finger nuclease (ZFN), or RNA guided endonuclease.

According to certain other embodiments, a T-cell is provided which comprises an exogenous nucleic acid molecule that inhibits the expression of CIITA. According to particular embodiments, such nucleic acid molecule is an antisense oligonucleotide, ribozyme or interfering RNA (RNAi) molecule. According to preferred embodiments, such nucleic acid molecule comprises at least 10 consecutive nucleotides of the complement of SEQ ID NO: 5.

According to particular embodiments, the T-cell may further have at least one inactivated gene encoding a component of the TCR receptor. More particularly, such T-cell may express a rare-cutting endonuclease able to selectively inactivate by DNA cleavage, preferably double-strand break, said at least one gene encoding a component of the T-Cell receptor (TCR). Accordingly, said T-cell may comprise an exogenous nucleic acid molecule comprising a nucleotide sequence coding for a rare-cutting endonuclease able to selectively inactivate by DNA cleavage at least one gene coding for one component of the T-Cell receptor (TCR). The disruption of TCR provides a non-alloreactive T-cell that can be used in allogeneic treatment strategies.

According to optional embodiments, the T-cell may be engineered to express a Chimeric Antigen Receptor (CAR) directed against at least one antigen expressed at the surface of a malignant or infected cell, such as the B-lymphocyte antigen CD19. Particularly, the T-cell comprises an exogenous nucleic acid molecule comprising a nucleotide sequence encoding said CAR. The binding of the target antigen by the CAR has the effect of triggering an immune response by the T-cell directed against the pathological cell, which results in degranulation of various cytokine and degradation enzymes in the interspace between the cells.

According to some embodiments, an additional modification of T-cells is performed to render them stealthy by expression of at least one non-endogenous immunosuppressive polypeptide such as a viral MHC homolog, for instance, UL18, or such as a NKG2D ligand.

According to some embodiments, the T-cell of the present invention expresses at least one non-endogenous immune-suppressive polypeptide. According to more particular embodiments, said non-endogenous immune-suppressive polypeptide is a viral MHC homolog, such as UL18. The T-cell may comprise an exogenous nucleic acid molecule comprising a nucleotide sequence cording for a polypeptide sharing at least 80%, preferably at least 90% and more preferably at least 95% of identity with SEQ ID NO: 89. According to other more particular embodiments, said non-endogenous immune-suppressive polypeptide is a NKG2D ligand. The T-cell may comprise an exogenous nucleic acid molecule comprising a nucleotide sequence cording for a polypeptide sharing at least 80%, preferably at least 90% and more preferably at least 95% of identity with any one of SEQ ID NO: 90-97.

As a result of the present invention, engineered T-cells can be used as therapeutic products, ideally as an "off the shelf" product, for use in the treatment or prevention cancer, bacterial or viral infections, or auto-immune diseases.

Thus, the present invention further provides an engineered T-cell or a composition, such as a pharmaceutical composition, comprising same for use as a medicament. According to certain embodiments, the engineered T-cell or composition is for use in the treatment of a cancer, and more particularly for use in the treatment of lymphoma. According to certain other embodiments, the engineered T-cell or composition is for use in the treatment of viral infection. According to certain other embodiments, the engineered T-cell or composition is for use in the treatment of bacterial infection.

It is understood that the details given herein with respect to one aspect of the invention also apply to any of the other aspects of the invention.

DETAILED DESCRIPTION OF THE INVENTION

Figure 1:
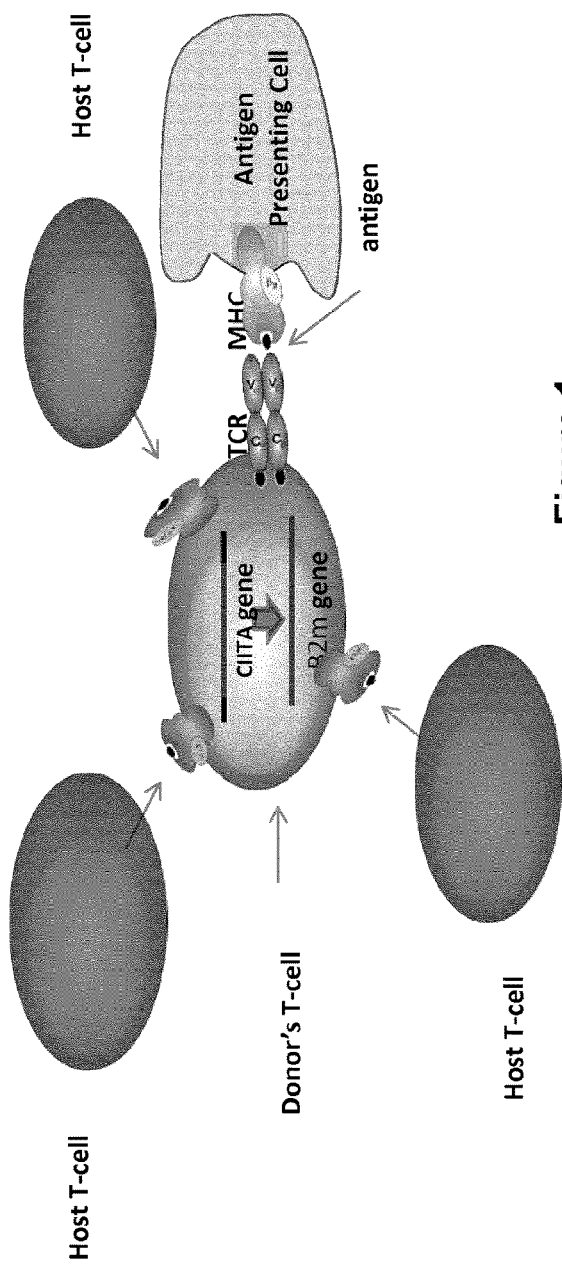
FIG. 1: Schematic representation of the normal relationship between donor's T-cells, host T-cells and antigen presenting cells.
Figure 2:
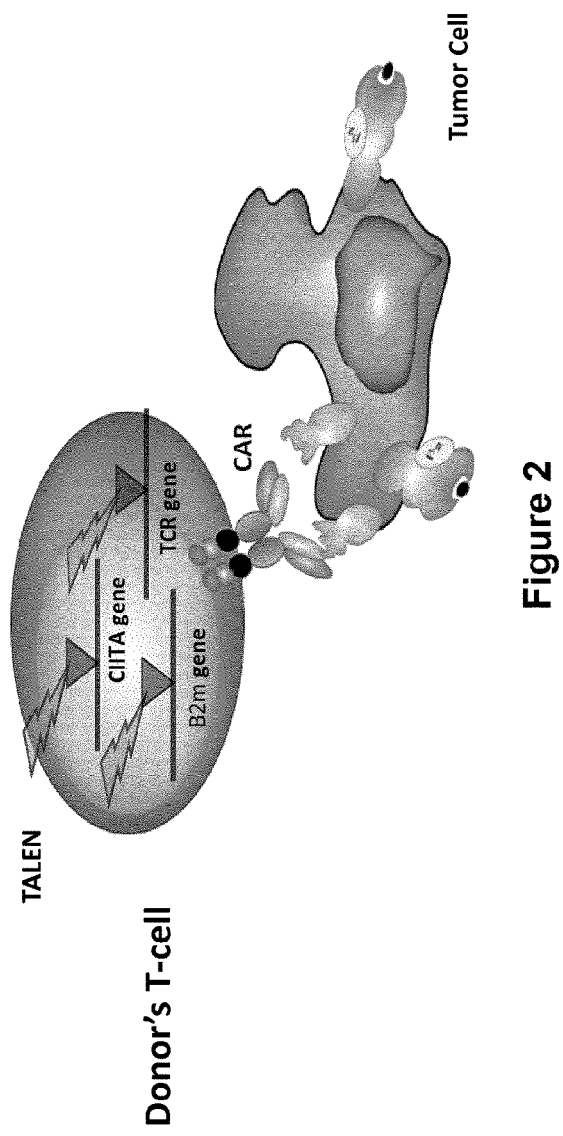
FIG. 2: Schematic representation of the genetically modified therapeutic T-cells according to the invention and the patient's T-cells and tumor cells.

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Methods for Preparing Engineered T-Cells

In a general aspect, the present invention pertains to methods for preparing engineered T-cells, in particular allogeneic T-cells obtained from a donor.

Accordingly, the present invention provides a method for preparing an engineered T-cell, preferably an allogeneic T-cell obtained from a donor, said method comprises the steps of:
a) providing a T-cell, preferably an allogeneic T-cell obtained from a donor; and
b) inhibiting the expression of beta 2-microglobulin (B2M) and/or class II major histocompatibility complex transactivator (CIITA) in said T-cell.

According to certain embodiments, the method comprises inhibiting the expression of beta 2-microglobulin (B2M).

Alternatively, or in addition, the method may comprise inhibiting the expression of class II major histocompatibility complex transactivator (CIITA).

According to certain embodiments, inhibition of expression of B2M is achieved by a genome modification, more particularly through the expression in the T-cell of a rare-cutting endonuclease able to selectively inactivate by DNA cleavage the gene encoding B2M (e.g. the human β2m gene set forth in SEQ ID NO: 2).

According to certain other embodiments, inhibition of expression of CIITA is achieved by a genome modification, more particularly through the expression in the T-cell of a rare-cutting endonuclease able to selectively inactivate by DNA cleavage the gene encoding CIITA (e.g. the human CIITA gene).

By "inactivating" or "inactivation of" a gene it is intended that the gene of interest (e.g. the gene encoding B2M or CIITA) is not expressed in a functional protein form. In particular embodiments, the genetic modification of the method relies on the expression, in provided cells to engineer, of a rare-cutting endonuclease such that same catalyzes cleavage in one targeted gene thereby inactivating said targeted gene. The nucleic acid strand breaks caused by the endonuclease are commonly repaired through the distinct mechanisms of homologous recombination or non-homologous end joining (NHEJ). However, NHEJ is an imperfect repair process that often results in changes to the DNA sequence at the site of the cleavage. Mechanisms involve rejoining of what remains of the two DNA ends through direct re-ligation (Critchlow and Jackson 1998) or via the so-called microhomology-mediated end joining (Betts, Brenchley et al. 2003; Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event, i.e. a mutagenesis event consecutive to an NHEJ event, has occurred can be identified and/or selected by well-known method in the art.

A rare-cutting endonuclease to be used in accordance of the present invention to inactivate the β2m gene may, for instance, be a TAL-nuclease, meganuclease, zing-finger nuclease (ZFN), or RNA guided endonuclease (such as Cas9).

According to a particular embodiment, the rare-cutting endonuclease is a TAL-nuclease.

According to another particular embodiment, the rate-cutting endonuclease is a homing endonuclease, also known under the name of meganuclease.

According to another particular embodiment, the rare-cutting endonuclease is a zing-finger nuclease (ZNF).

According to another particular embodiment, the rare-cutting endonuclease is a RNA guided endonuclease. According to a preferred embodiment, the RNA guided endonuclease is the Cas9/CRISPR complex.

According to a specific embodiment, the rare-cutting endonuclease is a TAL-nuclease encoded by a nucleic acid molecule comprising the nucleotide sequence set for in SEQ ID NO: 67. According to another specific embodiment, the rare-cutting endonuclease is a TAL-nuclease encoded by a nucleic acid molecule comprising the nucleotide sequence set for in SEQ ID NO: 68. In yet another specific embodiment, the rare-cutting endonuclease is a combination of a TAL-nuclease encoded by a nucleic acid molecule comprising the nucleotide sequence set for in SEQ ID NO: 67 and a TAL-nuclease encoded by a nucleic acid molecule comprising the nucleotide sequence set for in SEQ ID NO: 68.

In order to be expressed in the T-cell, said rare-cutting endonuclease may be introduced into the cell by way of an exogenous nucleic acid molecule comprising a nucleotide sequence encoding said rare-cutting endonuclease. According to particular embodiments, the method of the invention further comprises introducing into said T-cell an exogenous nucleic acid molecule comprising a nucleotide sequence coding for a rare-cutting endonuclease, preferably a rare-cutting endonuclease able to selectively inactivate by DNA cleavage the gene encoding B2M (e.g. the human β2m gene set forth in SEQ ID NO: 2). For example, the exogenous nucleic acid molecule may comprising the nucleotide sequence set for in SEQ ID NO: 67 or SEQ ID NO: 68.

As a result, an engineered T-cell is obtained which expresses a rare-cutting endonuclease, preferably a rare-cutting endonuclease able to selectively inactivate by DNA cleavage the gene encoding B2M. In consequence, inactivation of the B2M gene by said rare-cutting endonuclease leads to the inhibition of the expression of B2M in the engineered T-cell. Hence, an engineered T-cell is obtained which is characterized in that the expression of B2M is inhibited.

A rare-cutting endonuclease to be used in accordance of the present invention to inactivate the CIITA gene may, for instance, be a TAL-nuclease, meganuclease, zing-finger nuclease (ZFN), or RNA guided endonuclease (such as Cas9).

According to a particular embodiment, the rare-cutting endonuclease is a TAL-nuclease.

According to another particular embodiment, the rate-cutting endonuclease is a homing endonuclease, also known under the name of meganuclease.

According to another particular embodiment, the rare-cutting endonuclease is a zing-finger nuclease (ZNF).

According to another particular embodiment, the rare-cutting endonuclease is a RNA guided endonuclease. According to a preferred embodiment, the RNA guided endonuclease is the Cas9/CRISPR complex.

In order to be expressed in the T-cell, said rare-cutting endonuclease may be introduced into the cell by way of an exogenous nucleic acid molecule comprising a nucleotide sequence encoding said rare-cutting endonuclease. According to particular embodiments, the method of the invention further comprises introducing into said T-cell an exogenous nucleic acid molecule comprising a nucleotide sequence coding for a rare-cutting endonuclease, preferably a rare-cutting endonuclease able to selectively inactivate by DNA cleavage the gene encoding CIITA (e.g. the human CIITA gene).

As a result, an engineered T-cell is obtained which expresses a rare-cutting endonuclease, preferably a rare-cutting endonuclease able to selectively inactivate by DNA cleavage the gene encoding CIITA. In consequence, inactivation of the CIITA gene by said rare-cutting endonuclease leads to the inhibition of the expression of CIITA in the engineered T-cell. Hence, an engineered T-cell is obtained which is characterized in that the expression of CIITA is inhibited. According to certain other embodiments, inhibition of expression of B2M is achieved by using (e.g., introducing into the T-cell) a nucleic acid molecule that specifically hybridizes (e.g. binds) under cellular conditions with the cellular mRNA and/or genomic DNA encoding B2M, thereby inhibiting transcription and/or translation of the gene. In accordance with particular embodiments, the inhibition of expression of B2M is achieved by using (e.g., introducing into the T-cell) an antisense oligonucleotide, ribozyme or interfering RNA (RNAi) molecule.

According to a particular embodiment, the nucleic acid molecule is an antisense oligonucleotide.

According to other particular embodiments, the nucleic acid molecule is a ribozyme, preferably a hammerhead ribozyme.

According to other particular embodiments, the nucleic acid is an interfering RNA (RNAi) molecule, such as a micro RNA (miRNA), small interfering RNA (siRNA) or short hairpin RNA (shRNA). Hence, in accordance with a preferred embodiment, the nucleic acid molecule is a micro RNA. In accordance with another preferred embodiment, the nucleic acid molecule is a small interfering RNA. In accordance with another preferred embodiment, the nucleic acid molecule is a short hairpin RNA.

As a result, an engineered T-cell is obtained which is characterized in that the expression of B2M is inhibited.

Because B2M is an important structural component of the major histocompatibility complex (MHC), inhibition of B2M expression leads to a reduction or elimination of MHC molecules on the surface of the engineered T-cell. In consequence, the engineered T-cell no longer presents antigens on the surface which are recognized by CD8+ cells. Especially in case of an allogeneic T-cell obtained from a donor, reduction or elimination of nonself-antigen presenting MHC molecules on the surface of the T-cell prevents the engineered T-cell, when infused into an allogeneic host, from being recognized by the host CD8+ cells. This makes the engineered T-cell particular suitable for allogeneic transplantations, especially because it reduces the risk of rejection by the host's immune system.

According to certain other embodiments, inhibition of expression of CIITA is achieved by using (e.g., introducing into the T-cell) a nucleic acid molecule that specifically hybridizes (e.g. binds) under cellular conditions with the cellular mRNA and/or genomic DNA encoding CIITA, thereby inhibiting transcription and/or translation of the gene. In accordance with particular embodiments, the inhibition of expression of CIITA is achieved by using (e.g., introducing into the T-cell) an antisense oligonucleotide, ribozyme or interfering RNA (RNAi) molecule.

According to a particular embodiment, the nucleic acid molecule is an antisense oligonucleotide.

According to other particular embodiments, the nucleic acid molecule is a ribozyme, preferably a hammerhead ribozyme.

According to other particular embodiment, the nucleic acid is an interfering RNA (RNAi) molecule, such as a micro RNA (miRNA), small interfering RNA (siRNA) or short hairpin RNA (shRNA). Hence, in accordance with a preferred embodiment, the nucleic acid molecule is a micro RNA. In accordance with another preferred embodiment, the nucleic acid molecule is a small interfering RNA. In accordance with another preferred embodiment, the nucleic acid molecule is a short hairpin RNA.

As a result, an engineered T-cell is obtained which is characterized in that the expression of CIITA is inhibited. It is also contemplated by the present invention that the engineered T-cell of the present invention does not express a functional T-cell receptor (TCR) on its cell surface. T-cell receptors are cell surface receptors that participate in the activation of T cells in response to the presentation of antigen. The TCR is generally made from two chains, alpha and beta, which assemble to form a heterodimer and associates with the CD3-transducing subunits to form the T-cell receptor complex present on the cell surface. Each alpha and beta chain of the TCR consists of an immunoglobulin-like N-terminal variable (V) and constant (C) region, a hydrophobic transmembrane domain, and a short cytoplasmic region. As for immunoglobulin molecules, the variable region of the alpha and beta chains are generated by V(D)J recombination, creating a large diversity of antigen specificities within the population of T cells. However, in contrast to immunoglobulins that recognize intact antigen, T-cells are activated by processed peptide fragments in association with an MHC molecule, introducing an extra dimension to antigen recognition by T cells, known as MHC restriction. Recognition of MHC disparities between the donor and recipient through the T-cell receptor leads to T-cell proliferation and the potential development of graft versus host disease (GVHD). It has been shown that normal surface expression of the TCR depends on the coordinated synthesis and assembly of all seven components of the complex (Ashwell and Klusner 1990). The inactivation of TCR alpha or TCR beta can result in the elimination of the TCR from the surface of T-cells preventing recognition of alloantigen and thus GVHD. The inactivation of at least one gene coding for a TCR component thus renders the engineered T-cell less alloreactive. By "inactivating" or "inactivation of" a gene it is meant that the gene of interest (e.g., at least one gene coding for a TCR component) is not expressed in a functional protein form.

Therefore, the method of the present invention in accordance with particular embodiments further comprises inactivating at least one gene encoding a component of the T-cell receptor. More particularly, the inactivation is achieved by using (e.g., introducing into the T-cell) a rare-cutting endonuclease able to selectively inactivate by DNA cleavage, preferably double-strand break, at least one gene encoding a component of the T-Cell receptor (TCR). According to particular embodiments, the rare-cutting endonuclease is able to selectively inactivate by DNA cleavage the gene coding for TCR alpha or TCR beta. According to a preferred embodiment, the rare-cutting endonuclease is able to selectively inactivate by DNA cleavage the gene coding for TCR alpha. Especially in case of an allogeneic T-cell obtained from a donor, inactivating of at least one gene encoding a component of TCR, notably TCR alpha, leads to engineered T-cells, when infused into an allogeneic host, which are non-alloreactive. This makes the engineered T-cell particular suitable for allogeneic transplantations, especially because it reduces the risk of graft versus host disease.

A rare-cutting endonuclease to be used in accordance of the present invention to inactivate at least one gene encoding a component of the T-cell receptor may, for instance, be a TAL-nuclease, meganuclease, zing-finger nuclease (ZFN), or RNA guided endonuclease (such as Cas9).

According to a particular embodiment, the rare-cutting endonuclease is a TAL-nuclease.

According to another particular embodiment, the rate-cutting endonuclease is a homing endonuclease, also known under the name of meganuclease.

According to another particular embodiment, the rare-cutting endonuclease is a zing-finger nuclease (ZNF).

According to another particular embodiment, the rare-cutting endonuclease is a RNA guided endonuclease. According to a preferred embodiment, the RNA guided endonuclease is the Cas9/CRISPR complex.

In order to be expressed in the T-cell, said rare-cutting endonuclease may be introduced into the cell by way of an exogenous nucleic acid molecule comprising a nucleotide sequence encoding said rare-cutting endonuclease. According to particular embodiments, the method of the invention further comprises introducing into said T-cell an exogenous nucleic acid molecule comprising a nucleotide sequence coding for a rare-cutting endonuclease able to selectively inactivate by DNA cleavage, preferably double-strand break, at least one gene encoding a component of the T-cell receptor (TCR).

As a result, an engineered T-cell is obtained which further expresses a rare-cutting endonuclease able to selectively inactivate by DNA cleavage at least one gene encoding a component of the T-cell receptor (TCR). In consequence, an engineered T-cell is obtained which is characterized in that at least at least one gene encoding a component of the T-cell receptor (TCR) is inactivated.

It is also contemplated by the present invention that the engineered T-cell further expresses a Chimeric Antigen Receptor (CAR) directed against at least one antigen expressed at the surface of a malignant or infected cell. Hence, in accordance with certain embodiments, the method of the invention furthers comprise introducing into said T-cell an exogenous nucleic acid molecule comprising a nucleotide sequence coding for a Chimeric Antigen Receptor (CAR) directed against at least one antigen expressed at the surface of a malignant or infected cell.

The T-cell to be modified according to the present invention may be any suitable T-cell. For example, the T-cell can be an inflammatory T-lymphocyte, cytotoxic T-lymphocyte, regulatory T-cell or helper T-lymphocyte. Particularly, the T-cell is a cytotoxic T-lymphocyte. In certain embodiments, said T-cell is selected from CD4+ T-lymphocytes and CD8+ T-lymphocytes. They can be extracted from blood or derived from stem cells. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. In particular embodiments, the T-cell to be modified according to the present invention is a human T-cell. Prior to expansion and genetic modification of the cells of the invention, a source of cells can be obtained from a subject, such as a patient, through a variety of non-limiting methods. T-cell can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics.

Rare-Cutting Endonuclease

In accordance with certain embodiments of the present invention, rare-cutting endonucleases are employed which are able to selectively inactivate by DNA cleavage the gene of interest, such as the gene encoding B2M.

The term "rare-cutting endonuclease" refers to a wild type or variant enzyme capable of catalyzing the hydrolysis (cleavage) of bonds between nucleic acids within a DNA or RNA molecule, preferably a DNA molecule. Particularly, said nuclease can be an endonuclease, more preferably a rare-cutting endonuclease which is highly specific, recognizing nucleic acid target sites ranging from 10 to 45 base pairs (bp) in length, usually ranging from 10 to 35 base pairs in length, more usually from 12 to 20 base pairs. The endonuclease according to the present invention recognizes at specific polynucleotide sequences, further referred to as "target sequence" and cleaves nucleic acid inside these target sequences or into sequences adjacent thereto, depending on the molecular structure of said endonuclease. The rare-cutting endonuclease can recognize and generate a single- or double-strand break at specific polynucleotides sequences.

In particular embodiments, said rare-cutting endonuclease according to the present invention is a RNA-guided endonuclease such as the Cas9/CRISPR complex. RNA guided endonucleases constitute a new generation of genome engineering tool where an endonuclease associates with a RNA molecule. In this system, the RNA molecule nucleotide sequence determines the target specificity and activates the endonuclease (Gasiunas, Barrangou et al. 2012; Jinek, Chylinski et al. 2012; Cong, Ran et al. 2013; *Mali*, Yang et al. 2013). Cas9, also named Csn1 is a large protein that participates in both crRNA biogenesis and in the destruction of invading DNA. Cas9 has been described in different bacterial species such as *S. thermophiles, Listeria innocua* (Gasiunas, Barrangou et al. 2012; Jinek, Chylinski et al. 2012) and *S. Pyogenes* (Deltcheva, Chylinski et al. 2011). The large Cas9 protein (>1200 amino acids) contains two predicted nuclease domains, namely HNH (McrA-like) nuclease domain that is located in the middle of the protein and a splitted RuvC-like nuclease domain (RNase H fold). Cas9 variant can be a Cas9 endonuclease that does not naturally exist in nature and that is obtained by protein engineering or by random mutagenesis. Cas9 variants according to the invention can for example be obtained by mutations i.e. deletions from, or insertions or substitutions of at least one residue in the amino acid sequence of a *S. pyogenes* Cas9 endonuclease (COG3513).

In other particular embodiments, said rare-cutting endonuclease can also be a homing endonuclease, also known under the name of meganuclease. Such homing endonucleases are well-known to the art (Stoddard 2005). Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-CreI variant. A "variant" endonuclease, i.e. an endonuclease that does not naturally exist in nature and that is obtained by genetic engineering or by random mutagenesis can bind DNA sequences different from that recognized by wild-type endonucleases (see international application WO2006/097854).

In other particular embodiments, said rare-cutting endonuclease can be a "Zinc Finger Nucleases" (ZFNs), which are generally a fusion between the cleavage domain of the type IIS restriction enzyme, FokI, and a DNA recognition domain containing 3 or more C2H2 zinc finger motifs. The heterodimerization at a particular position in the DNA of two individual ZFNs in precise orientation and spacing leads to a double-strand break (DSB) in the DNA. The use of such chimeric endonucleases have been extensively reported in the art as reviewed by Urnov et al. (Genome editing with engineered zinc finger nucleases (2010) *Nature reviews Genetics* 11:636-646). Standard ZFNs fuse the cleavage domain to the C-terminus of each zinc finger domain. In order to allow the two cleavage domains to dimerize and cleave DNA, the two individual ZFNs bind opposite strands of DNA with their C-termini a certain distance apart. The most commonly used linker sequences between the zinc finger domain and the cleavage domain requires the 5' edge of each binding site to be separated by 5 to 7 bp. The most straightforward method to generate new zinc-finger arrays is to combine smaller zinc-finger "modules" of known specificity. The most common modular assembly process involves combining three separate zinc fingers that can each recognize a 3 base pair DNA sequence to generate a 3-finger array that can recognize a 9 base pair target site. Numerous selection methods have been used to generate zinc-finger arrays capable of targeting desired sequences. Initial selection efforts utilized phage display to select proteins that bound a given DNA target from a large pool of partially randomized zinc-finger arrays. More recent efforts have utilized yeast one-hybrid systems, bacterial one-hybrid and two-hybrid systems, and mammalian cells.

In other particular embodiments, said rare-cutting endonuclease is a "TALE-nuclease" or a "MBBBD-nuclease" resulting from the fusion of a DNA binding domain typically derived from Transcription Activator Like Effector proteins (TALE) or from a Modular Base-per-Base Binding domain (MBBBD), with a catalytic domain having endonuclease activity. Such catalytic domain usually comes from enzymes, such as for instance I-TevI, ColE7, NucA and Fok-I. TALE-nuclease can be formed under monomeric or dimeric forms depending of the selected catalytic domain (WO2012138927). Such engineered TALE-nucleases are commercially available under the trade name TALEN™ (Cellectis, 8 rue de la Croix Jarry, 75013 Paris, France). In general, the DNA binding domain is derived from a Transcription Activator like Effector (TALE), wherein sequence specificity is driven by a series of 33-35 amino acids repeats originating from *Xanthomonas* or *Raistonia* bacterial proteins AvrBs3, PthXo1, AvrHah1, PthA, Tal1c as non-limiting examples. These repeats differ essentially by two amino acids positions that specify an interaction with a base pair (Boch, Scholze et al. 2009; Moscou and Bogdanove 2009). Each base pair in the DNA target is contacted by a single repeat, with the specificity resulting from the two variant amino acids of the repeat (the so-called repeat variable dipeptide, RVD). TALE binding domains may further comprise an N-terminal translocation domain responsible for the requirement of a first thymine base (T0) of the targeted sequence and a C-terminal domain that containing a nuclear localization signals (NLS). A TALE nucleic acid binding domain generally corresponds to an engineered core TALE scaffold comprising a plurality of TALE repeat sequences, each repeat comprising a RVD specific to each nucleotides base of a TALE recognition site. In the present invention, each TALE repeat sequence of said core scaffold is made of 30 to 42 amino acids, more preferably 33 or 34 wherein two critical amino acids (the so-called repeat variable dipeptide, RVD) located at positions 12 and 13 mediates the recognition of one nucleotide of said TALE binding site sequence; equivalent two critical amino acids can be located at positions other than 12 and 13 specially in TALE repeat sequence taller than 33 or 34 amino acids long. Preferably, RVDs associated with recognition of the different nucleotides are HD for recognizing C, NG for recognizing T, NI for recognizing A, NN for recognizing G or A. In another embodiment, critical amino acids 12 and 13 can be mutated towards other amino acid residues in order to modulate their specificity towards nucleotides A, T, C and G and in particular to enhance this specificity. A TALE nucleic acid binding domain usually comprises between 8 and 30 TALE repeat sequences. More preferably, said core scaffold of the present invention comprises between 8 and 20 TALE repeat sequences; again more preferably 15 TALE repeat sequences. It can also comprise an additional single truncated TALE repeat sequence made of 20 amino acids located at the C-terminus of said set of TALE repeat sequences, i.e. an additional C-terminal half-TALE repeat sequence. Other modular base-per-base specific nucleic acid binding domains (MBBBD) are described in WO 2014/018601. Said MBBBD can be engineered, for instance, from newly identified proteins, namely EAV36_BURRH, E5AW43_BURRH, E5AW45_BURRH and E5AW46_BURRH proteins from the recently sequenced genome of the endosymbiont fungi *Burkholderia Rhizoxinica*. These nucleic acid binding polypeptides comprise modules of about 31 to 33 amino acids that are base specific. These modules display less than 40% sequence identity with *Xanthomonas* TALE common repeats and present more polypeptides sequence variability. The different domains from the above proteins (modules, N and C-terminals) from *Burkholderia* and *Xanthomonas* are useful to engineer new proteins or scaffolds having binding properties to specific nucleic acid sequences and may be combined to form chimeric TALE-MBBBD proteins.

Inhibitory Nucleic Acid Molecules

In accordance with certain other embodiments of the present invention, nucleic acid molecules are employed which inhibit the expression of B2M. More particularly, the nucleic acid may be an antisense oligonucleotide, ribozyme or interfering RNA (RNAi) molecule. Preferably, such nucleic acid molecule comprises at least 10 consecutive nucleotides of the complement of SEQ ID NO: 3.

According to particular embodiments, the inhibitory nucleic acid is an antisense oligonucleotide which inhibits the expression of B2M. Such antisense oligonucleotide is an nucleic acid (either DNA or RNA) which specifically hybridizes (e.g. binds) under cellular conditions with the cellular mRNA and/or genomic DNA encoding B2M, thereby inhibiting transcription and/or translation of the gene. The binding may be by conventional base pair complementarity. Alternatively, the binding may be, for example, in case of binding to DNA duplexes, through specific interactions in the major groove of the double helix. Absolute complementarity, although preferred, is not required.

Also contemplated by the present invention is that nucleic acid molecules are employed which inhibit the expression of CIITA. More particularly, the nucleic acid may be an antisense oligonucleotide, ribozyme or interfering RNA (RNAi) molecule. Preferably, such nucleic acid molecule comprises at least 10 consecutive nucleotides of the complement of SEQ ID NO: 5.

Antisense oligonucleotides employed according to the invention may be DNA or RNA or chimeric mixtures or derivatives or modified versions thereof, and may be single-stranded or double stranded. Thus, according to a preferred embodiment, the antisense oligonucleotide is a single-stranded or double-stranded DNA molecule, more preferably a double-stranded DNA molecule. According to another preferred embodiment, the antisense oligonucleotide is a single-stranded or double-stranded RNA molecule, more preferably a single-stranded RNA molecule.

According to preferred embodiments, the antisense oligonucleotide is a modified oligonucleotide which is resistant to endogenous nucleases, e.g., exonucleases and/or endonucleases, and is therefore stable in vivo and in vitro.

The antisense oligonucleotide may be modified at the base moiety, sugar moiety, or phosphate backbone, for example, to improve stability of the molecule. The antisense oligonucleotide may include other appended groups such as peptides (e.g., for targeting host cell receptors), or agents facilitating transport across the cell membrane. Hence, the antisense oligonucleotide may be conjugated to another molecule such as a peptide or transport agent.

According to particular embodiments, the antisense oligonucleotide comprises at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxytriethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w and 2,6-diaminopurine.

According to other particular embodiments, the antisense oligonucleotide comprise at least one modified sugar moiety selected from the group including, but not limited to, arabinose, 2-fluoroarabinose, xylulose and hexose.

According to other particular embodiments, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

An antisense oligonucleotide may be delivered into the cell, for example, in form of an expression vector, such as a plasmid or viral vector, which, when transcribed in the cells, produces RNA which is complementary to at least a unique portion of the cellular mRNA for B2M. Alternatively, the antisense oligonucleotide may be generated ex vivo and introduced into the cell by any known means in the art. The antisense oligonucleotide may be synthesise ex vivo by standard method known in the art, e.g., by use of an automated DNA synthesizer (such as automated DNA synthesizer are commercially available from, e.g., Applied Biosystems). A number of methods have been developed for delivering antisense DNA or RNA to cells, e.g. by direct injection or through modification designed to target the desired cell (e.g., using antisense oligonucleotides linked to peptides or antibodies that specifically bind receptors or antigens expressed on the target cell surface.

According to preferred embodiments, a recombinant DNA vector is used in which a nucleotide sequence coding for an antisense oligonucleotide inhibiting the expression of B2M or CIITA is placed under the control of a promoter, such as a strong pol III or pol II promoter. The use of such a construct to transfect a target cell, such as a T-cell, will result in the transcription of a sufficient amount of single-stranded RNA that will form complementary base pairs with the endogenous transcript and thereby prevent translation of the B2M or CIITA mRNA. In accordance with these embodiments, a DNA vector comprising the nucleotide sequence encoding the antisense oligonucleotide is introduced into the cell where the transcription of an antisense RNA occurs. Such vector can remain episomal or be chromosomally integrated, as long as it can be transcribed to produce the antisense RNA. The expression of the sequence encoding the antisense RNA can be by any promoter known in the art to act in mammalian, preferably human cells. Such promoter can be inducible or constitutive. Exemplary promoters include, but are not limited to, the SV40 early promoter region, the promoter containing the 3' long terminal repeat of Rous sarcoma virus, the herpes thymidine promoter, and the regulatory sequences of the methallothionein gene.

Alternatively, antisense cDNA constructs that synthesize antisense RNA constitutively or inducibly, depending on the promoter used, can be introduced into the cell.

According to preferred embodiments, the antisense oligonucleotide comprises at least 10 consecutive nucleotides of the complement of SEQ ID NO: 3. In case of a double stranded molecule, such double-stranded antisense oligonucleotide comprises a first strand comprising at least 10 consecutive nucleotide of SEQ ID NO: 3, and a second strand complementary to said first strand. In case of a single-stranded molecule, such single-stranded oligonucleotide comprises at least 10 consecutive nucleotides of the complement of SEQ ID NO: 3.

According to other preferred embodiments, the antisense oligonucleotide comprises at least 10 consecutive nucleotides of the complement of SEQ ID NO: 5. In case of a double stranded molecule, such double-stranded antisense oligonucleotide comprises a first strand comprising at least 10 consecutive nucleotide of SEQ ID NO: 5, and a second strand complementary to said first strand. In case of a single-stranded molecule, such single-stranded oligonucleotide comprises at least 10 consecutive nucleotides of the complement of SEQ ID NO: 5.

The antisense oligonucleotide may comprise a nucleotide sequence complementary to a non-coding or a coding region of the B2M or CIITA mRNA. According to preferred embodiments, the antisense oligonucleotide comprises a nucleotide sequence complementary to the 5' end of the B2M or CIITA mRNA, e.g., the 5' untranslated sequence up to and including the AUG initiation codon. According to other preferred embodiments, the antisense oligonucleotide comprises a nucleotide sequence complementary to the 3' untranslated sequence of the B2M or CIITA mRNA. According to other preferred embodiments, the antisense oligonucleotide comprises a nucleotide sequence complementary to the coding region of the B2M or CIITA mRNA. Whether designed to hybridize to the 5', 3' or coding region of the B2M or CIITA mRNA, an antisense oligonucleotide should be at least six nucleotides in length, preferably at least 10 nucleotide in length, and is preferably less than about 100, and more preferably less than about 50, 25, 20, 15 or 10 nucleotides in length. According to preferred embodiments, the antisense oligonucleotide is 6 to 25, such as 10 to 25 nucleotides in length.

In accordance with other particular embodiments, a ribozyme molecule designed to catalytically cleave the B2M or CIITA mRNA transcript is used to prevent translation and expression of B2M or CIITA in the T-cell, respectively (see, e.g., WO 90/11364 and U.S. Pat. No. 5,093,246 for general guidance). According to preferred embodiments, the ribozyme is a hammerhead ribozyme. Hammerhead ribozymes cleave mRNAs at locations dictated by flanking regions that form complementary base pairs with the target mRNA, e.g. the B2M mRNA, such as the human B2M mRNA set forth in SEQ ID NO: 3. The sole requirement is that the target mRNA has the following sequence of two bases: 5'-UG-3'. The constructions and production of hammerhead ribozymes is well known in the art and is described in more detail in Haseloff and Gerlach (1988). In accordance with preferred embodiments, the ribozyme is engineered such that the cleavage recognition site is located near the 5' end of the B2M mRNA. In accordance with preferred other embodiments, the ribozyme is engineered such that the cleavage recognition site is located near the 5' end of the CIITA mRNA. This increases the efficiency and minimizes the intracellular accumulation of non-functional mRNA transcripts.

Like with antisense oligonucleotides, a riboyzme used in accordance with the invention may be composed of modified oligonucleotides to, e.g., improve stability. The ribozyme may be delivered to the cell by any means known in the art. The ribozyme may be delivered to the T-cell in form of an expression vector, such as a plasmid or viral vector, which, when transcribed in the cells, produces the ribozyme. According to preferred embodiments, a recombinant DNA vector is used in which a nucleotide sequence coding for the ribozyme is placed under the control of a promoter, such as a strong pol III or pol II promoter, so that a transfected cell will produce sufficient amounts of the ribozyme to destroy endogenous mRNA and inhibit translation. Because riboyzmes, unlike antisense oligonucleotides, are cataylitc, a lower intracellular concentration is required for efficiency.

In accordance with other particular embodiments, the inhibitory nucleic acid is an interfering RNA (RNAi) molecule. RNA interference is a biological process in which RNA molecules inhibit gene expression, typically causing the destruction of specific mRNA. Exemplary types of RNAi molecules include microRNA (miRNA), small interfering RNA (siRNA) and short hairpin RNA (shRNA). According to a preferred embodiment, the RNAi molecule is a miRNA. According to another preferred embodiment, the RNAi molecule is a siRNA. According to yet another preferred embodiment, the RNAi molecule is a shRNA. The production of RNAi molecules in vivo and in vitro and their methods of use are described in, e.g., U.S. Pat. No. 6,506,559, WO 01/36646, WO 00/44895, US2002/01621126, US2002/0086356, US2003/0108923, WO 02/44321, WO 02/055693, WO 02/055692 and WO 03/006477.

In accordance with a preferred embodiment, the RNAi molecule is an interfering RNA complementary to SEQ ID NO: 3. In accordance to another preferred embodiment, the RNAi molecule is a ribonucleic acid molecule comprising at least 10 consecutive nucleotides of the complement of SEQ ID NO: 3. In accordance with another preferred embodiment, the RNAi molecule is a double-stranded ribonucleic acid molecule comprising a first strand identical to 20 to 25, such as 21 to 23, consecutive nucleotides of SEQ ID NO: 3, and a second strand complementary to said first strand.

In accordance with a preferred embodiment, the RNAi molecule is an interfering RNA complementary to SEQ ID NO: 5. In accordance to another preferred embodiment, the RNAi molecule is a ribonucleic acid molecule comprising at least 10 consecutive nucleotides of the complement of SEQ ID NO: 5. In accordance with another preferred embodiment, the RNAi molecule is a double-stranded ribonucleic acid molecule comprising a first strand identical to 20 to 25, such as 21 to 23, consecutive nucleotides of SEQ ID NO: 5, and a second strand complementary to said first strand.

Engineering of the PD1/PDL1 Pathway of T-Cell Regulation

The present invention aims at facilitating the engraftment of T-cells, especially allogeneic T-cells, preferably by inhibiting the expression of B2M and/or CIITA in combination with inactivation of TCR.

As an alternative to or in combination with this approach, the inventors have found that T-cells can be disrupted for PD1 (Programmed cell death protein 1, also known as PD1; PD-1; CD279; SLEB2; hPD-1; hPD-I or hSLE1), which is a 288 amino acid cell surface protein molecule encoded by the PDCD1 gene (NCBI—NC_000002.12). This protein is expressed on T cells and pro-B cells and has been found to negatively regulate T-cell responses (Carter L, et al., 2002). The formation of PD-1 receptor/PD-L1 ligand complex transmits an inhibitory signal, which reduces the proliferation of T-cells.

Programmed death ligand 1 (PD-L1) is a 40 kDa type 1 transmembrane protein that is deemed to play a major role in suppressing the immune system during particular events such as pregnancy, tissue allografts, autoimmune disease and other disease states such as hepatitis. PDL-1 (also called CD274 or B7H1) is encoded by CD274 gene (NCBI—NM_014143).

According to a particular aspect, the expression of both PD-1 and TCR are inhibited in the engineered T-cells of the invention, which has the dual effect of activating the T-cells as part of an allogeneic transplantation. However, the inactivation or inhibition of PD-1 can be also implemented as part of an autologous transplantation of T-cells, where the inhibition or disruption of TCR would not be required.

According to a further aspect of the invention, the inhibition or disruption of PD1 is combined with the over-expression of its ligand PDL-1 in the transplanted T-cells. This over-expression can be obtained, for instance, upon lentiviral or retroviral transformation in T-cells, in which PD-1 is inhibited or disrupted, or by any other means reported in the art. Accordingly, PDL1 that is over-expressed by the T-cells will not affect the [PD1⁻] transplanted cells, but only the [PD1⁺]T-cells from the patient. As a result, the T-cells from the patient are inhibited and do not activate against the transplanted cells, which facilitates their engraftment and persistence into the host.

According to a preferred embodiment, the invention provides engineered T-cells which are [PD1⁻][TCR⁻], while overexpressing PDL1 to facilitate their transplantation into a patient, in particular as part of an immunotherapy.

Expression of at Least One Non-Endogenous Immunosuppressive Polypeptide

According to some preferred embodiments, the inhibition of the expression of the beta-2m and/or the CIITA is carried out with an additional step of expression in said T-cell of at least one non-endogenous immunosuppressive polypeptide.

By "non-endogenous" polypeptide is meant a polypeptide not normally expressed by a donor's immune cell, preferably a polypeptide expressed by an exogenous polynucleotide that has been imported into the immune's cell genome. For instance, IL12 is not considered hereby as being a non-endogenous polypeptide because it is expressed from a preexisting gene from the donor's immune cell.

By "immunosuppressive" is meant that the expression of said non-endogenous polypeptide has the effect of alleviating the immune response of the patient host against the donor's immune cells.

The method of the present invention may thus comprise introducing into said T-cell an exogenous nucleic acid molecule comprising a nucleotide sequence coding for at least one non-endogenous immunosuppressive polypeptide, such as a viral MHC homolog or an NKG2D ligand.

Expression of Viral MHC Homolog

According to particularly preferred embodiments, said non-endogenous immunosuppressive polypeptide expressed in said T-cell is a viral MHC homolog, such as for instance UL18 (referred to as NP_044619 in the NCBI protein database).

According to these embodiments, the method of the present invention may thus comprise introducing into said T-cell an exogenous nucleic acid molecule comprising a nucleotide sequence coding for a viral MHC homolog, such as UL18. The exogenous nucleic acid molecule may comprise a nucleotide sequence coding for a polypeptide sharing at least 80%, preferably at least 90% and more preferably at least 95% of identity with SEQ ID NO: 89.

Figure 7:
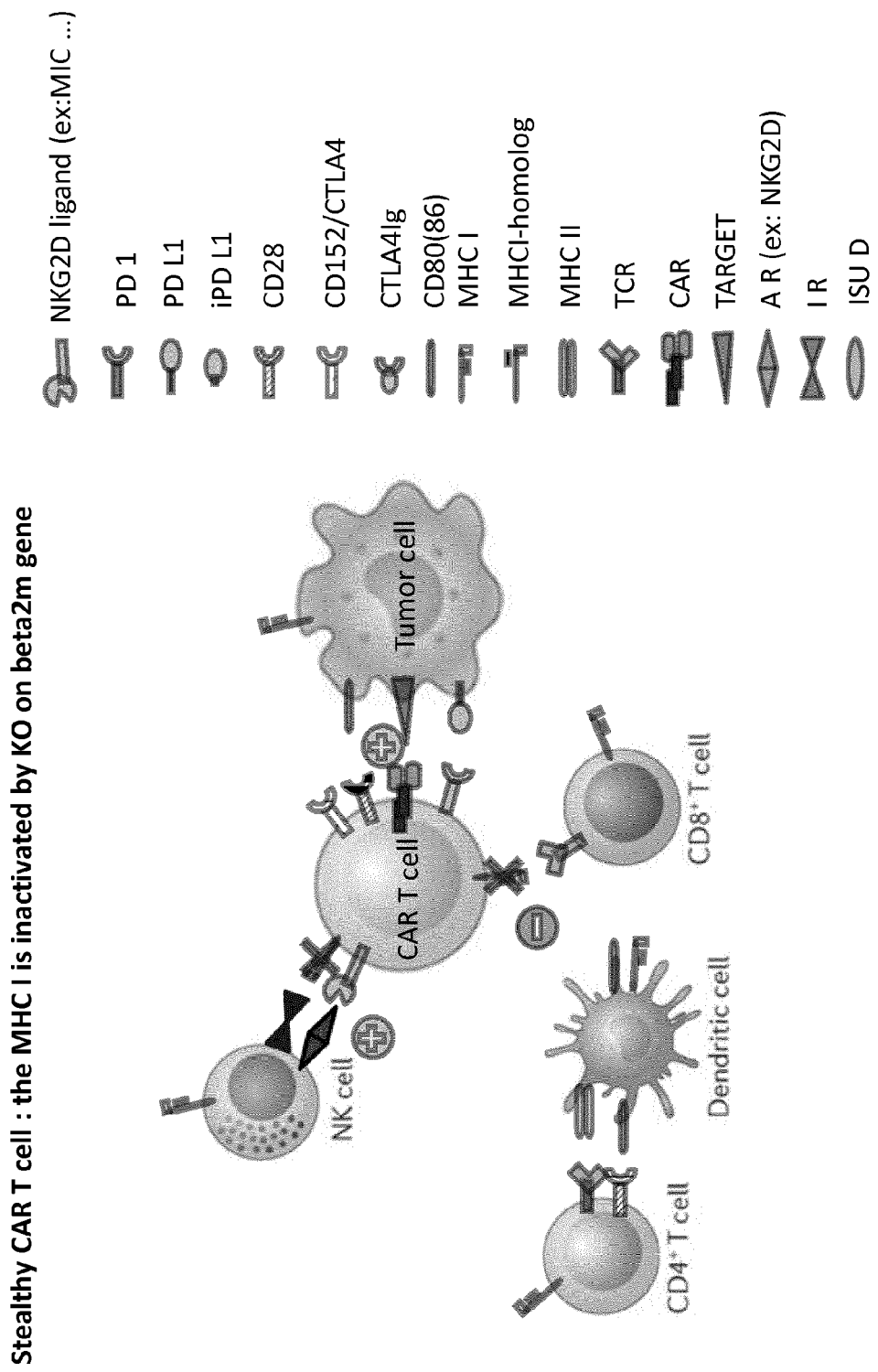
FIG. 7: Schematic representation of the potential interactions between an allogeneic CAR T cell with diverse host immune cells (CD8+ and CD4+ T cell, APC such as dendritic cell and NK cell), the CAR T cell having its B2M gene inactivated by KO. Sign (+) represents activation and sign (−) inhibition. The potential interaction between CAR T cell with the tumor cell remains unchanged. The inactivation of B2M gene which is one component of the MCHI, renders the latter non-functional in regards to the interactions with host cytotoxic T cell (CD8+) and with NK cell. Then, NK cell can exert its activation on allogeneic CAR T cell via activator pathway such NKG2D/NKG2D ligand.
Figure 8:
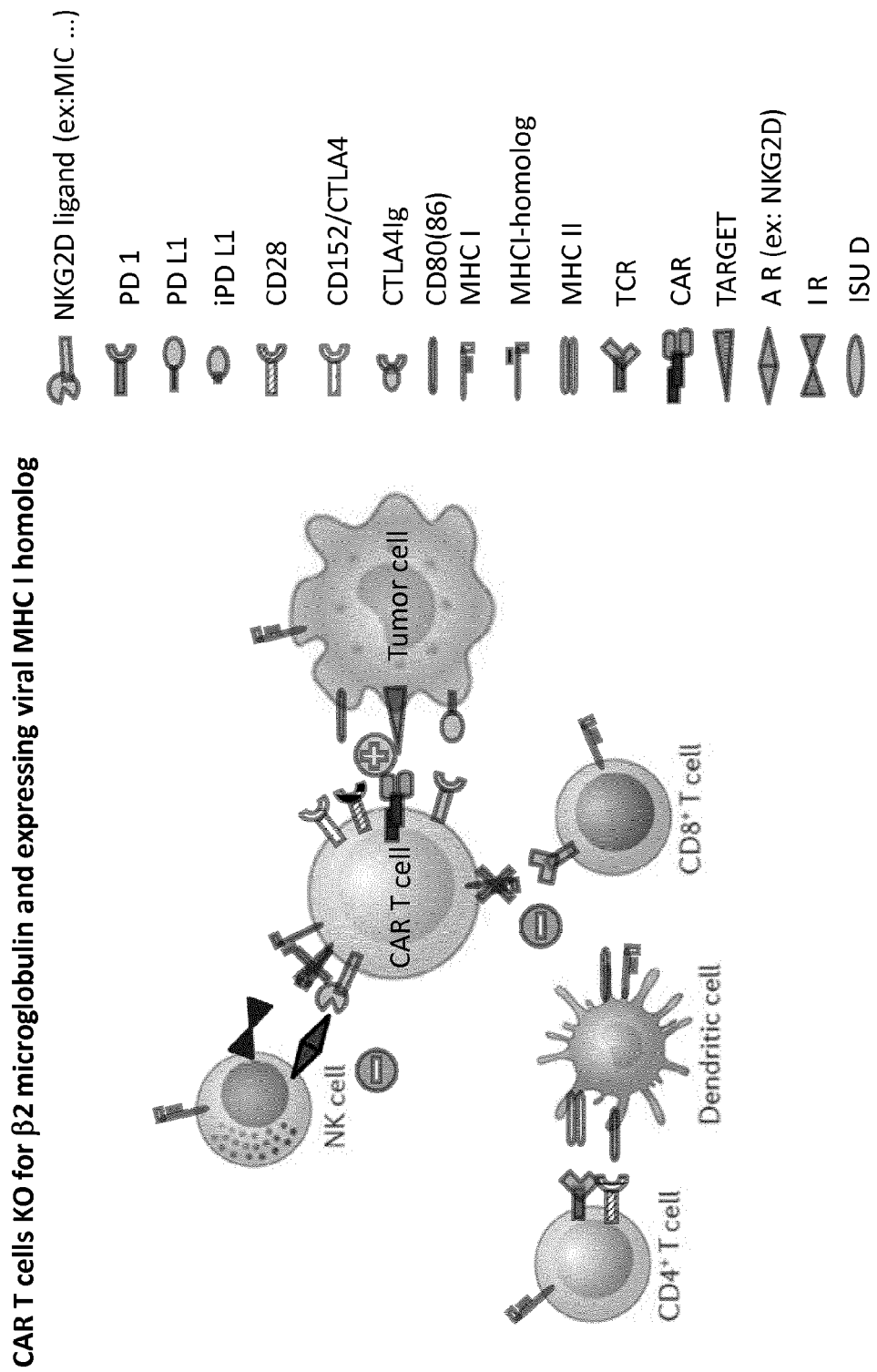
FIG. 8: Schematic representation of the potential interactions between an allogeneic CAR T cell with diverse host immune cells (CD8+ and CD4+ T cell, APC such as dendritic cell and NK cell), the CAR T cell having its B2M gene inactivated by KO and expressing viral MHCI homolog. Sign (+) represents activation and sign (−) inhibition. The potential interaction between CAR T cell with the tumor cell remains unchanged. As for the preceding figure (only B2M KO), the interaction between CAR T cell and host CD8+ T cell is alleviated. In this case, the expression of viral MHCI homolog renders the interaction with NK cell inoperative via MHCI/inhibitor receptor. The double genetic modification of allogeneic CAR T cells by KO of B2M combined with the expression of viral MHCI homolog strengthens their immunosuppressive protection.

The interaction between the allogeneic T cell and host immune cells is schematically represented in FIG. 8 (expression of viral MHC homolog) in regard to the situation to FIG. 7 (no expression). In both figures, the MHC class I is preferably inactivated by disrupting (KO) the beta2M gene.

Expression of NKG2D Ligand

Some viruses such as cytomegaloviruses have acquired mechanisms to avoid NK cell mediate immune surveillance and interfere with the NKG2D pathway by secreting a protein able to bind NKG2D ligands and prevent their surface expression (Welte, S. A.; Sinzger, C.; Lutz, S. Z.; Singh-Jasuja, H.; Sampaio, K. L; Eknigk, U.; Rammensee, H. G.; Steinle, A. 2003 "Selective intracellular retention of virally induced NKG2D ligands by the human cytomegalovirus UL16 glycoprotein". Eur. J. Immunol., 33, 194-203). In tumors cells, some mechanisms have evolved to evade NKG2D response by secreting NKG2D ligands such as ULBP2, MICB or MICA (Salih H R, Antropius H, Gieseke F, Lutz S Z, Kanz L, et al. (2003) Functional expression and release of ligands for the activating immunoreceptor NKG2D in leukemia. Blood 102: 1389-1396)

According to other particularly preferred embodiments, the non-endogenous immunosuppressive polypeptide to be expressed in said T-cell is an NKG2D ligand.

According to these embodiments, the method of the present invention may thus comprise introducing into said T-cell an exogenous nucleic acid molecule comprising a nucleotide sequence coding for an NKG2D ligand. The nucleic acid molecule may comprise a nucleotide sequence coding for a polypeptide sharing at least 80%, preferably at least 90% and more preferably at least 95% of identity with any one of SEQ ID NO: 90-97.

Figure 9:
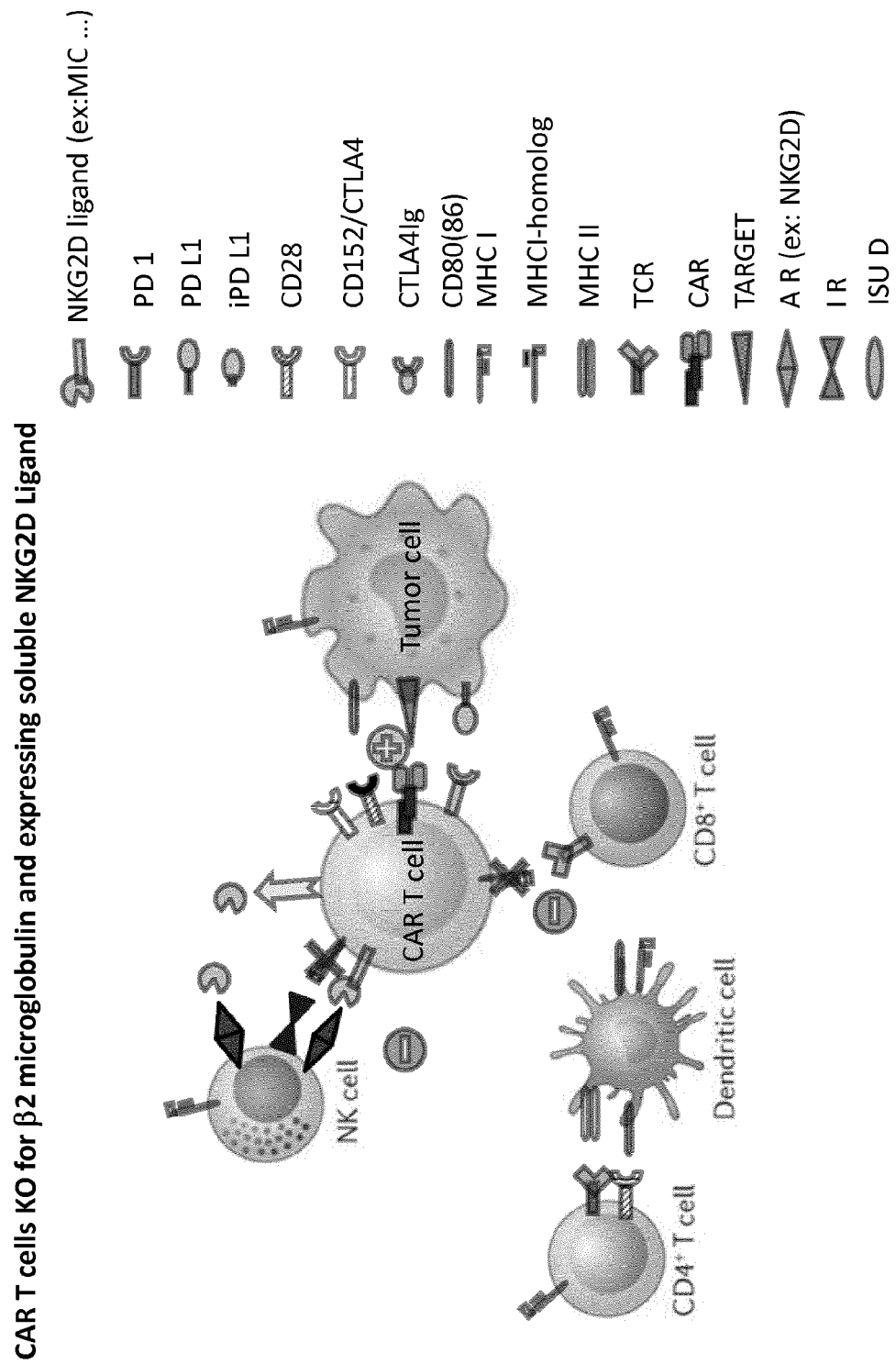
FIG. 9: Schematic representation of the potential interactions between an allogeneic CAR T cell with diverse host immune cells (CD8+ and CD4+ T cell, APC such as dendritic cell and NK cell), the CAR T cell having its B2M gene inactivated by KO and expressing a soluble NKG2D ligand. Sign (+) represents activation and sign (−) inhibition. The potential interaction between CAR T cell with the tumor cell remains unchanged. As for the preceding figure (only B2M KO), the interaction between CAR T cell and host CD8+ T cell is alleviated. The expression of soluble NKG2D ligand is another way to inactivation the interaction with NK cell. In this case, the soluble NKG2D ligand can bind to NKG2D receptor on NK cell but exerts no action, in contrast to the NKG2D ligand of CAR T cell with which it exerts an inhibitory competition. The double genetic modification of allogeneic CAR T cells by KO of B2M combined with the expression of soluble NKG2D ligand strengthens their immunosuppressive protection.

The interaction between the allogeneic T cell and host immune cells is schematically represented in FIG. 9 (expression of soluble NKG2D ligand) in regard to the situation to FIG. 7 (no expression). In both figures, the MHC class I is inactivated by disrupting (KO) the beta2M gene.

The Table 10 presented further in the text represents a viral MHC homolog (UL18) and a panel of NKG2D ligands and their polypeptide sequence to be expressed according to the present invention.

Chimeric Antigen Receptors (CARs)

Adoptive immunotherapy, which involves the transfer of autologous antigen-specific T-cells generated ex vivo, is a promising strategy to treat cancer or viral infections. The T-cells used for adoptive immunotherapy can be generated either by expansion of antigen-specific T cells or redirection of T cells through genetic engineering (Park, Rosenberg et al. 2011). Transfer of viral antigen specific T-cells is a well-established procedure used for the treatment of transplant associated viral infections and rare viral-related malignancies. Similarly, isolation and transfer of tumor specific T cells has been shown to be successful in treating melanoma.

Novel specificities in T-cells have been successfully generated through the genetic transfer of transgenic T-cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T-cells. CARs have successfully allowed T-cells to be redirected against antigens expressed at the surface of tumor cells from various malignancies including lymphomas and solid tumors (Jena, Dotti et al. 2010).

CD19 is an attractive target for immunotherapy because the vast majority of B-acute lymphoblastic leukemia (B-ALL) uniformly express CD19, whereas expression is absent on non hematopoietic cells, as well as myeloid, erythroid, and T cells, and bone marrow stem cells. Clinical trials targeting CD19 on B-cell malignancies are underway with encouraging anti-tumor responses. Most infuse T cells genetically modified to express a chimeric antigen receptor (CAR) with specificity derived from the scFv region of a CD19-specific mouse monoclonal antibody FMC63 (WO2013/126712).

Therefore, in accordance with certain embodiments, the Chimeric Antigen Receptor expressed by the engineered T-cell is directed against the B-lymphocyte antigen CD19.

In accordance with certain embodiments, the Chimeric Antigen Receptor is a single chain Chimeric Antigen Receptor. As an example of single-chain Chimeric Antigen Receptor to be expressed in the engineered T-cells according to the present invention is a single polypeptide that comprises at least one extracellular ligand binding domain, a transmembrane domain and at least one signal transducing domain, wherein said extracellular ligand binding domain comprises a scFV derived from the specific anti-CD19 monoclonal antibody 4G7. Once transduced into the T-cell, for instance by using retroviral or lentiviral transduction, this CAR contributes to the recognition of CD19 antigen present at the surface of malignant B-cells involved in lymphoma or leukemia.

In accordance with particular embodiments, the Chimeric Antigen Receptor is a polypeptide comprising the amino acid sequence forth in SEQ ID NO: 6 or a variant thereof comprising an amino acid sequence that has at least 70%, such as at least 80%, at least 90%, at least 95%, or at least 99%, sequence identity with the amino acid sequence set forth in SEQ ID NO: 6 over the entire length of SEQ ID NO: 6. Preferably, the variant is capable of binding CD19.

A particularly preferred Chimeric Antigen Receptor is a polypeptide comprising the amino acid sequence set forth in SEQ ID NO: 7 or a variant thereof comprising an amino acid sequence that has at least 80%, such as at least 90%, at least 95%, or at least 99%, sequence identity with the amino acid sequence set forth in SEQ ID NO: 7 over the entire length of SEQ ID NO: 7. Such variant may differ from the polypeptide set forth in SEQ ID NO: 7 in the substitution of at least one, at least two or at least three amino acid residue(s). Preferably, said variant is capable of binding CD19.

In accordance with other certain embodiments, the Chimeric Antigen Receptor may be directed against another antigen expressed at the surface of a malignant or infected cell, such as a cluster of differentiation molecule, such as CD16, CD64, CD78, CD96, CLL1, CD116, CD117, CD71, CD45, CD71, CD123 and CD138, a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialoganglioside GD2, ductal-epithelial mucine, gp36, TAG-72, glycosphingolipids, glioma-associated antigen, 1-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostase specific antigen (PSA), PAP, NY-ESO-1, LAGA-1a, p53, prostein, PSMA, surviving and telomerase, prostate-carcinoma tumor antigen-1 (PCTA-1), MAGE, ELF2M, neutrophil elastase, ephrin B2, CD22, insulin growth factor (IGF1)-I, IGF-II, IGFI receptor, mesothelin, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the A1 domain of tenascin-C (TnC A1) and fibroblast associated protein (fap); a lineage-specific or tissue specific antigen such as CD3, CD4, CD8, CD24, CD25, CD33, CD34, CD133, CD138, CTLA-4, B7-1 (CD80), B7-2 (CD86), GM-CSF, cytokine receptors, endoglin, a major histocompatibility complex (MHC) molecule, BCMA (CD269, TNFRSF 17), multiple myeloma or lymphoblastic leukaemia antigen, such as one selected from TNFRSF17 (UNIPROT Q02223), SLAMF7 (UNIPROT Q9NQ25), GPRC5D (UNIPROT Q9NZD1), FKBP11 (UNIPROT Q9NYL4), KAMP3, ITGA8 (UNIPROT P53708), and FCRL5 (UNIPROT Q68SN8). a virus-specific surface antigen such as an HIV-specific antigen (such as HIV gp120); an EBV-specific antigen, a CMV-specific antigen, a HPV-specific antigen, a Lasse Virus-specific antigen, an Influenza Virus-specific antigen as well as any derivate or variant of these surface antigens.

In other certain embodiments, the Chimeric Antigen Receptor is a multi-chain Chimeric Antigen Receptor. Chimeric Antigen Receptors from the prior art introduced in T-cells have been formed of single chain polypeptides that necessitate serial appending of signaling domains. However, by moving signaling domains from their natural juxtamembrane position may interfere with their function. To overcome this drawback, the applicant recently designed a multi-chain CAR derived from FcεRI to allow normal juxtamembrane position of all relevant signaling domains. In this new architecture, the high affinity IgE binding domain of FcεRI alpha chain is replaced by an extracellular ligand-binding domain such as scFv to redirect T-cell specificity against cell targets and the N and/or C-termini tails of FcεRI beta chain are used to place costimulatory signals in normal juxtamembrane positions as described in WO 2013/176916.

Accordingly, a CAR expressed by the engineered T-cell according to the invention can be a multi-chain chimeric antigen receptor particularly adapted to the production and expansion of engineered T-cells of the present invention. Such multi-chain CARs comprise at least two of the following components:

a) one polypeptide comprising the transmembrane domain of FcεRI alpha chain and an extracellular ligand-binding domain,
b) one polypeptide comprising a part of N- and C-terminal cytoplasmic tail and the transmembrane domain of FcεRI beta chain and/or
c) at least two polypeptides comprising each a part of intracytoplasmic tail and the transmembrane domain of FcεRI gamma chain, whereby different polypeptides multimerize together spontaneously to form dimeric, trimeric or tetrameric CAR.

According to such architectures, ligands binding domains and signaling domains are born on separate polypeptides. The different polypeptides are anchored into the membrane in a close proximity allowing interactions with each other. In such architectures, the signaling and co-stimulatory domains can be in juxtamembrane positions (i.e. adjacent to the cell membrane on the internal side of it), which is deemed to allow improved function of co-stimulatory domains. The multi-subunit architecture also offers more flexibility and possibilities of designing CARs with more control on T-cell activation. For instance, it is possible to include several extracellular antigen recognition domains having different specificity to obtain a multi-specific CAR architecture. It is also possible to control the relative ratio between the different subunits into the multi-chain CAR. This type of architecture has been recently detailed by the applicant in PCT/US2013/058005.

The assembly of the different chains as part of a single multi-chain CAR is made possible, for instance, by using the different alpha, beta and gamma chains of the high affinity receptor for IgE (FcεRI) (Metzger, Alcaraz et al. 1986) to which are fused the signaling and co-stimulatory domains. The gamma chain comprises a transmembrane region and cytoplasmic tail containing one immunoreceptor tyrosine-based activation motif (ITAM) (Cambier 1995).

The multi-chain CAR can comprise several extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the multi-chain CAR.

The signal transducing domain or intracellular signaling domain of the multi-chain CAR(s) of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the multi-chain CAR is expressed. For example, the effector function of a T cell can be a cytolytic activity or helper activity including the secretion of cytokines.

In the present application, the term "signal transducing domain" refers to the portion of a protein which transduces the effector signal function signal and directs the cell to perform a specialized function.

Preferred examples of signal transducing domain for use in single or multi-chain CAR can be the cytoplasmic sequences of the Fc receptor or T cell receptor and co-receptors that act in concert to initiate signal transduction following antigen receptor engagement, as well as any derivate or variant of these sequences and any synthetic sequence that as the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. According to particular embodiments, the signaling transducing domain of the multi-chain CAR can comprise the CD3zeta signaling domain, or the intracytoplasmic domain of the FcεRI beta or gamma chains.

According to particular embodiments, the signal transduction domain of multi-chain CARs of the present invention comprises a co-stimulatory signal molecule. A co-stimulatory molecule is a cell surface molecule other than an antigen receptor or their ligands that is required for an efficient immune response.

Ligand binding-domains can be any antigen receptor previously used, and referred to, with respect to single-chain CAR referred to in the literature, in particular scFv from monoclonal antibodies.

Engineered T-Cells

As a result of the present invention, engineered T-cells can be obtained having improved characteristics. In particular, the present invention provides an engineered, preferably isolated, T-cell which is characterized in that the expression of B2M and/or CIITA is inhibited.

According to certain embodiments, the present invention provides an engineered, preferably isolated, T-cell which expresses a rare-cutting endonuclease able to selectively inactivate by DNA cleavage, preferably double-strand break, the gene encoding B2M. According to particular embodiments, said T-cell comprises an exogenous nucleic acid molecule comprising a nucleotide sequence encoding said rare-cutting endonuclease. According to more particular embodiments, said rare-cutting endonuclease is a TAL-nuclease, meganuclease, zinc-finger nuclease (ZFN), or RNA guided endonuclease. Hence, in accordance with a specific embodiment, the rare-cutting endonuclease is a TAL-nuclease. In accordance with another specific embodiment, the rare-cutting endonuclease is a meganuclease. In accordance with another specific embodiment, the rare-cutting endonuclease is a zinc-finger nuclease. In accordance with yet another specific embodiment, the rare-cutting endonuclease is a RNA guided endonuclease, such as Cas9.

According to certain other embodiments, the present invention provides an engineered, preferably isolated, T-cell which comprises an exogenous nucleic acid molecule that inhibits the expression of B2M. According to particular embodiments, said T-cell comprises an exogenous nucleic acid molecule comprising a nucleotide sequence encoding a nucleic acid molecule that inhibits the expression of B2M. According to more particular embodiments, the nucleic acid molecule that inhibits the expression of B2M is an antisense oligonucleotide, ribozyme or interfering RNA (RNAi) molecule. Hence, in accordance with a specific embodiment, nucleic acid molecule that inhibits the expression of B2M is an antisense oligonucleotide. In accordance with another specific embodiment, nucleic acid molecule that inhibits the expression of B2M is a ribozyme, and preferably a hammerhead riboyzme. In accordance with another specific embodiment, nucleic acid molecule that inhibits the expression of B2M is an interfering RNA molecule.

According to certain embodiments, the present invention provides an engineered, preferably isolated, T-cell which expresses a rare-cutting endonuclease able to selectively inactivate by DNA cleavage, preferably double-strand break, the gene encoding CIITA. According to particular embodiments, said T-cell comprises an exogenous nucleic acid molecule comprising a nucleotide sequence encoding said rare-cutting endonuclease. According to more particular embodiments, said rare-cutting endonuclease is a TAL-nuclease, meganuclease, zinc-finger nuclease (ZFN), or RNA guided endonuclease. Hence, in accordance with a specific embodiment, the rare-cutting endonuclease is a TAL-nuclease. In accordance with another specific embodiment, the rare-cutting endonuclease is a meganuclease. In accordance with another specific embodiment, the rare-cutting endonuclease is a zinc-finger nuclease. In accordance with yet another specific embodiment, the rare-cutting endonuclease is a RNA or DNA guided endonuclease, such as Cas9 or Argonaute.

According to certain other embodiments, the present invention provides an engineered, preferably isolated, T-cell which comprises an exogenous nucleic acid molecule that inhibits the expression of CIITA. According to particular embodiments, said T-cell comprises an exogenous nucleic acid molecule comprising a nucleotide sequence encoding a nucleic acid molecule that inhibits the expression of CIITA. According to more particular embodiments, the nucleic acid molecule that inhibits the expression of CIITA is an antisense oligonucleotide, ribozyme or interfering RNA (RNAi) molecule. Hence, in accordance with a specific embodiment, nucleic acid molecule that inhibits the expression of CIITA is an antisense oligonucleotide. In accordance with another specific embodiment, nucleic acid molecule that inhibits the expression of CIITA is a ribozyme, and preferably a hammerhead riboyzme. In accordance with another specific embodiment, nucleic acid molecule that inhibits the expression of CIITA is an interfering RNA molecule.

According to certain embodiments, the engineered T-cell further expresses a rare-cutting endonuclease able to selectively inactivate by DNA cleavage, preferably double-strand break, at least one gene coding for a component of the T-cell receptor (TCR), such as TCR alpha. According to particular embodiments, said T-cell comprises an exogenous nucleic acid molecule comprising a nucleotide sequence encoding said rare-cutting endonuclease.

According to certain embodiments, the engineered T-cell further comprises expresses a Chimeric Antigen Receptor (CAR) directed against at least one antigen expressed at the surface of a malignant or infected cell. According to particular embodiments, said T-cell comprises an exogenous nucleic acid molecule comprising a nucleotide sequence encoding said CAR.

According to some embodiments, the present invention provides an engineered, preferably isolated, T-cell which expresses at least one non-endogenous immune-suppressive polypeptide.

According to particular embodiments, said non-endogenous immune-suppressive polypeptide is a viral MHC homolog, such as UL18. The T-cell may thus comprise an exogenous nucleic acid molecule comprising a nucleotide sequence coding for a polypeptide sharing at least 80%, preferably at least 90% and more preferably at least 95% of identity with SEQ ID NO: 89. According to other particular embodiments, said non-endogenous immune-suppressive polypeptide is a NKG2D ligand. The T-cell may thus comprise an exogenous nucleic acid molecule comprising a nucleotide sequence coding for a polypeptide sharing at least 80%, preferably at least 90% and more preferably at least 95% of identity with any one of SEQ ID NO: 90-97.

It is understood that the details given herein in particularly with respect to the rare-cutting endonuclease able to selectively inactivate by DNA cleavage the gene encoding B2M, the nucleic acid molecule that inhibits the expression of B2M, the rare-cutting endonuclease able to selectively inactivate by DNA cleavage at least one gene coding for a component of the T-cell receptor (TCR), and the Chimeric Antigen Receptor also apply to this aspect of the invention.

Further, in the scope of the present invention is also encompassed a cell or cell line obtained from an engineered T-cell according to the invention, preferably displaying one of these phenotypes:

[b2m]$^-$[TCR]$^-$
[TCR]$^-$[PD1]$^-$[PDL-1]$^+$
[b2m]$^-$[TCR]$^-$[PD1]$^-$
[b2m]$^-$[TCR]$^-$[PD1]$^-$[PDL-1]$^+$
[b2m]$^-$[viral MHC homolog]$^+$
[b2m]$^-$[TCR]$^-$[viral MHC homolog]$^+$
[b2m]$^-$[NKG2D ligand]$^+$
[b2m]$^-$[TCR]$^-$[NKG2D ligand]$^+$ The T cells according to the present invention are preferably [CAR]$^+$—i.e. armed with a chimeric antigen receptor to direct the specific recognition of tumor cells.

Delivery Methods

The inventors have considered any means known in the art to allow delivery inside cells or subcellular compartments of said cells the nucleic acid molecules employed in accordance with the invention. These means include viral transduction, electroporation and also liposomal delivery means, polymeric carriers, chemical carriers, lipoplexes, polyplexes, dendrimers, nanoparticles, emulsion, natural endocytosis or phagocytose pathway as non-limiting examples.

In accordance with the present invention, the nucleic acid molecules detailed herein may be introduced in the T-cell by any suitable methods known in the art. Suitable, non-limiting methods for introducing a nucleic acid molecule into a T-cell according include stable transformation methods, wherein the nucleic acid molecule is integrated into the genome of the cell, transient transformation methods wherein the nucleic acid molecule is not integrated into the genome of the cell and virus mediated methods. Said nucleic acid molecule may be introduced into a cell by, for example, a recombinant viral vector (e.g., retroviruses, adenoviruses), liposome and the like. Transient transformation methods include, for example, microinjection, electroporation or particle bombardment. In certain embodiments, the nucleic acid molecule is a vector, such as a viral vector or plasmid. Suitably, said vector is an expression vector enabling the expression of the respective polypeptide(s) or protein(s) detailed herein by the T-cell.

A nucleic acid molecule introduced into the T-cell may be DNA or RNA. In certain embodiments, a nucleic acid molecule introduced into the T-cell is DNA. In certain embodiments, a nucleic acid molecule introduced into the T-cell is RNA, and in particular an mRNA encoding a polypeptide or protein detailed herein, which mRNA is introduced directly into the T-cell, for example by electroporation. A suitable electroporation technique is described, for example, in International Publication WO2013/176915 (in particular the section titled "Electroporation" bridging pages 29 to 30). A particular nucleic acid molecule which may be an mRNA is the nucleic acid molecule comprising a nucleotide sequence coding for a rare-cutting endonuclease able to selectively inactivate by DNA cleavage the gene encoding B2M. Another particular nucleic acid molecule which may be an mRNA is the nucleic acid molecule comprising a nucleotide sequence coding for a rare-cutting endonuclease able to selectively inactivate by DNA cleavage the gene encoding CIITA. A yet other particular nucleic acid molecule which may be an mRNA is the nucleic acid molecule comprising a nucleotide sequence coding for a rare-cutting endonuclease able to selectively inactivate by DNA cleavage at least one gene coding for one component of the T-Cell Receptor (TCR).

As a preferred embodiment of the invention, nucleic acid molecules encoding the endonucleases of the present invention are transfected under mRNA form in order to obtain transient expression and avoid chromosomal integration of foreign DNA, for example by electroporation. The inventors have determined different optimal conditions for mRNA electroporation in T-cell displayed in Table 1. The inventor used the cytoPulse technology which allows, by the use of pulsed electric fields, to transiently permeabilize living cells for delivery of material into the cells (U.S. Pat. No. 6,010,613 and WO 2004/083379). Pulse duration, intensity as well as the interval between pulses can be modified in order to reach the best conditions for high transfection efficiency with minimal mortality. Basically, the first high electric field pulses allow pore formation, while subsequent lower electric field pulses allow to moving the polynucleotide into the cell. In one aspect of the present invention, the inventor describe the steps that led to achievement of >95% transfection efficiency of mRNA in T cells, and the use of the electroporation protocol to transiently express different kind of proteins in T cells. In particular the invention relates to a method of transforming T cell comprising contacting said T cell with RNA and applying to T cell an agile pulse sequence consisting of:
  (a) one electrical pulse with a voltage range from 2250 to 3000 V per centimeter, a pulse width of 0.1 ms and a pulse interval of 0.2 to 10 ms between the electrical pulses of step (a) and (b);
  (b) one electrical pulse with a voltage range from 2250 to 3000 V with a pulse width of 100 ms and a pulse interval of 100 ms between the electrical pulse of step (b) and the first electrical pulse of step (c); and
  (c) 4 electrical pulses with a voltage of 325 V with a pulse width of 0.2 ms and a pulse interval of 2 ms between each of 4 electrical pulses.

In particular embodiment, the method of transforming T cell comprising contacting said T cell with RNA and applying to T cell an agile pulse sequence consisting of:
  (a) one electrical pulse with a voltage of 2250, 2300, 2350, 2400, 2450, 2500, 2550, 2400, 2450, 2500, 2600, 2700, 2800, 2900 or 3000V per centimeter, a pulse width of 0.1 ms and a pulse interval of 0.2, 0.5, 1, 2, 3, 4, 5, 6, 7, 8, 9 or 10 ms between the electrical pulses of step (a) and (b);
  (b) one electrical pulse with a voltage range from 2250, of 2250, 2300, 2350, 2400, 2450, 2500, 2550, 2400, 2450, 2500, 2600, 2700, 2800, 2900 or 3000V with a pulse width of 100 ms and a pulse interval of 100 ms between the electrical pulse of step (b) and the first electrical pulse of step (c); and
  (c) 4 electrical pulses with a voltage of 325 V with a pulse width of 0.2 ms and a pulse interval of 2 ms between each of 4 electrical pulses.

Any values included in the value range described above are disclosed in the present application. Electroporation medium can be any suitable medium known in the art. Preferably, the electroporation medium has conductivity in a range spanning 0.01 to 1.0 milliSiemens.

TABLE 1

Different cytopulse programs used to determine the minimal voltage required for electroporation in PBMC derived T-cells.

| Cyto-pulse program | Group 1 | | | | Group 2 | | | | Group 3 | | | |
|---|---|---|---|---|---|---|---|---|---|---|---|---|
| | Pulses | V | duration (ms) | Interval (ms) | Pulses | V | duration (ms) | Interval (ms) | Pulses | V | duration (ms) | Interval (ms) |
| 1 | 1 | 600 | 0.1 | 0.2 | 1 | 600 | 0.1 | 100 | 4 | 130 | 0.2 | 2 |
| 2 | 1 | 900 | 0.1 | 0.2 | 1 | 900 | 0.1 | 100 | 4 | 130 | 0.2 | 2 |
| 3 | 1 | 1200 | 0.1 | 0.2 | 1 | 1200 | 0.1 | 100 | 4 | 130 | 0.2 | 2 |
| 4 | 1 | 1200 | 0.1 | 10 | 1 | 900 | 0.1 | 100 | 4 | 130 | 0.2 | 2 |
| 5 | 1 | 900 | 0.1 | 20 | 1 | 600 | 0.1 | 100 | 4 | 130 | 0.2 | 2 |

Non Alloreactive T-Cells:

Although the method of the invention could be carried out in-vivo as part of a gene therapy, for instance, by using viral vectors targeting T-cells in blood circulation, which would include genetic sequences expressing a specific rare-cutting endonuclease along with other genetic sequences expressing, e.g., a CAR, the method of the invention is more generally intended to be practiced ex-vivo on cultured T-cells obtainable from patients or donors. The engineered T-cells engineered ex-vivo can be either re-implanted into a patient from where they originate, as part of an autologous treatment, or to be used as part of an allogeneic treatment. In this later case, it is preferable to further engineer the cells to make them non-alloreactive to ensure their proper engraftment. Accordingly, the method of the invention may include additional steps of procuring the T-cells from a donor and to inactivate genes thereof involved in MHC recognition and or being targets of immunosuppressive drugs such as described for instance in WO 2013/176915.

T-cell receptors (TCR) are cell surface receptors that participate in the activation of T-cells in response to the presentation of antigen. The TCR is generally made from two chains, alpha and beta, which assemble to form a heterodimer and associates with the CD3-transducing subunits to form the T-cell receptor complex present on the cell surface. Each alpha and beta chain of the TCR consists of an immunoglobulin-like N-terminal variable (V) and constant (C) region, a hydrophobic transmembrane domain, and a short cytoplasmic region. As for immunoglobulin molecules, the variable region of the alpha and beta chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of GVHD. It has been shown that normal surface expression of the TCR depends on the coordinated synthesis and assembly of all seven components of the complex (Ashwell and Klusner 1990). The inactivation of TCR alpha or TCR beta can result in the elimination of the TCR from the surface of T cells preventing recognition of alloantigen and thus GVHD.

Thus, still according to the invention, engraftment of the T-cells may be improved by inactivating at least one gene encoding a TCR component. TCR is rendered not functional in the cells by inactivating TCR alpha gene and/or TCR beta gene(s).

With respect to the use of Cas9/CRISPR system, the inventors have determined appropriate target sequences within the 3 exons encoding TCR, allowing a significant reduction of toxicity in living cells, while retaining cleavage efficiency. The preferred target sequences are noted in Table 2 (+ for lower ratio of TCR negative cells, ++ for intermediate ratio, +++ for higher ratio).

TABLE 2 appropriate target sequences for the guide RNA using Cas9 in T-cells

| Exon TCR | Position | Strand | Target genomic sequence | SEQ ID | efficiency |
|---|---|---|---|---|---|
| Ex1 | 78 | -1 | GAGAATCAAAATCGGTGAATAGG | 8 | +++ |
| Ex3 | 26 | 1 | TTCAAAACCTGTCAGTGATTGGG | 9 | +++ |
| Ex1 | 153 | 1 | TGTGCTAGACATGAGGTCTATGG | 10 | +++ |
| Ex3 | 74 | -1 | CGTCATGAGCAGATTAAACCCGG | 11 | +++ |
| Ex1 | 4 | -1 | TCAGGGTTCTGGATATCTGTGGG | 12 | +++ |
| Ex1 | 5 | -1 | GTCAGGGTTCTGGATATCTGTGG | 13 | +++ |
| Ex3 | 33 | -1 | TTCGGAACCCAATCACTGACAGG | 14 | +++ |
| Ex3 | 60 | -1 | TAAACCCGGCCACTTTCAGGAGG | 15 | +++ |
| Ex1 | 200 | -1 | AAAGTCAGATTTGTTGCTCCAGG | 16 | ++ |
| Ex1 | 102 | 1 | AACAAATGTGTCACAAAGTAAGG | 17 | ++ |

TABLE 2-continued appropriate target sequences
for the guide RNA using Cas9 in T-cells

| Exon TCR | Position | Strand | Target genomic sequence | SEQ ID | efficiency |
|---|---|---|---|---|---|
| Ex1 | 39 | -1 | TGGATTTAGAGTCTCTCAGCTGG | 18 | ++ |
| Ex1 | 59 | -1 | TAGGCAGACAGACTTGTCACTGG | 19 | ++ |
| Ex1 | 22 | -1 | AGCTGGTACACGGCAGGGTCAGG | 20 | ++ |
| Ex1 | 21 | -1 | GCTGGTACACGGCAGGGTCAGGG | 21 | ++ |
| Ex1 | 28 | -1 | TCTCTCAGCTGGTACACGGCAGG | 22 | ++ |
| Ex3 | 25 | 1 | TTTCAAAACCTGTCAGTGATTGG | 23 | ++ |
| Ex3 | 63 | -1 | GATTAAACCCGGCCACTTTCAGG | 24 | ++ |
| Ex2 | 17 | -1 | CTCGACCAGCTTGACATCACAGG | 25 | ++ |
| Ex1 | 32 | -1 | AGAGTCTCTCAGCTGGTACACGG | 26 | ++ |
| Ex1 | 27 | -1 | CTCTCAGCTGGTACACGGCAGGG | 27 | ++ |
| Ex2 | 12 | 1 | AAGTTCCTGTGATGTCAAGCTGG | 28 | ++ |
| Ex3 | 55 | 1 | ATCCTCCTCCTGAAAGTGGCCGG | 29 | ++ |
| Ex3 | 86 | 1 | TGCTCATGACGCTGCGGCTGTGG | 30 | ++ |
| Ex1 | 146 | 1 | ACAAAACTGTGCTAGACATGAGG | 31 | + |
| Ex1 | 86 | -1 | ATTTGTTTGAGAATCAAAATCGG | 32 | + |
| Ex2 | 3 | -1 | CATCACAGGAACTTTCTAAAAGG | 33 | + |
| Ex2 | 34 | 1 | GTCGAGAAAAGCTTTGAAACAGG | 34 | + |
| Ex3 | 51 | -1 | CCACTTTCAGGAGGAGGATTCGG | 35 | + |
| Ex3 | 18 | -1 | CTGACAGGTTTTGAAAGTTTAGG | 36 | + |
| Ex2 | 43 | 1 | AGCTTTGAAACAGGTAAGACAGG | 37 | + |
| Ex1 | 236 | -1 | TGGAATAATGCTGTTGTTGAAGG | 38 | + |
| Ex1 | 182 | 1 | AGAGCAACAGTGCTGTGGCCTGG | 39 | + |
| Ex3 | 103 | 1 | CTGTGGTCCAGCTGAGGTGAGGG | 40 | + |
| Ex3 | 97 | 1 | CTGCGGCTGTGGTCCAGCTGAGG | 41 | + |
| Ex3 | 104 | 1 | TGTGGTCCAGCTGAGGTGAGGGG | 42 | + |
| Ex1 | 267 | 1 | CTTCTTCCCCAGCCCAGGTAAGG | 43 | + |
| Ex1 | 15 | -1 | ACACGGCAGGGTCAGGGTTCTGG | 44 | + |
| Ex1 | 177 | 1 | CTTCAAGAGCAACAGTGCTGTGG | 45 | + |
| Ex1 | 256 | -1 | CTGGGGAAGAAGGTGTCTTCTGG | 46 | + |
| Ex3 | 56 | 1 | TCCTCCTCCTGAAAGTGGCCGGG | 47 | + |
| Ex3 | 80 | 1 | TTAATCTGCTCATGACGCTGCGG | 48 | + |
| Ex3 | 57 | -1 | ACCCGGCCACTTTCAGGAGGAGG | 49 | + |
| Ex1 | 268 | 1 | TTCTTCCCCAGCCCAGGTAAGGG | 50 | + |
| Ex1 | 266 | -1 | CTTACCTGGGCTGGGGAAGAAGG | 51 | + |
| Ex1 | 262 | 1 | GACACCTTCTTCCCCAGCCCAGG | 52 | + |

TABLE 2-continued appropriate target sequences
for the guide RNA using Cas9 in T-cells

| Exon TCR | Position | Strand | Target genomic sequence | SEQ ID | efficiency |
|---|---|---|---|---|---|
| Ex3 | 102 | 1 | GCTGTGGTCCAGCTGAGGTGAGG | 53 | + |
| Ex3 | 51 | 1 | CCGAATCCTCCTCCTGAAAGTGG | 54 | + |

MHC antigens are also proteins that played a major role in transplantation reactions. Rejection is mediated by T cells reacting to the histocompatibility antigens on the surface of implanted tissues, and the largest group of these antigens is the major histocompatibility antigens (MHC). These proteins are expressed on the surface of all higher vertebrates and are called HLA antigens (for human leukocyte antigens) in human cells. Like TCR, the MHC proteins serve a vital role in T cell stimulation. Antigen presenting cells (often dendritic cells) display peptides that are the degradation products of foreign proteins on the cell surface on the MHC. In the presence of a co-stimulatory signal, the T cell becomes activated, and will act on a target cell that also displays that same peptide/MHC complex. For example, a stimulated T helper cell will target a macrophage displaying an antigen in conjunction with its MHC, or a cytotoxic T cell (CTL) will act on a virally infected cell displaying foreign viral peptides.

Thus, in order to provide less alloreactive T-cells, the method of the invention can further comprise the step of inactivating or mutating one HLA gene.

The class I HLA gene cluster in humans comprises three major loci, B, C and A, as well as several minor loci. The class II HLA cluster also comprises three major loci, DP, DQ and DR, and both the class I and class II gene clusters are polymorphic, in that there are several different alleles of both the class I and II genes within the population. There are also several accessory proteins that play a role in HLA functioning as well. The Tap1 and Tap2 subunits are parts of the TAP transporter complex that is essential in loading peptide antigens on to the class I HLA complexes, and the LMP2 and LMP7 proteosome subunits play roles in the proteolytic degradation of antigens into peptides for display on the HLA. Reduction in LMP7 has been shown to reduce the amount of MHC class I at the cell surface, perhaps through a lack of stabilization (Fehling et al. (1999) Science 265:1234-1237). In addition to TAP and LMP, there is the tapasin gene, whose product forms a bridge between the TAP complex and the HLA class I chains and enhances peptide loading. Reduction in tapasin results in cells with impaired MHC class I assembly, reduced cell surface expression of the MHC class I and impaired immune responses (Grandea et al. (2000) Immunity 13:213-222 and Garbi et al. (2000) Nat. Immunol. 1:234-238). Any of the above genes may be inactivated as part of the present invention as disclosed, for instance in WO 2012/012667.

Hence, in accordance with certain embodiments, the method of the invention further comprises inactivating at least one gene selected from the group consisting of RFXANK, RFX5, RFXAP, TAP1, TAP2, ZXDA, ZXDB and ZXDC. Inactivation may, for instance, be achieved by using a genome modification, more particularly through the expression in the T-cell of a rare-cutting endonuclease able to selectively inactivate by DNA cleavage a gene selected from the group consisting of RFXANK, RFX5, RFXAP, TAP1, TAP2, ZXDA, ZXDB and ZXDC.

Activation and Expansion of T Cells

The method according to the invention may include a further step of activating and/or expanding the T-cell(s). This can be done prior to or after genetic modification of the T-cell(s), using the methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. According to these methods, the T cells of the invention can be expanded by contact with a surface having attached thereto an agent that stimulates a CD3 TCR complex associated signal and a ligand that stimulates a co-stimulatory molecule on the surface of the T cells.

In particular, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. For example, the agents providing each signal may be in solution or coupled to a surface. As those of ordinary skill in the art can readily appreciate, the ratio of particles to cells may depend on particle size relative to the target cell. In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. Cell surface proteins may be ligated by allowing paramagnetic beads to which anti-CD3 and anti-CD28 are attached (3×28 beads) to contact the T cells. In one embodiment the cells (for example, 4 to 10 T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. The mixture may be cultured for several hours (about 3 hours) to about 14 days or any hourly integer value in between. In another embodiment, the mixture may be cultured for 21 days. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Therapeutic Applications

The T-cells obtainable in accordance with the present invention are intended to be used as a medicament, and in particular for treating, among others, cancer, infections (such viral infections) or immune diseases in a patient in need thereof. Accordingly, the present invention provides engineered T-cells for use as a medicament. Particularly, the present invention provides engineered T-cells for use in the treatment of a cancer, such as lymphoma, or viral infection. Also provided are compositions, particularly pharmaceutical compositions, which comprise at least one engineered T-cell of the present invention. In certain embodiments, a composition may comprise a population of engineered T-cell of the present invention.

The treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

The invention is particularly suited for allogenic immunotherapy, insofar as it enables the transformation of T-cells, typically obtained from donors, into non-alloreactive cells. This may be done under standard protocols and reproduced as many times as needed. The resulted modified T-cells may be pooled and administrated to one or several patients, being made available as an "off the shelf" therapeutic product.

The treatments are primarily to treat patients diagnosed with cancer. Cancers are preferably leukemias and lymphomas, which have liquid tumors, but may also concern solid tumors. Types of cancers to be treated with the genetically engineered T-cells of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

The treatment can take place in combination with one or more therapies selected from the group of antibodies therapy, chemotherapy, cytokines therapy, dendritic cell therapy, gene therapy, hormone therapy, laser light therapy and radiation therapy.

According to certain embodiments, T-cells of the invention can undergo robust in vivo T-cell expansion upon administration to a patient, and can persist in the body fluids for an extended amount of time, preferably for a week, more preferably for 2 weeks, even more preferably for at least one month. Although the T-cells according to the invention are expected to persist during these periods, their life span into the patient's body are intended not to exceed a year, preferably 6 months, more preferably 2 months, and even more preferably one month.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of 104-109 cells per kg body weight, preferably 105 to 106 cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In other embodiments, said effective amount of cells or composition comprising those cells are administrated parenterally. Said administration can be an intravenous administration. Said administration can be directly done by injection within a tumor.

In certain embodiments, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1 1; Henderson et al., Immun. 73:316-321, 1991; Bierer et al., Citrr. Opin. mm n. 5:763-773, 93). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded genetically engineered T-cells of the present invention. In an additional embodiment, expanded cells are administered before or following surgery.

Also encompassed within this aspect of the invention are methods for treating a patient in need thereof, comprising a) providing at least one engineered T-cell of the present invention, preferably a population of said T-cell; and b) administering said T-cell or population to said patient.

Also encompassed within this aspect of the invention are methods for preparing a medicament using at least one engineered T-cell of the present invention, and preferably a population of said T-cell. Accordingly, the present invention provides the use of at least one engineered T-cell of the present invention, and preferably a population of said T-cell, in the manufacture of a medicament. Preferably, such medicament is for use in the treatment of a cancer, such as lymphoma, or viral infection.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

by "polynucleotide successively comprising a first region of homology to sequences upstream of said double-stranded break, a sequence to be inserted in the genome of said cell and a second region of homology to sequences downstream of said double-stranded break" it is intended to mean a DNA construct or a matrix comprising a first and second portion that are homologous to regions 5' and 3' of a DNA target in situ. The DNA construct also comprises a third portion positioned between the first and second portion which comprise some homology with the corresponding DNA sequence in situ or alternatively comprise no homology with the regions 5' and 3' of the DNA target in situ. Following cleavage of the DNA target, a homologous recombination event is stimulated between the genome containing the targeted gene comprised in the locus of interest and this matrix, wherein the genomic sequence containing the DNA target is replaced by the third portion of the matrix and a variable part of the first and second portions of said matrix.

by "DNA target", "DNA target sequence", "target DNA sequence", "nucleic acid target sequence", "target sequence", or "processing site" is intended a polynucleotide sequence that can be targeted and processed by a rare-cutting endonuclease according to the present invention. These terms refer to a specific DNA location, preferably a genomic location in a cell, but also a portion of genetic material that can exist independently to the main body of genetic material such as plasmids, episomes, virus, transposons or in organelles such as mitochondria as non-limiting example. As non-limiting examples of RNA guided target sequences, are those genome sequences that can hybridize the guide RNA which directs the RNA guided endonuclease to a desired locus.

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, or penetrating peptides. In these later cases, delivery vectors are molecule carriers.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomega-lovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Uppincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as non limiting example, that are able to integrate the genome of a target cell. At the opposite by "non integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By "cell" or "cells" is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non-limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of up to one, two, three, four, five, six, seven, eight, nine, ten, eleven, twelve, thirteen, fourteen, fifteen, twenty, twenty five, thirty, forty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

As used herein, the term "locus" is the specific physical location of a DNA sequence (e.g. of a gene) on a chromosome. The term "locus" can refer to the specific physical location of a rare-cutting endonuclease target sequence on a chromosome. Such a locus can comprise a target sequence that is recognized and/or cleaved by a rare-cutting endonuclease according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria as non-limiting examples.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

By "fusion protein" is intended the result of a well-known process in the art consisting in the joining of two or more genes which originally encode for separate proteins or part of them, the translation of said "fusion gene" resulting in a single polypeptide with functional properties derived from each of the original proteins.

"identity" refers to sequence identity between two nucleic acid molecules or polypeptides. Identity can be determined by comparing a position in each sequence which may be aligned for purposes of comparison. When a position in the compared sequence is occupied by the same base or amino acid, then the molecules are identical at that position. A degree of similarity or identity between nucleic acid or amino acid sequences is a function of the number of identical or matching nucleotides or amino acids at positions shared by the nucleic acid or amino acid sequences, respectively. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

"inhibiting" or "inhibit" expression of B2M means that the expression of B2M in the cell is reduced by at least 1%, at least 5%, at least 10%, at least 20%, at least 30%, at least 40%, at least 50% at least 60%, at least 70%, at least 80%, at least 90%, at least 95%, at least 99% or 100%. More particularly, "inhibiting" or "inhibit" expression of B2M means that the amount of B2M in the cell is reduced by at least 1%, at least 5%, at least 10%, at least 20%, at least 30%, at least 40%, at least 50% at least 60%, at least 70%, at least 80%, at least 90%, at least 95%, at least 99% or 100%. The expression or amount of protein in a cell can be determined by any suitable means know in the art, such as ELISA, Immunohistochemistry, Western Blotting or Flow Cytometry using B2M specific antibodies. Such antibodies are commercially available from various sources, such from Merck Millipore, Billerica, MA, USA; or Abcam plc, Cambridge, UK.

"inhibiting" or "inhibit" expression of CIITA means that the expression of CIITA in the cell is reduced by at least 1%, at least 5%, at least 10%, at least 20%, at least 30%, at least 40%, at least 50%, at least 60%, at least 70%, at least 80%, at least 90%, at least 95%, at least 99% or 100%. More particularly, "inhibiting" or "inhibit" expression of CIITA means that the amount of CIITA in the cell is reduced by at least 1%, at least 5%, at least 10%, at least 20%, at least 30%, at least 40%, at least 50% at least 60%, at least 70%, at least 80%, at least 90%, at least 95%, at least 99% or 100%. The expression or amount of protein in a cell can be determined by any suitable means know in the art, such as ELISA, Immunohistochemistry, Western Blotting or Flow Cytometry using CIITA specific antibodies. Such antibodies are commercially available from various sources, such from Abcam plc, Cambridge, UK; or Santa Cruz Biotechnology, Inc., Santa Cruz, CA, USA.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory igand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a Tcell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/CD3 ligation, leads to T cell proliferation and/or upregulation or downregulation of key molecules.

"bispecific antibody" refers to an antibody that has binding sites for two different antigens within a single antibody molecule. It will be appreciated by those skilled in the art that other molecules in addition to the canonical antibody structure may be constructed with two binding specificities. It will further be appreciated that antigen binding by bispecific antibodies may be simultaneous or sequential. Bispecific antibodies can be produced by chemical techniques (see e.g., Kranz et al. (1981) Proc. Natl. Acad. Sci. USA 78, 5807), by "polydoma" techniques (See U.S. Pat. No. 4,474,893) or by recombinant DNA techniques, which all are known per se. As a non-limiting example, each binding domain comprises at least one variable region from an antibody heavy chain ("VH or H region"), wherein the VH region of the first binding domain specifically binds to the lymphocyte marker such as CD3, and the VH region of the second binding domain specifically binds to tumor antigen.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

Having generally described this invention, a further understanding can be obtained by reference to certain specific examples, which are provided herein for purposes of illustration only, and are not intended to be limiting unless otherwise specified.

EXAMPLES

TALE-Nucleases Cleaving Human CIITA mRNA encoding the TALE-nucleases targeting exons of the human CIITA gene were ordered from Cellectis Bioresearch (8, rue de la Croix Jarry, 75013 PARIS). Table 3 below indicates the target sequences cleaved by each of the two independent entities (called half TALE-nucleases) each containing a repeat sequence engineered to bind and cleave between target sequences consisting of two 17-bp long sequences (called half targets) separated by a 15-bp spacer. Because Exon 2 and 3 are shared by all transcript variants of CIITA, two TALEN pairs were designed for Exon 2 and 3. No obvious offsite targeting in the human genome have been predicted using TALE-Nucleases targeting these sequences.

TABLE 3

Description of the CIITA TALE-nucleases and related target sequences

| Target name | Target sequence |
|---|---|
| TALEN_1_Exon_2_CMH-II-TA | TTCCCTCCCAGGCAG CTCacagtgtgccac caTGGAGTTGGGGCC CCTA (SEQ ID NO: 55) |
| TALEN_2_Exon_2_CMH-II-TA | TGCCTCTACCACTTC TATgaccagatggac ctGGCTGGAGAAGAA GAGA (SEQ ID NO: 56) |
| TALEN_1_Exon3_CMH-II-TA | 5'TCTTCATCCAAGG GACTTttcctcccag aaccCGACACAGACA CCATCA (SEQ ID NO: 57) |
| TALEN_2_Exon3_CMH-II-TA | TGTTGTGTGACATGG AAGgtgatgaagaga ccAGGGAGGCTTATG CCAA (SEQ ID NO: 58) |

TALE-Nucleases Cleaving Human β2m mRNA encoding the TALE-nucleases targeting exons of the human β2m gene were ordered from Cellectis Bioresearch (8, rue de la Croix Jarry, 75013 PARIS). Table 4 below indicates the target sequences cleaved by each of the two independent entities (called half TALE-nucleases) each containing a repeat sequence engineered to bind and cleave between target sequences consisting of two 17-bp long sequences (called half targets) separated by a 15-bp spacer.

TABLE 4

Description of the β2m TALE-nucleases and related target sequences

| Target name | Target sequence | Half TALE-nuclease sequence |
|---|---|---|
| B2M_T03 | 5'-CCAAAGATTCAGGTTT actcacgtcatccagc (spacer)AGAGAATG GAAAGTC-3' (SEQ ID NO: 59) | Repeat B2M_T03-L (pCLS24605) SEQ ID NO: 67 B2M_T03-R (pCLS24606) SEQ ID NO: 68 |

TALE-Nucleases Cleaving Human TCR Genes (TRAC and TRBC)

The human genome contains two functional T-cell receptor beta chains (TRBC1 and TRBC2). During the development of alpha/beta T lymphocytes, one of these two constant chains is selected in each cell to be spliced to the variable region of TCR-beta and form a functional full length beta chain. Table 5 below presents a TRAC and 2 TRBC target sequences and their corresponding TALEN sequences. The 2 TRBC targets were chosen in sequences conserved between TRBC1 and TRBC2 so that the corresponding TALE-nuclease would cleave both TRBC1 and TRBC2 at the same time.

TABLE 5

Description of the TRAC and TRBC TALE-nucleases and sequences of the TALE-nucleases target sites in the human corresponding genes.

| Target | Target sequence | Half TALE-nuclease |
|---|---|---|
| TRAC_T01 | TTGTCCCACAGATATCC Agaaccctgaccctg CCGTGTACCAGCTGAGA (SEQ ID NO: 60) | TRAC_T01-L TALEN (SEQ ID NO: 69) TRAC_T01-R TALEN (SEQ ID NO: 70) |
| TRBC_T01 | TGTGTTTGAGCCATCAG aagcagagatctccc ACACCCAAAAGGCCACA (SEQ ID NO: 61) | TRBC_T01-L TALEN (SEQ ID NO: 71) TRBC_T01-R TALEN (SEQ ID NO: 72) |
| TRBC_T02 | TTCCCACCCGAGGTCGC tgtgtttgagccatca GAAGCAGAGATCTCCCA (SEQ ID NO: 62) | TRBC_T02-L TALEN (SEQ ID NO: 73) TRBC_T02-R TALEN (SEQ ID NO: 74) |

Other target sequences in TRAC and CD52 genes have been designed, which are displayed in Table 6.

TABLE 6

Additional target sequences for TRAC TALE-nucleases.

| Target | Target sequence |
|---|---|
| TRAC_T02 | TTTAGAAAGTTCCTGTG atgtcaagctggtcg AGAAAAGCTTTGAAACA (SEQ ID NO: 63) |
| TRAC_T03 | TCCAGTGACAAGTCTGT ctgcctattcaccga TTTTGATTCTCAAACAA (SEQ ID NO: 64) |

TABLE 6-continued

Additional target sequences for TRAC TALE-nucleases.

| Target | Target sequence |
|---|---|
| TRAC_T04 | TATATCACAGACAAAAC tgtgctagacatgag GTCTATGGACTTCAAGA (SEQ ID NO: 65) |
| TRAC_T05 | TGAGGTCTATGGACTTC aagagcaacagtgct GTGGCCTGGAGCAACAA (SEQ ID NO: 66) |

Electroporation of mRNA of Purified Tcells Activated Using Cytopulse Technology

After determining the best cytopulse program that allows an efficient DNA electroporation of T cells, we tested whether this method was applicable to the mRNA electroporation.

5×106 purified T cells preactivated 6 days with PHA/IL2 were resupended in cytoporation buffer T (BTX-Harvard apparatus) and electroporated in 0.4 cm cuvettes with 10 µg of mRNA encoding GFP or 20 µg of plasmids encoding GFP or pUC using the preferred cytopulse program of table 7.

TABLE 7

Cytopulse program used to electroporate purified T-cells.

| Cyto-pulse program | Group 1 | | | | Group 2 | | | | Group 3 | | | |
|---|---|---|---|---|---|---|---|---|---|---|---|---|
| | Pulse | V | duration (ms) | Interval (ms) | Pulse | V | duration (ms) | Interval (ms) | Pulse | V | duration (ms) | Interval (ms) |
| 3 | 1 | 1200 | 0.1 | 0.2 | 1 | 1200 | 0.1 | 100 | 4 | 130 | 0.2 | 2 |

48 h after transfection cells were stained with viability dye (eFluor-450) and the cellular viability and % of viable GFP+ cells was determined by flow cytometry.

The electroporation of RNA with the optimal condition determined here was not toxic and allowed transfection of more than 95% of the viable cells.

In synthesis, the whole dataset shows that T-cells can be efficiently transfected either with DNA or RNA. In particular, RNA transfection has no impact on cellular viability and allows uniform expression levels of the transfected gene of interest in the cellular population.

Efficient transfection can be achieved early after cellular activation, independently of the activation method used (PHA/IL-2 or CD3/CD28-coated-beads). The inventors have succeeded in transfecting cells from 72 h after activation with efficiencies of >95%. In addition, efficient transfection of T cells after thawing and activation can also be obtained using the same electroporation protocol.

mRNA Electroporation in Primary Human T Cells for TALE-Nuclease Functional Expression After demonstrating that mRNA electroporation allow efficient expression of GFP in primary human T cells, we tested whether this method was applicable to the expression of other proteins of interest. Transcription activator-like effector nucleases (TALE-nuclease) are site-specific nucleases generated by the fusion of a TAL DNA binding domain to a DNA cleavage domain. They are powerful genome editing tools as they induce double-strand breaks at practically any desired DNA sequence. These double-strand breaks activate Non-homologous end-joining (NHEJ), an error-prone DNA repair mechanism, potentially leading to inactivation of any desired gene of interest. Alternatively, if an adequate repair template is introduced into the cells at the same time, TALE-nuclease-induced DNA breaks can be repaired by homologous recombination, therefore offering the possibility of modifying at will the gene sequence.

We have used mRNA electroporation to express a TALE-nuclease designed to specifically cleave a sequence in the human gene coding for the alpha chain of the T cell antigen receptor (TRAC). Mutations induced in this sequence are expected to result in gene inactivation and loss of TCRαβ complex from the cell surface. TRAC TALE-nuclease RNA or non-coding RNA as control are transfected into activated primary human T lymphocytes using Cytopulse technology. The electroporation sequence consisted in 2 pulses of 1200 V followed by four pulses of 130 V as described in Table 7.

Figure 4:
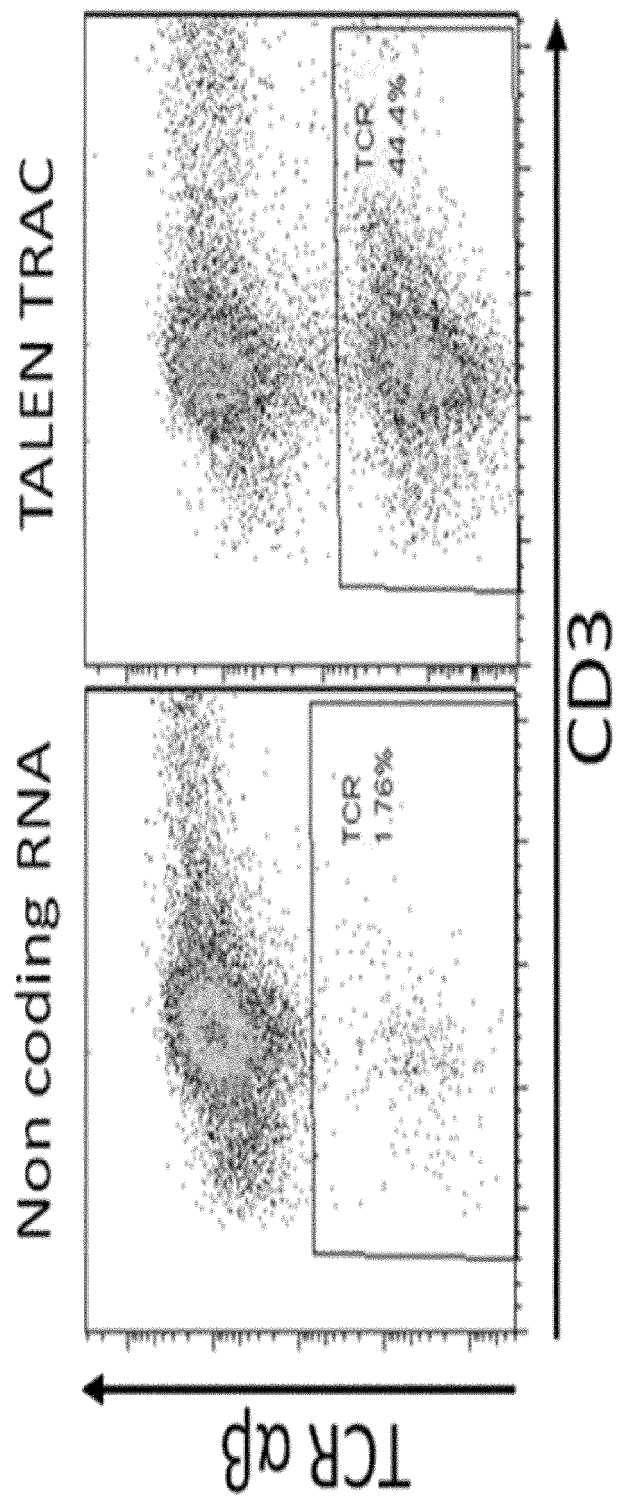
FIG. 4: Flow cytometry analysis of TCR alpha/beta and CD3 expression on human primary T cells following TRAC TALE-nuclease mRNA electroporation (top).

By flow cytometry analysis of TCR surface expression 7 days post electroporation (FIG. 4, top panel), we observed that 44% of T cells lost the expression of TCRαβ. We analyzed the genomic DNA of the transfected cells by PCR amplification of the TRAC locus followed by 454 high throughput sequencing. 33% of alleles sequenced (727 out of 2153) contained insertion or deletion at the site of TALE-nuclease cleavage.

These data indicate that electroporation of mRNA using cytopulse technology results in functional expression of TRAC TALE-nuclease.

Activity of TRAC-TALE-Nuclease and TRBC-TALE-Nuclease in HEK293 Cells

Each TALE-nuclease construct was subcloned using restriction enzyme digestion in a mammalian expression vector under the control of pEF1alpha long promoter. One million HEK293 cells were seeded one day prior to transfection. Cells were transfected with 2.5 µg of each of the two plasmids encoding the TALE-nucleases recognizing the two half targets in the genomic sequence of interest in the T-cell receptor alpha constant chain region (TRAC) or T-cell receptor beta constant chain region (TRBC) under the control of the EF1-alpha promoter or 5 µg of a control pUC vector (pCLS0003) using 25 µl of lipofectamine (Invitrogen) according to the manufacturer's instructions. The double stranded cleavage generated by TALE-nucleases in TRAC coding sequences is repaired in live cells by non homologous end joining (NHEJ), which is an error-prone mechanism. Activity of TALE-nucleases in live cells is measured by the frequency of insertions or deletions at the genomic locus targeted. 48 hours after transfection, genomic DNA was isolated from transfected cells and locus specific PCRs were performed using the following primers: for TRAC: 5'-ATCACTGGCATCTGGACTCCA-3' (SEQ ID NO: 75), for TRBC1: 5'-AGAGCCCCTACCAGAACCAGAC-3' (SEQ ID NO: 76, or for TRBC2: 5'-GGACCTAGTAACAT-AATTGTGC-3' (SEQ ID NO: 77), and the reverse primer for TRAC: 5'-CCTCATGTCTAGCACAGTTT-3'(SEQ ID NO: 78), for TRBC1 and TRBC2: 5'-ACCAGCTCAGCTC-CACGTGGT-3' (SEQ ID NO: 79). PCR products were sequenced by a 454 sequencing system (454 Life Sciences). Approximately 10,000 sequences were obtained per PCR product and then analyzed for the presence of site-specific insertion or deletion events; results are in Table 8.

TABLE 8

Percentages of indels for TALE-nuclease targeting TRAC_T01, TRBC_T01 and TRBC_T02 targets.

| Target | % Indels with TALE-nuclease transfection | % Indels with pUC control transfection |
| --- | --- | --- |
| TRAC_T01 | 41.9 | 0.3 |
| TRBC_T01 in constant chain 1 | 3.81 | 0 |
| TRBC_T01 in constant chain 2 | 2.59 | 0 |
| TRBC_T02 in constant chain 1 | 14.7 | 0 |
| TRBC_102 in constant chain 1 | 5.99 | 0 |

Activity of β2m and TRAC-TALE-Nuclease in Primary T Lymphocytes

Each TALE-nuclease construct was subcloned using restriction enzyme digestion in a mammalian expression vector under the control of the T7 promoter.

mRNA encoding TALE-nuclease cleaving β2m, TRAC and TRBC genomic sequence were synthesized from plasmid carrying the coding sequences downstream from the T7 promoter. T lymphocytes isolated from peripheral blood were activated for 5 days using anti-CD3/CD28 activator beads (Life technologies) and 5 million cells were then transfected by electroporation with 10 μg of each of 2 mRNAs encoding both half TALE-nuclease (or non coding RNA as controls) using a CytoLVT-P instrument. As a consequence of the insertions and deletions induced by NHEJ, the coding sequence for β2m and/or TRAC will be out of frame in a fraction of the cells resulting in non-functional genes. 5 days after electroporation, cells were labeled with fluorochrome-conjugated anti-β2m or anti-TCR antibody by flow cytometry for the presence of β2m or TCR at their cell surface. Since all T lymphocytes expanded from peripheral blood normally express β2m and TCR, the proportion of β2m-negative or TCR-negative cells is a direct measure of TALE-nuclease activity.

Functional Analysis of T Cells with Targeted TRAC Gene

Figure 3:
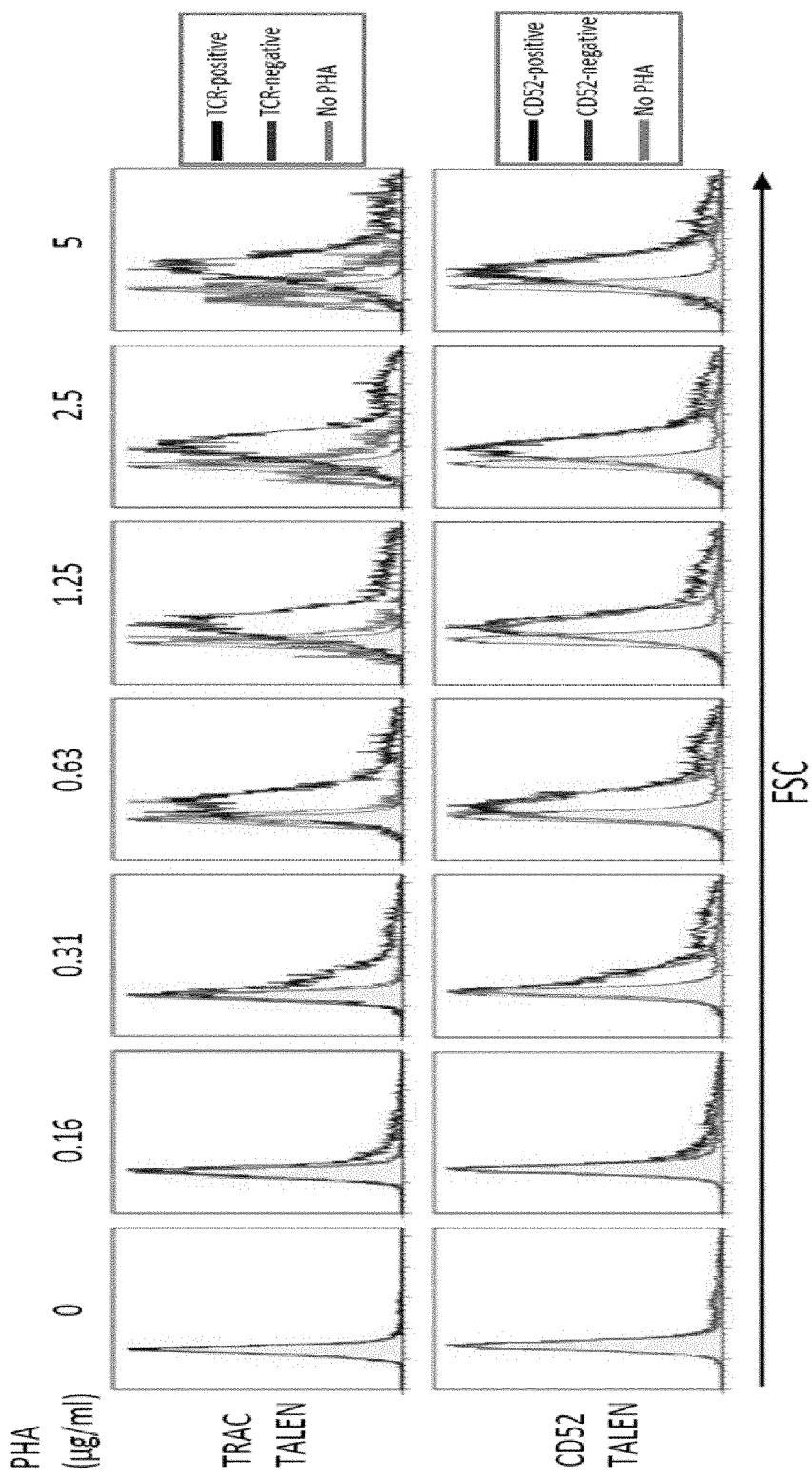
FIG. 3: Comparison of the forward side scatter (FSC) distribution, an indicator of cell size, between TCR-positive and TCR-negative cells.

The goal of TRAC gene inactivation is to render T lymphocytes unresponsive to T-cell receptor stimulation. As described in the previous paragraph, T lymphocytes were transfected with mRNA encoding TALE-nuclease cleaving TRAC. 16 days after transfection, cells were treated with up to 5 μg/ml of phytohemagglutinin (PHA, Sigma-Aldrich), a T-cell mitogen acting through the T cell receptor. Cells with a functional T-cell receptor should increase in size following PHA treatment. After three days of incubation, cells were labeled with a fluorochrome-conjugated anti-TCR antibody and analyzed by flow cytometry to compare the cell size distribution between TCR-positive and TCR-negative cells. FIG. 3 shows that TCR-positive cells significantly increase in size after PHA treatment whereas TCR-negative cells have the same size as untreated cells indicating that TRAC inactivation rendered them unresponsive to TCR-signaling.

Functional Analysis of T Cells with Targeted β2m Gene

Figure 5:
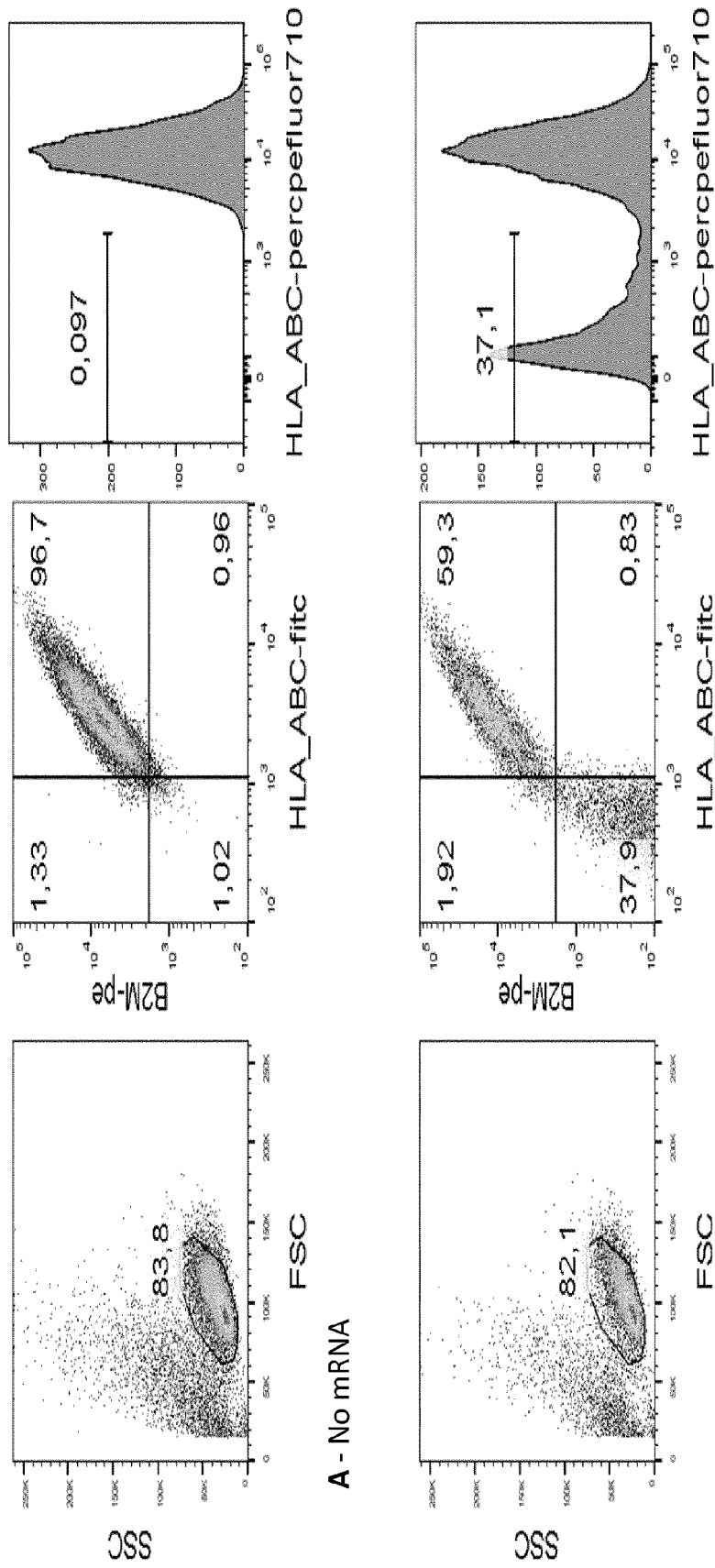
FIG. 5: Flow cytometry analysis of HLA_ABC expression on the surface of human primary T cells in: A. Control T-cells. B. following β2m TALE-nuclease mRNA electroporation.

Similarly to the above, the TALEN-transfected cells and control cells (transfected without RNA) were stained with fluorochrome labeled antibody against B2M protein as well as an antibody recognizing all three classes MHC-I molecules (HLA-A, -B or -C). TALEN transfection induced loss of surface expression of B2M and MHC-I molecules in more than 37% of T cells. See FIG. 5

Genomic Safety of β2m-TALE-Nuclease and TRAC-TALE-Nuclease in Primary T Lymphocytes As our constructs include nuclease subunits, an important question is whether multiple TALE-nuclease transfection can lead to genotoxicity and off-target cleavage at 'close match' target sequences or by mispairing of half-TALE-nucleases. To estimate the impact of TRAC-TALE-nuclease and β2m-TALE-nuclease on the integrity of the cellular genomes, we listed sequences in the human genome that presented the potential for off-site cleavage. To generate this list, we identified all the sequences in the genome with up to 4 substitutions compared to the original half targets and then identified the pairs of potential half targets in a head to head orientation with a spacer of 9 to 30 bp from each other. This analysis included sites potentially targeted by homodimers of one half-TALE-nuclease molecule or heterodimers formed by one β2m half TALE-nuclease and one TRAC half-TALE-nuclease. We scored the potential off-site targets based on the specificity data taking into account the cost of individual substitutions and the position of the substitutions (where mismatches are better tolerated for bases at the 3' end of the half target). We obtained 173 unique sequences with a score reflecting an estimation of the likelihood of cleavage. We selected the 15 top scores and analyzed by deep sequencing the frequency of mutations found at these loci in T cells simultaneously transfected with β2m and TRAC TALE-nuclease and purified by magnetic separation as β2m-negative, TCRαβ-negative. Results showed that the highest frequency of insertion/deletion is $7 \times 10^{-4}$. These results make the putative offsite target at least 600 times less likely to be mutated than the intended targets. The TALE-nuclease reagents used in this study therefore appear extremely specific.

Electroporation of T Cells with a Monocistronic mRNA encodinR for an Anti-CD19 Single Chain Chimeric antiRen Receptor (CAR):

5×106 T cells preactivated several days (3-5) with anti-CD3/CD28 coated beads and IL2 were resuspended in cytoporation buffer T, and electroporated in 0.4 cm cuvettes without mRNA or with 10 g of mRNA encoding a single chain CAR (SEQ ID NO: 6) using the program described in Table 7.

24 hours post electroporation, cells were stained with a fixable viability dye eFluor-780 and a PE-conjugated goat anti mouse IgG F(ab')2 fragment specific to assess the cell surface expression of the CAR on the live cells. The data is shown in the FIG. 6. A indicates that the vast majority of the live T cells electroporated with the monocitronic mRNA described previously express the CAR at their surface. 24 hours post electroporation, T cells were cocultured with Daudi (CD19+) cells for 6 hours and analyzed by flow cytometry to detect the expression of the degranulation marker CD107a at their surface (Betts, Brenchley et al. 2003).

Figure 6:
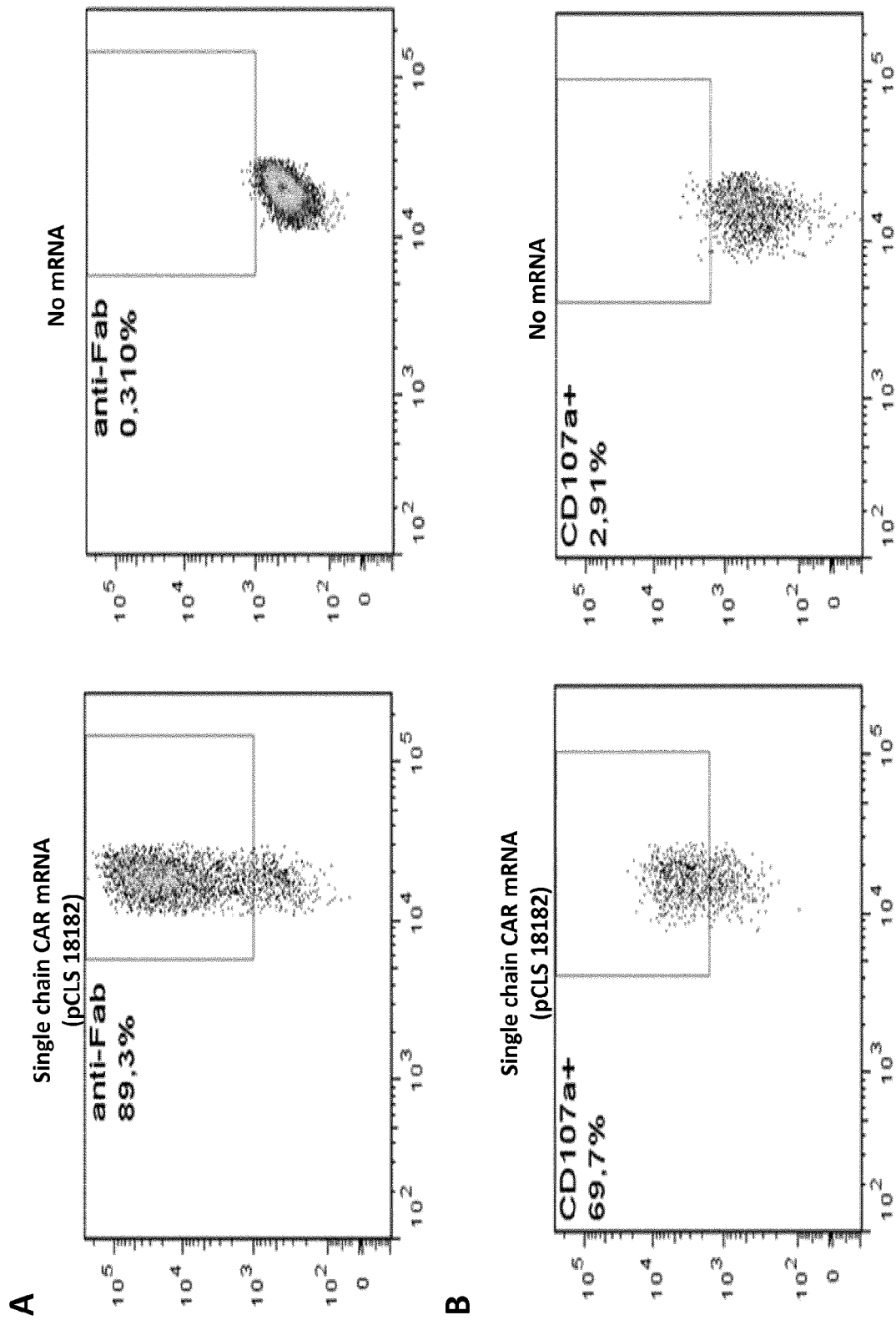
FIG. 6: A. Flow cytometry analysis of CAR expression (anti F(ab')2) after electroporation of T cells with or without mRNA encoding a single chain CAR. B. Flow cytometry analysis of CD107a expression (marker of degranulation) on electroporated T cells cocultured with daudi cells.

The data shown in FIG. 6 indicates that the majority of the cells electroporated with the monocistronic mRNA described previously degranulate in the presence of target cells expressing CD19. These results clearly demonstrate that the CAR expressed at the surface of electroporated T cells is active.

In the following examples, to prolong their survival and enhance their therapeutic activity, the inventors describe a method to prevent NK-cell mediated rejection of therapeutic allogeneic T cells by engineering the allogenic T cells through the inactivation of the B2M gene using specific TALEN, combined to either: i) the expression of a chimeric single chain molecule composed of UL18 and 132M B2M-UL18) or ii) the secretion of NKG2D ligands. The particularity resides in applying to primary T cells a mechanism occuring normally in tumor cells or virally infected cells. Thus, the mechanism of action is potentially different: in tumor cells, shedding NKG2D ligands leads to their decreased presence at the surface whereas in engineered cells, secreted the NKG2D ligand(s) would serve as a decoy for several other NKG2D ligands potentially still present at the T cell surface.

Efficient B2M Gene Knock Out Using Specific B2M TALEN.

Specific TALEN targeting a sequence (T01, SEQ ID No 81) within the first coding exon of the B2M gene (GenBank accession number NC_000015) has been produced (left DNA binding domain RVDs: NN-NN-HD-HD-NG-NG-NI-NN-HD-NG-NN-NG-NN-HD-NG-NG with SEQ ID NO: 82, and right DNA binding domain RVDs: NI-NN-HD-HD-NG-HD-HD-NI-NN-NN-HD-HD-NI-NN-NI-NG with SEQ ID NO: 83). The Table 9 below reports sequences for T01 targeting sequence, as well as for 2 additional targets T02 and T03 and their corresponding left and right TALE sequences.

TABLE 9

Description of additional β2m TALE-nucleases sequences

| Target name | SEQ ID NO: | Half TALE-nuclease sequence |
|---|---|---|
| T01 Beta2M target | 80 | TCTCGCTCCGTGGCCTTAGCTGTGCTCGCGCTACTCTCTCTTTCTGGCCTGGAGGCTA |
| T01 TALEN Beta2M LEFT | 81 | ATGGGCGATCCTAAAAAGAAACGTAAGGTCATCGATTACCCATACGATGTTCCAGATTACGCTATCGATA<br>TCGCCGATCTACGCACGCTCGGCTACAGCCAGCAGCAACAGGAGAAGATCAAACCGAAGGTTCGTTCGA<br>CAGTGGCGCAGCACCACGAGGCACTGGTCGGCCACGGGTTTACACACGCGCACATCGTTGCGTTAAGCC<br>AACACCCGGCAGCGTTAGGGACCGTCGCTGTCAAGTATCAGGACATGATCGCAGCGTTGCCAGAGGCGA<br>CACACGAAGCGATCGTTGGCGTCGGCAAACAGTGGTCCGGCGCACGCGCTCTGGAGGCCTTGCTCACGG<br>TGGCGGGAGAGTTGAGAGGTCCACCGTTACAGTTGGACACAGGCCAACTTCTCAAGATTGCAAAACGTG<br>GCGGCGTGACCGCAGTGGAGGCAGTGCATGCATGGCGCAATGCACTGACGGGTGCCCCGCTCAACTTGA<br>CCCCCCAGCAGGTGGTGGCCATCGCCAGCAATAATGGTGGCAAGCAGGCGCTGGAGACGGTCCAGCGG<br>CTGTTGCCGGTGCTGTGCCAGGCCCACGGCTTGACCCCCCAGCAGGTGGTGGCCATCGCCAGCAATAATG<br>GTGGCAAGCAGGCGCTGGAGACGGTCCAGCGGCTGTTGCCGGTGCTGTGCCAGGCCCACGGCTTGACCC<br>CGGAGCAGGTGGTGGCCATCGCCAGCCACGATGGCGGCAAGCAGGCGCTGGAGACGGTCCAGCGGCTG<br>TTGCCGGTGCTGTGCCAGGCCCACGGCTTGACCCCGGAGCAGGTGGTGGCCATCGCCAGCCACGATGGC<br>GGCAAGCAGGCGCTGGAGACGGTCCAGCGGCTGTTGCCGGTGCTGTGCCAGGCCCACGGCTTGACCCCC<br>CAGCAGGTGGTGGCCATCGCCAGCAATGGCGGTGGCAAGCAGGCGCTGGAGACGGTCCAGCGGCTGTT<br>GCCGGTGCTGTGCCAGGCCCACGGCTTGACCCCCCAGCAGGTGGTGGCCATCGCCAGCAATGGCGGTGG<br>CAAGCAGGCGCTGGAGACGGTCCAGCGGCTGTTGCCGGTGCTGTGCCAGGCCCACGGCTTGACCCCGGA<br>GCAGGTGGTGGCCATCGCCAGCAATATTGGTGGCAAGCAGGCGCTGGAGACGGTGCAGGCGCTGTTGC<br>CGGTGCTGTGCCAGGCCCACGGCTTGACCCCCCAGCAGGTGGTGGCCATCGCCAGCAATAATGGTGGCA<br>AGCAGGCGCTGGAGACGGTCCAGCGGCTGTTGCCGGTGCTGTGCCAGGCCCACGGCTTGACCCCGGAGC<br>AGGTGGTGGCCATCGCCAGCCACGATGGCGGCAAGCAGGCGCTGGAGACGGTCCAGCGGCTGTTGCCG<br>GTGCTGTGCCAGGCCCACGGCTTGACCCCCCAGCAGGTGGTGGCCATCGCCAGCAATGGCGGTGGCAAG<br>CAGGCGCTGGAGACGGTCCAGCGGCTGTTGCCGGTGCTGTGCCAGGCCCACGGCTTGACCCCCAGCAG<br>GTGGTGGCCATCGCCAGCAATAATGGTGGCAAGCAGGCGCTGGAGACGGTCCAGCGGCTGTTGCCGGT<br>GCTGTGCCAGGCCCACGGCTTGACCCCCAGCAGGTGGTGGCCATCGCCAGCAATGGCGGTGGCAAGCA<br>GGCGCTGGAGACGGTCCAGCGGCTGTTGCCGGTGCTGTGCCAGGCCCACGGCTTGACCCCCCAGCAGGT<br>GGTGGCCATCGCCAGCAATAATGGTGGCAAGCAGGCGCTGGAGACGGTCCAGCGGCTGTTGCCGGTGCT<br>GTGCCAGGCCCACGGCTTGACCCCGGACAGGTGGTGGCCATCGCCAGCCACGATGGCGGCAAGCAGG<br>CGCTGGAGACGGTCCAGCGGCTGTTGCCGGTGCTGTGCCAGGCCCACGGCTTGACCCCCCAGCAGGTGG<br>TGGCCATCGCCAGCAATGGCGGTGGCAAGCAGGCGCTGGAGACGGTCCAGCGGCTGTTGCCGGTGCTGT<br>GCCAGGCCCACGGCTTGACCCCTCAGCAGGTGGTGGCCATCGCCAGCAATGGCGGCGGCAGGCCGGCGC<br>TGGAGAGCATTGTTGCCCAGTTATCTCGCCCTGATCCGGCGTTGGCCGCGTTGACCAACGACCACCTCGTC<br>GCCTTGGCCTGCCTCGGCGGGCGTCCTGCGCTGGATGCAGTGAAAAAGGGATTGGGGGATCCTATCAGC<br>CGTTCCCAGCTGGTGAAGTCCGAGCTGGAGGAGAAGAAATCCGAGTTGAGGCACAAGCTGAAGTACGTG<br>CCCCACGAGTACATCGAGCTGATCGAGATCGCCCGGAACAGCACCCAGGACCGTATCCTGGAGATGAAG<br>GTGATGGAGTTCTTCATGAAGGTGTACGGCTACAGGGGCAAGCACCTGGGCGGCTCCAGGAAGCCCGAC<br>GGCGCCATCTACACCGTGGGCTCCCCCATCGACTACGGCGTGATCGTGGACACCAAGGCCTACTCCGGCG<br>GCTACAACCTGCCCATCGGCCAGGCCGACGAAATGCAGAGGTACGTGGAGGAGAACCAGACCAGGAAC<br>AAGCACATCAACCCCAACGAGTGGTGGAAGGTGTACCCCTCCAGCGTGACCGAGTTCAAGTTCCTGTTCG<br>TGTCCGGCCACTTCAAGGGCAACTACAAGGCCCAGCTGACCAGGCTGAACCACATCACCAACTGCAACGG<br>CGCCGTGCTGTCCGTGGAGGAGCTCCTGATCGGCGGCGAGATGATCAAGGCCGGCACCCTGACCCTGGA<br>GGAGGTGAGGAGGAAGTTCAACAACGGCGAGATCAACTTCGCGGCCGACTGATAA |
| T01 TALEN Beta2M RIGHT | 82 | ATGGGCGATCCTAAAAAGAAACGTAAGGTCATCGATAAGGAGACCGCCGCTGCCAAGTTCGAGAGACAG<br>CACATGGACAGCATCGATATCGCCGATCTACGCACGCTCGGCTACAGCCAGCAGCAACAGGAGAAGATC<br>AAACCGAAGGTTCGTTCGACAGTGGCGCAGCACCACGAGGCACTGGTCGGCCACGGGTTTACACACGCG<br>CACATCGTTGCGTTAAGCCAACACCCGGCAGCGTTAGGGACCGTCGCTGTCAAGTATCAGGACATGATCG<br>CAGCGTTGCCAGAGGCGACACACGAAGCGATCGTTGGCGTCGGCAAACAGTGGTCCGGCGCACGCGCTC<br>TGGAGGCCTTGCTCACGGTGGCGGGAGAGTTGAGAGGTCCACCGTTACAGTTGGACACAGGCCAACTTC<br>TCAAGATTGCAAAACGTGGCGGCGTGACCGCAGTGGAGGCAGTGCATGCATGGCGCAATGCACTGACG<br>GGTGCCCCGCTCAACTTGACCCCGGAGCAGGTGGTGGCCATCGCCAGCAATATTGGTGGCAAGCAGGCG<br>CTGGAGACGGTGCAGGCGCTGTTGCCGGTGCTGTGCCAGGCCCACGGCTTGACCCCCCAGCAGGTGGTG<br>GCCATCGCCAGCAATAATGGTGGCAAGCAGGCGCTGGAGACGGTCCAGCGGCTGTTGCCGGTGCTGTGC<br>CAGGCCCACGGCTTGACCCCGGAGCAGGTGGTGGCCATCGCCAGCCACGATGGCGGCAAGCAGGCGCT |

TABLE 9-continued

Description of additional β2m TALE-nucleases sequences

| Target name | SEQ ID NO: | Half TALE-nuclease sequence |
|---|---|---|
| | | GGAGACGGTCCAGCGGCTGTTGCCGGTGCTGTGCCAGGCCCACGGCTTGACCCCGGAGCAGGTGGTGG<br>CCATCGCCAGCCACGATGGCGGCAAGCAGGCGCTGGAGACGGTCCAGCGGCTGTTGCCGGTGCTGTGCC<br>AGGCCCACGGCTTGACCCCCAGCAGGTGGTGGCCATCGCCAGCAATGGCGGTGGCAAGCAGGCGCTG<br>GAGACGGTCCAGCGGCTGTTGCCGGTGCTGTGCCAGGCCCACGGCTTGACCCCGGAGCAGGTGGTGGCC<br>ATCGCCAGCCACGATGGCGGCAAGCAGGCGCTGGAGACGGTCCAGCGGCTGTTGCCGGTGCTGTGCCAG<br>GCCCACGGCTTGACCCCGGAGCAGGTGGTGGCCATCGCCAGCCACGATGGCGGCAAGCAGGCGCTGGA<br>GACGGTCCAGCGGCTGTTGCCGGTGCTGTGCCAGGCCCACGGCTTGACCCCGGAGCAGGTGGTGGCCAT<br>CGCCAGCAATATTGGTGGCAAGCAGGCGCTGGAGACGGTCAGGCGCTGTTGCCGGTGCTGTGCCAGG<br>CCCACGGCTTGACCCCCAGCAGGTGGTGGCCATCGCCAGCAATAATGGTGGCAAGCAGGCGCTGGAGA<br>CGGTCCAGCGGCTGTTGCCGGTGCTGTGCCAGGCCCACGGCTTGACCCCCAGCAGGTGGTGGCCATCG<br>CCAGCAATAATGGTGGCAAGCAGGCGCTGGAGACGGTCCAGCGGCTGTTGCCGGTGCTGTGCCAGGCCC<br>ACGGCTTGACCCCGGAGCAGGTGGTGGCCATCGCCAGCCACGATGGCGGCAAGCAGGCGCTGGAGACG<br>GTCCAGCGGCTGTTGCCGGTGCTGTGCCAGGCCCACGGCTTGACCCCGGAGCAGGTGGTGGCCATCGCC<br>AGCCACGATGGCGGCAAGCAGGCGCTGGAGACGGTCCAGCGGCTGTTGCCGGTGCTGTGCCAGGCCCA<br>CGGCTTGACCCCGGAGCAGGTGGTGGCCATCGCCAGCAATATTGGTGGCAAGCAGGCGCTGGAGACGG<br>TGCAGGCGCTGTTGCCGGTGCTGTGCCAGGCCCACGGCTTGACCCCCAGCAGGTGGTGGCCATCGCCA<br>GCAATAATGGTGGCAAGCAGGCGCTGGAGACGGTCCAGCGGCTGTTGCCGGTGCTGTGCCAGGCCCACG<br>GCTTGACCCCGGAGCAGGTGGTGGCCATCGCCAGCAATATTGGTGGCAAGCAGGCGCTGGAGACGGTG<br>CAGGCGCTGTTGCCGGTGCTGTGCCAGGCCCACGGCTTGACCCCTCAGCAGGTGGTGGCCATCGCCAGC<br>AATGGCGGCGGCAGGCCGGCGCTGGAGAGCATTGTTGCCCAGTTATCTCGCCCTGATCCGGCGTTGGCC<br>GCGTTGACCAACGACCACCTCGTCGCCTTGGCCTGCCTCGGCGGGCGTCCTGCGCTGGATGCAGTGAAAA<br>AGGGATTGGGGGATCCTATCAGCCGTTCCCAGCTGGTGAAGTCCGAGCTGGAGGAGAAGAAATCCGAGT<br>TGAGGCACAAGCTGAAGTACGTGCCCCACGAGTACATCGAGCTGATCGAGATCGCCGGAACAGCACCC<br>AGGACCGTATCCTGGAGATGAAGGTGATGGAGTTCTTCATGAAGGTGTACGGCTACAGGGGCAAGCACC<br>TGGGCGGCTCCAGGAAGCCCGACGGCGCCATCTACACCGTGGGCTCCCCCATCGACTACGGCGTGATCGT<br>GGACACCAAGGCCTACTCCGGCGGCTACAACCTGCCCATCGGCCAGGCCGACGAAATGCAGAGGTACGT<br>GGAGGAGAACCAGACCAGGAACAAGCACATCAACCCCAACGAGTGGTGGAAGGTGTACCCCTCCAGCGT<br>GACCGAGTTCAAGTTCCTGTTCGTGTCCGGCCACTTCAAGGGCAACTACAAGGCCCAGCTGACCAGGCTG<br>AACCACATCACCAACTGCAACGGCGCCGTGCTGTCCGTGGAGGAGCTCCTGATCGGCGGCGAGATGATC<br>AAGGCCGGCACCCTGACCCTGGAGGAGGTGAGGAGGAAGTTCAACAACGGCGAGATCAACTTCGCGGC<br>CGACTGATAA |
| T02 Beta2M target | 83 | TCCAAAGATTCAGGTTTACTCACGTCATCCAGCAGAGAATGGAAAGTCAA |
| T02 TALEN Beta2M LEFT | 84 | ATGGGCGATCCTAAAAAGAAACGTAAGGTCATCGATTACCCATACGATGTTCCAGATTACGCTATCGATA<br>TCGCCGATCTACGCACGCTCGGCTACAGCCAGCAGCAACAGGAGAAGATCAAACCGAAGGTTCGTTCGA<br>CAGTGGCGCAGCACCACGAGGCACTGGTCGGCCACGGGTTTACACACGCGCACATCGTTGCGTTAAGCC<br>AACACCCGGCAGCGTTAGGGACCGTCGCTGTCAAGTATCAGGACATGATCGCAGCGTTGCCAGAGGCGA<br>CACACGAAGCGATCGTTGGCGTCGGCAAACAGTGGTCCGGCGACGCGCTCTGGAGGCCTTGCTCACGG<br>TGGCGGGAGAGTTGAGAGGTCCACCGTTACAGTTGGACACAGGCCAACTTCTCAAGATTGCAAAACGTG<br>GCGGCGTGACCGCAGTGGAGGCAGTGCATGCATGGCGCAATGCACTGACGGGTGCCCCGCTCAACTTGA<br>CCCCGGAGCAGGTGGTGGCCATCGCCAGCCACGATGGCGGCAAGCAGGCGCTGGAGACGGTCCAGCGG<br>CTGTTGCCGGTGCTGTGCCAGGCCCACGGCTTGACCCCGGAGCAGGTGGTGGCCATCGCCAGCCACGAT<br>GGCGGCAAGCAGGCGCTGGAGACGGTCCAGCGGCTGTTGCCGGTGCTGTGCCAGGCCCACGGCTTGAC<br>CCCGGAGCAGGTGGTGGCCATCGCCAGCAATATTGGTGGCAAGCAGGCGCTGGAGACGGTGCAGGCGC<br>TGTTGCCGGTGCTGTGCCAGGCCCACGGCTTGACCCCGGAGCAGGTGGTGGCCATCGCCAGCAATATTG<br>GTGGCAAGCAGGCGCTGGAGACGGTCAGGCGCTGTTGCCGGTGCTGTGCCAGGCCCACGGCTTGACCC<br>CGGAGCAGGTGGTGGCCATCGCCAGCAATATTGGTGGCAAGCAGGCGCTGGAGACGGTCAGGCGCTG<br>TTGCCGGTGCTGTGCCAGGCCCACGGCTTGACCCCCAGCAGGTGGTGGCCATCGCCAGCAATAATGGT<br>GGCAAGCAGGCGCTGGAGACGGTCCAGCGGCTGTTGCCGGTGCTGTGCCAGGCCCACGGCTTGACCCCG<br>GAGCAGGTGGTGGCCATCGCCAGCAATATTGGTGGCAAGCAGGCGCTGGAGACGGTCCAGCGGCTGTT<br>GCCGGTGCTGTGCCAGGCCCACGGCTTGACCCCCAGCAGGTGGTGGCCATCGCCAGCAATGGCGGTGG<br>CAAGCAGGCGCTGGAGACGGTCCAGCGGCTGTTGCCGGTGCTGTGCCAGGCCCACGGCTTGACCCCCCA<br>GCAGGTGGTGGCCATCGCCAGCAATGGCGGTGGCAAGCAGGCGCTGGAGACGGTCCAGCGGCTGTTGC<br>CGGTGCTGTGCCAGGCCCACGGCTTGACCCCGGAGCAGGTGGTGGCCATCGCCAGCCACGATGGCGGCA<br>AGCAGGCGCTGGAGACGGTCCAGCGGCTGTTGCCGGTGCTGTGCCAGGCCCACGGCTTGACCCCGGAGC<br>AGGTGGTGGCCATCGCCAGCAATATTGGTGGCAAGCAGGCGCTGGAGACGGTCCAGCGGCTGTTGCCG<br>GTGCTGTGCCAGGCCCACGGCTTGACCCCCAGCAGGTGGTGGCCATCGCCAGCAATAATGGTGGCAAG<br>CAGGCGCTGGAGACGGTCCAGCGGCTGTTGCCGGTGCTGTGCCAGGCCCACGGCTTGACCCCCCAGCAG<br>GTGGTGGCCATCGCCAGCAATAATGGTGGCAAGCAGGCGCTGGAGACGGTCCAGCGGCTGTTGCCGGT<br>GCTGTGCCAGGCCCACGGCTTGACCCCCAGCAGGTGGTGGCCATCGCCAGCAATGGCGGTGGCAAGCA<br>GGCGCTGGAGACGGTCCAGCGGCTGTTGCCGGTGCTGTGCCAGGCCCACGGCTTGACCCCCCAGCAGGT<br>GGTGGCCATCGCCAGCAATGGCGGTGGCAAGCAGGCGCTGGAGACGGTCCAGCGGCTGTTGCCGGTGC<br>TGTGCCAGGCCCACGGCTTGACCCCTCAGCAGGTGGTGGCCATCGCCAGCGGCGGCAGGCCGG<br>CGCTGGAGAGCATTGTTGCCCAGTTATCTCGCCCTGATCCGGCGTTGGCCGCGTTGACCAACGACCACCT<br>CGTCGCCTTGGCCTGCCTCGGCGGGCGTCCTGCGCTGGATGCAGTGAAAAAGGGATTGGGGGATCCTAT<br>CAGCCGTTCCCAGCTGGTGAAGTCCGAGCTGGAGGAGAAGAAATCCGAGTTGAGGCACAAGCTGAAGTA<br>CGTGCCCCACGAGTACATCGAGCTGATCGAGATCGCCGGAACAGCACCCAGGACCGTATCCTGGAGAT<br>GAAGGTGATGGAGTTCTTCATGAAGGTGTACGGCTACAGGGGCAAGCACCTGGGCGGCTCCAGGAAGC<br>CCGACGGCGCCATCTACACCGTGGGCTCCCCCATCGACTACGGCGTGATCGTGGACACCAAGGCCTACTC<br>CGGCGGCTACAACCTGCCCATCGGCCAGGCCGACGAAATGCAGAGGTACGTGGAGGAGAACCAGACCA<br>GGAACAAGCACATCAACCCCAACGAGTGGTGGAAGGTGTACCCCTCCAGCGTGACCGAGTTCAAGTTCCT<br>GTTCGTGTCCGGCCACTTCAAGGGCAACTACAAGGCCCAGCTGACCAGGCTGAACCACATCACCAACTGC |

TABLE 9-continued

Description of additional β2m TALE-nucleases sequences

| Target name | SEQ ID NO: | Half TALE-nuclease sequence |
|---|---|---|
| | | AACGGCGCCGTGCTGTCCGTGGAGGAGCTCCTGATCGGCGGCGAGATGATCAAGGCCGGCACCCTGACC<br>CTGGAGGAGGTGAGGAGGAAGTTCAACAACGGCGAGATCAACTTCGCGGCCGACTGATAA |
| T02 TALEN Beta2M RIGHT | 85 | ATGGGCGATCCTAAAAAGAAACGTAAGGTCATCGATAAGGAGACCGCCGCTGCCAAGTTCGAGAGACAG<br>CACATGGACAGCATCGATATCGCCGATCTACGCACGCTCGGCTACAGCCAGCAGCAACAGGAGAAGATC<br>AAACCGAAGGTTCGTTCGACAGTGGCGCAGCACCACGAGGCACTGGTCGGCCACGGGTTTACACACGCG<br>CACATCGTTGCGTTAAGCCAACACCCGGCAGCGTTAGGGACCGTCGCTGTCAAGTATCAGGACATGATCG<br>CAGCGTTGCCAGAGGCGACACACGAAGCGATCGTTGGCGTCGGCAAACAGTGGTCCGGCGCACGCGCTC<br>TGGAGGCCTTGCTCACGGTGGCGGGAGAGTTGAGAGGTCCACCGTTACAGTTGGACACAGGCCAACTTC<br>TCAAGATTGCAAAACGTGGCGGCGTGACCGCAGTGGAGGCAGTGCATGCATGGCGCAATGCACTGACG<br>GGTGCCCCGCTCAACTTGACCCCCCAGCAGGTGGTGGCCATCGCCAGCAATAATGGTGGCAAGCAGGCG<br>CTGGAGACGGTCCAGCGGCTGTTGCCGGTGCTGTGCCAGGCCCACGGCTTGACCCCGGAGCAGGTGGTG<br>GCCATCGCCAGCAATATTGGTGGCAAGCAGGCGCTGGAGACGGTGCAGGCGCTGTTGCCGGTGCTGTGC<br>CAGGCCCACGGCTTGACCCCGGAGCAGGTGGTGGCCATCGCCAGCCACGATGGCGGCAAGCAGGCGCT<br>GGAGACGGTCCAGCGGCTGTTGCCGGTGCTGTGCCAGGCCCACGGCTTGACCCCCAGCAGGTGGTGGC<br>CATCGCCAGCAATGGCGGTGGCAAGCAGGCGCTGGAGACGGTCCAGCGGCTGTTGCCGGTGCTGTGCCA<br>GGCCCACGGCTTGACCCCCAGCAGGTGGTGGCCATCGCCAGCAATGGCGGTGGCAAGCAGGCGCTGG<br>AGACGGTCCAGCGGCTGTTGCCGGTGCTGTGCCAGGCCCACGCTTGACCCCCAGCAGGTGGTGGCCA<br>TCGCCAGCAATGGCGGTGGCAAGCAGGCGCTGGAGACGGTCCAGCGGCTGTTGCCGGTGCTGTGCCAG<br>GCCCACGGCTTGACCCCGGAGCAGGTGGTGGCCATCGCCAGCCACGATGGCGGCAAGCAGGCGCTGGA<br>GACGGTCCAGCGGCTGTTGCCGGTGCTGTGCCAGGCCCACGGCTTGACCCCGGAGCAGGTGGTGGCCAT<br>CGCCAGCCACGATGGCGGCAAGCAGGCGCTGGAGACGGTCCAGCGGCTGTTGCCGGTGCTGTGCCAGG<br>CCCACGGCTTGACCCCGGAGCAGGTGGTGGCCATCGCCAGCAATATTGGTGGCAAGCAGGCGCTGGAGA<br>CGGTGCAGGCGCTGTTGCCGGTGCTGTGCCAGGCCCACGGCTTGACCCCCAGCAGGTGGTGGCCATCG<br>CCAGCAATGGCGGTGGCAAGCAGGCGCTGGAGACGGTCCAGCGGCTGTTGCCGGTGCTGTGCCAGGCC<br>CACGGCTTGACCCCCAGCAGGTGGTGGCCATCGCCAGCAATGGCGGTGGCAAGCAGGCGCTGGAGAC<br>GGTCCAGCGGCTGTTGCCGGTGCTGTGCCAGGCCCACGGCTTGACCCCGGAGCAGGTGGTGGCCATCGC<br>CAGCCACGATGGCGGCAAGCAGGCGCTGGAGACGGTGCAGGCGCTGTTGCCGGTGCTGTGCCAGGCCC<br>ACGGCTTGACCCCCAGCAGGTGGTGGCCATCGCCAGCAATGGCGGTGGCAAGCAGGCGCTGGAGACG<br>GTCCAGCGGCTGTTGCCGGTGCTGTGCCAGGCCCACGGCTTGACCCCGGAGCAGGTGGTGGCCATCGCC<br>AGCCACGATGGCGGCAAGCAGGCGCTGGAGACGGTCCAGCGGCTGTTGCCGGTGCTGTGCCAGGCCCA<br>CGGCTTGACCCCCAGCAGGTGGTGGCCATCGCCAGCAATGGCGGTGGCAAGCAGGCGCTGGAGACG<br>TCCAGCGGCTGTTGCCGGTGCTGTGCCAGGCCCACGGCTTGACCCCTCAGCAGGTGGTGGCCATCGCCAG<br>CAATGGCGGCGGCAGGCCGGCGCTGGAGAGCATTGTTGCCCAGTTATCTCGCCCTGATCCGGCGTTGGC<br>CGCGTTGACCAACGACCACCTCGTCGCCTTGGCCTGCCTCGGCGGGCGTCCTGCGCTGGATGCAGTGAAA<br>AAGGGATTGGGGGATCCTATCAGCCGTTCCCAGCTGGTGAAGTCCGAGCTGGAGGAGAAGAAATCCGA<br>GTTGAGGCACAAGCTGAAGTACGTGCCCCACGAGTACATCGAGCTGATCGAGATCGCCCGGAACAGCAC<br>CCAGGACCGTATCCTGGAGATGAAGGTGATGGAGTTCTTCATGAAGGTGTACGGCTACAGGGGCAAGCA<br>CCTGGGCGGCTCCAGGAAGCCCGACGGCGCCATCTACACCGTGGGCTCCCCCATCGACTACGGCGTGATC<br>GTGGACACCAAGGCCTACTCCGGCGGCTACAACCTGCCCATCGGCCAGGCCGACGAAATGCAGAGGTAC<br>GTGGAGGAAACCAGACCAGGAACAAGCACATCAACCCCAACGAGTGGTGGAAGGTGTACCCCTCCAGC<br>GTGACCGAGTTCAAGTTCCTGTTCGTGTCCGGCCACTTCAAGGGCAACTACAAGGCCCAGCTGACCAGGC<br>TGAACCACATCACCAACTGCAACGGCGCCGTGCTGTCCGTGGAGGAGCTCCTGATCGGCGGCGAGATGA<br>TCAAGGCCGGCACCCTGACCCTGGAGGAGGTGAGGAGGAAGTTCAACAACGGCGAGATCAACTTCGCG<br>GCCGACTGATAA |
| T03 Beta2M target | 86 | TTAGCTGTGCTCGCGCTACTCTCTCTTTCTGGCCTGGAGGCTATCCA |
| T03 TALEN Beta2M LEFT | 87 | ATGGGCGATCCTAAAAAGAAACGTAAGGTCATCGATTACCCATACGATGTTCCAGATTACGCTATCGATA<br>TCGCCGATCTACGCACGCTCGGCTACAGCCAGCAGCAACAGGAGAAGATCAAACCGAAGGTTCGTTCGA<br>CAGTGGCGCAGCACCACGAGGCACTGGTCGGCCACGGGTTTACACACGCGCACATCGTTGCGTTAAGCC<br>AACACCCGGCAGCGTTAGGGACCGTCGCTGTCAAGTATCAGGACATGATCGCAGCGTTGCCAGAGGCGA<br>CACACGAAGCGATCGTTGGCGTCGGCAAACAGTGGTCCGGCGCACGCGCTCTGGAGGCCTTGCTCACGG<br>TGGCGGGAGAGTTGAGAGGTCCACCGTTACAGTTGGACACAGGCCAACTTCTCAAGATTGCAAAACGTG<br>GCGGCGTGACCGCAGTGGAGGCAGTGCATGCATGGCGCAATGCACTGACGGGTGCCCCGCTCAACTTGA<br>CCCCGGAGCAGGTGGTGGCCATCGCCAGCAATAATTGGTGGCAAGCAGGCGCTGGAGACGGTCCAGGCG<br>CTGTTGCCGGTGCTGTGCCAGGCCCACGGCTTGACCCCCCAGCAGGTGGTGGCCATCGCCAGCAATAATG<br>GTGGCAAGCAGGCGCTGGAGACGGTCCAGCGGCTGTTGCCGGTGCTGTGCCAGGCCCACGGCTTGACCC<br>CGGAGCAGGTGGTGGCCATCGCCAGCCACGATGGCGGCAAGCAGGCGCTGGAGACGGTCCAGCGGCTG<br>TTGCCGGTGCTGTGCCAGGCCCACGGCTTGACCCCCCAGCAGGTGGTGGCCATCGCCAGCAATGGCGGT<br>GGCAAGCAGGCGCTGGAGACGGTCCAGCGGCTGTTGCCGGTGCTGTGCCAGGCCCACGGCTTGACCCCC<br>CAGCAGGTGGTGGCCATCGCCAGCAATAATGGTGGCAAGCAGGCGCTGGAGACGGTCCAGCGGCTGTT<br>GCCGGTGCTGTGCCAGGCCCACGGCTTGACCCCCAGCAGGTGGTGGCCATCGCCAGCAATGGCGGTGG<br>CAAGCAGGCGCTGGAGACGGTCCAGCGGCTGTTGCCGGTGCTGTGCCAGGCCCACGGCTTGACCCCCCA<br>GCAGGTGGTGGCCATCGCCAGCAATAATGGTGGCAAGCAGGCGCTGGAGACGGTCCAGCGGCTGTTGC<br>CGGTGCTGTGCCAGGCCCACGGCTTGACCCCGGAGCAGGTGGTGGCCATCGCCAGCCACGATGGCGGCA<br>AGCAGGCGCTGGAGACGGTCCAGCGGCTGTTGCCGGTGCTGTGCCAGGCCCACGGCTTGACCCCCCAGC<br>AGGTGGTGGCCATCGCCAGCAATGGCGGTGGCAAGCAGGCGTCCAGCGGCTGTTGCCG<br>GTGCTGTGCCAGGCCCACGGCTTGACCCCGGAGCAGGTGGTGGCCATCGCCAGCCACGATGGCGGCAAG<br>CAGGCGCTGGAGACGGTCCAGCGGCTGTTGCCGGTGCTGTGCCAGGCCCACGGCTTGACCCCCAGCAG<br>GTGGTGGCCATCGCCAGCAATAATGGTGGCAAGCAGGCGCTGGAGACGGTCCAGCGGCTGTTGCCGGT<br>GCTGTGCCAGGCCCACGGCTTGACCCCGGAGCAGGTGGTGGCCATCGCCAGCCACGATGGCGGCAAGCA<br>GGCGCTGGAGACGGTCCAGCGGCTGTTGCCGGTGCTGTGCCAGGCCCACGGCTTGACCCCCCAGCAGGT |

TABLE 9-continued

Description of additional β2m TALE-nucleases sequences

| Target name | SEQ ID NO: | Half TALE-nuclease sequence |
|---|---|---|
| | | GGTGGCCATCGCCAGCAATAATGGTGGCAAGCAGGCGCTGGAGACGGTCCAGCGGCTGTTGCCGGTGCT<br>GTGCCAGGCCCACGGCTTGACCCCGGAGCAGGTGGTGGCCATCGCCAGCCACGATGGCGGCAAGCAGG<br>CGCTGGAGACGGTCCAGCGGCTGTTGCCGGTGCTGTGCCAGGCCCACGGCTTGACCCCCCAGCAGGTGG<br>TGGCCATCGCCAGCAATGGCGGTGGCAAGCAGGCGCTGGAGACGGTCCAGCGGCTGTTGCCGGTGCTGT<br>GCCAGGCCCACGGCTTGACCCCTCAGCAGGTGGTGGCCATCGCCAGCAATGGCGGCGGCAGGCCGGCGC<br>TGGAGAGCATTGTTGCCCAGTTATCTCGCCCTGATCCGGCGTTGGCCGCGTTGACCAACGACCACCTCGTC<br>GCCTTGGCCTGCCTCGGCGGGCGTCCTGCGCTGGATGCAGTGAAAAAGGGATTGGGGGATCCTATCAGC<br>CGTTCCCAGCTGGTGAAGTCCGAGCTGGAGGAGAAGAAATCCGAGTTGAGGCACAAGCTGAAGTACGTG<br>CCCCACGAGTACATCGAGCTGATCGAGATCGCCCGGAACAGCACCCAGGACCGTATCCTGGAGATGAAG<br>GTGATGGAGTTCTTCATGAAGGTGTACGGCTACAGGGGCAAGCACCTGGGCGGCTCCAGGAAGCCCGAC<br>GGCGCCATCTACACCGTGGGCTCCCCCATCGACTACGGCGTGATCGTGGACACCAAGGCCTACTCCGGCG<br>GCTACAACCTGCCCATCGGCCAGGCCGACGAAATGCAGAGGTACGTGGAGGAGAACCAGACCAGGAAC<br>AAGCACATCAACCCCAACGAGTGGTGGAAGGTGTACCCCTCCAGCGTGACCGAGTTCAAGTTCCTGTTCG<br>TGTCCGGCCACTTCAAGGGCAACTACAAGGCCCAGCTGACCAGGCTGAACCACATCACCAACTGCAACGG<br>CGCCGTGCTGTCCGTGGAGGAGCTCCTGATCGGCGGCGAGATGATCAAGGCCGGCACCCTGACCCTGGA<br>GGAGGTGAGGAGGAAGTTCAACAACGGCGAGATCAACTTCGCGGCCGACTGATAA |
| T03 TALEN Beta2M RIGHT | 88 | ATGGGCGATCCTAAAAAGAAACGTAAGGTCATCGATAAGGAGACCGCCGCTGCCAAGTTCGAGAGACAG<br>CACATGGACAGCATCGATATCGCCGATCTACGCACGCTCGGCTACAGCCAGCAGCAACAGGAGAAGATC<br>AAACCGAAGGTTCGTTCGACAGTGGCGCAGCACCACGAGGCACTGGTCGGCCACGGGTTTACACACGCG<br>CACATCGTTGCGTTAAGCCAACACCCGGCAGCGTTAGGGACCGTCGCTGTCAAGTATCAGGACATGATCG<br>CAGCGTTGCCAGAGGCGACACACGAAGCGATCGTTGGCGTCGGCAAACAGTGGTCCGGCGCACGCGCTC<br>TGGAGGCCTTGCTCACGGTGGCGGGAGAGTTGAGAGGTCCACCGTTACAGTTGGACACAGGCCAACTTC<br>TCAAGATTGCAAAACGTGGCGGCGTGACCGCAGTGGAGGCAGTGCATGCATGGCGCAATGCACTGACG<br>GGTGCCCCGCTCAACTTGACCCCCCAGCAGGTGGTGGCCATCGCCAGCAATAATGGTGGCAAGCAGGCG<br>CTGGAGACGGTCCAGCGGCTGTTGCCGGTGCTGTGCCAGGCCCACGGCTTGACCCCCCAGCAGGTGGTG<br>GCCATCGCCAGCAATAATGGTGGCAAGCAGGCGCTGGAGACGGTCCAGCGGCTGTTGCCGGTGCTGTGC<br>CAGGCCCACGGCTTGACCCCGGAGCAGGTGGTGGCCATCGCCAGCAATATTGGTGGCAAGCAGGCGCTG<br>GAGACGGTGCAGGCGCTGTTGCCGGTGCTGTGCCAGGCCCACGGCTTGACCCCCCAGCAGGTGGTGGCC<br>ATCGCCAGCAATGGCGGTGGCAAGCAGGCGCTGGAGACGGTCCAGCGGCTGTTGCCGGTGCTGTGCCA<br>GGCCCACGGCTTGACCCCGGAGCAGGTGGTGGCCATCGCCAGCAATATTGGTGGCAAGCAGGCGCTGGA<br>GACGGTGCAGGCGCTGTTGCCGGTGCTGTGCCAGGCCCACGGCTTGACCCCCAGCAGGTGGTGGCCAT<br>CGCCAGCAATAATGGTGGCAAGCAGGCGCTGGAGACGGTCCAGCGGCTGTTGCCGGTGCTGTGCCAGGC<br>CCACGGCTTGACCCCGGAGCAGGTGGTGGCCATCGCCAGCCACGATGGCGGCAAGCAGGCGCTGGAGA<br>CGGTCCAGCGGCTGTTGCCGGTGCTGTGCCAGGCCCACGGCTTGACCCCGGAGCAGGTGGTGGCCATCG<br>CCAGCCACGATGGCGGCAAGCAGGCGCTGGAGACGGTCCAGCGGCTGTTGCCGGTGCTGTGCCAGGCCC<br>ACGGCTTGACCCCCCAGCAGGTGGTGGCCATCGCCAGCAATGGCGGTGGCAAGCAGGCGCTGGAGACG<br>GTCCAGCGGCTGTTGCCGGTGCTGTGCCAGGCCCACGGCTTGACCCCGGAGCAGGTGGTGGCCATCGCC<br>AGCCACGATGGCGGCAAGCAGGCGCTGGAGACGGTCCAGCGGCTGTTGCCGGTGCTGTGCCAGGCCCA<br>CGGCTTGACCCCGGAGCAGGTGGTGGCCATCGCCAGCCACGATGGCGGCAAGCAGGCGCTGGAGACGG<br>TCCAGCGGCTGTTGCCGGTGCTGTGCCAGGCCCACGGCTTGACCCCGGAGCAGGTGGTGGCCATCGCCA<br>GCAATATTGGTGGCAAGCAGGCGCTGGAGACGGTGCAGGCGCTGTTGCCGGTGCTGTGCCAGGCCCAC<br>GGCTTGACCCCCAGCAGGTGGTGGCCATCGCCAGCAATAATGGTGGCAAGCAGGCGCTGGAGACGGTC<br>CAGCGGCTGTTGCCGGTGCTGTGCCAGGCCCACGGCTTGACCCCCAGCAGGTGGTGGCCATCGCCAGC<br>AATAATGGTGGCAAGCAGGCGCTGGAGACGGTCCAGCGGCTGTTGCCGGTGCTGTGCCAGGCCCACGGC<br>TTGACCCCGGAGCAGGTGGTGGCCATCGCCAGCCACGATGGCGGCAAGCAGGCGCTGGAGACGGTCCA<br>GCGGCTGTTGCCGGTGCTGTGCCAGGCCCACGCTTGACCCCTCAGCAGGTGGTGGCCATCGCCAGCAA<br>TGGCGGCGGCAGGCCGGCGCTGGAGAGCATTGTTGCCCAGTTATCTCGCCCTGATCCGGCGTTGGCCGC<br>GTTGACCAACGACCACCTCGTCGCCTTGGCCTGCCTCGGCGGGCGTCCTGCGCTGGATGCAGTGAAAAAG<br>GGATTGGGGGATCCTATCAGCCGTTCCCAGCTGGTGAAGTCCGAGCTGGAGGAGAAGAAATCCGAGTTG<br>AGGCACAAGCTGAAGTACGTGCCCCACGAGTACATCGAGCTGATCGAGATCGCCCGGAACAGCACCCAG<br>GACCGTATCCTGGAGATGAAGGTGATGGAGTTCTTCATGAAGGTGTACGGCTACAGGGGCAAGCACCTG<br>GGCGGCTCCAGGAAGCCCGACGGCGCCATCTACACCGTGGGCTCCCCCATCGACTACGGCGTGATCGTG<br>GACACCAAGGCCTACTCCGGCGGCTACAACCTGCCCATCGGCCAGGCCGACGAAATGCAGAGGTACGTG<br>GAGGAGAACCAGACCAGGAACAAGCACATCAACCCCAACGAGTGGTGGAAGGTGTACCCCTCCAGCGTG<br>ACCGAGTTCAAGTTCCTGTTCGTGTCCGGCCACTTCAAGGGCAACTACAAGGCCCAGCTGACCAGGCTGA<br>ACCACATCACCAACTGCAACGGCGCCGTGCTGTCCGTGGAGGAGCTCCTGATCGGCGGCGAGATGATCA<br>AGGCCGGCACCCTGACCCTGGAGGAGGTGAGGAGGAAGTTCAACAACGGCGAGATCAACTTCGCGGCC<br>GACTGATAA |

Figure 10:
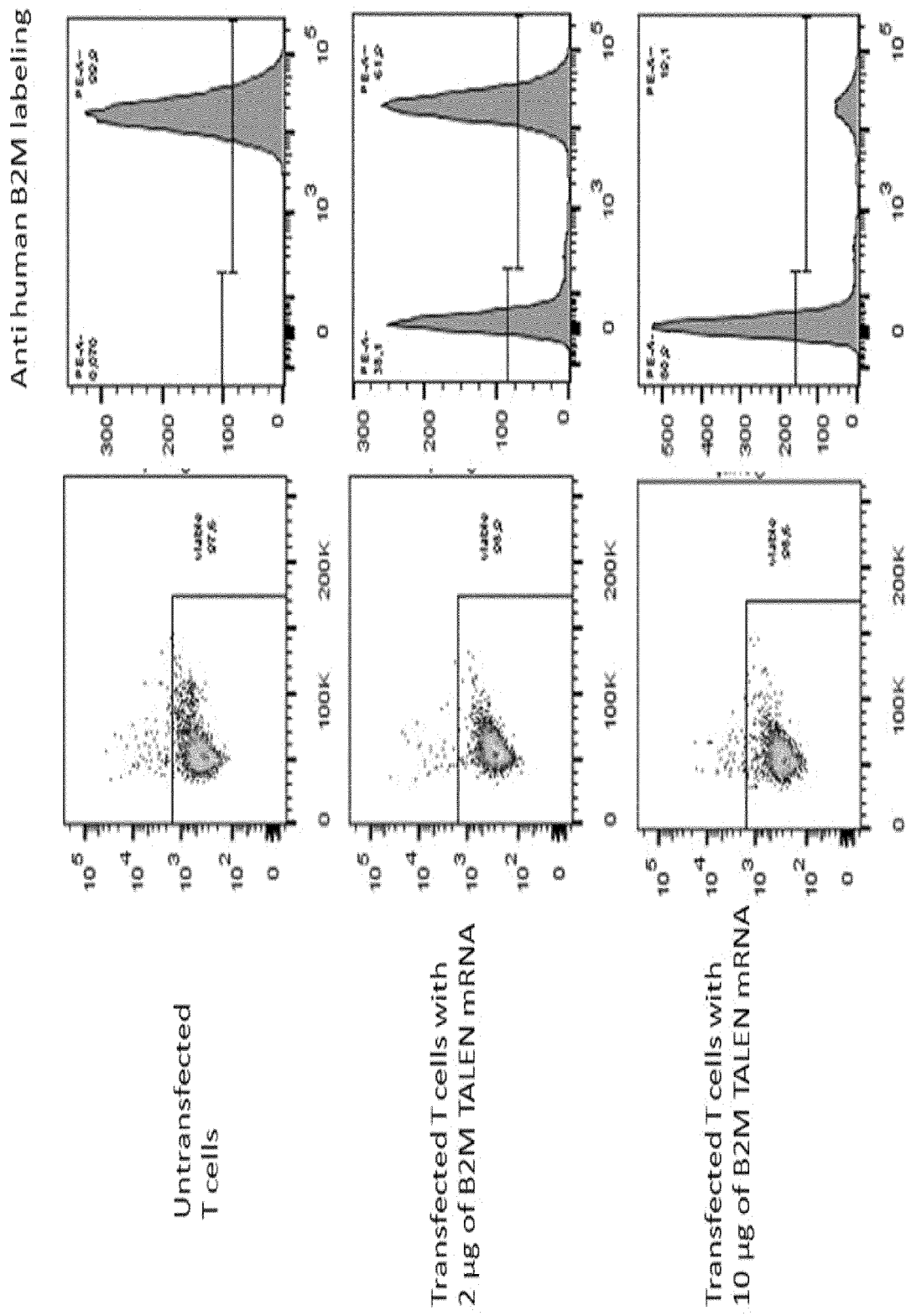
FIG. 10: FACS analysis of β2-m expression in T cells. Untransfected (top) and transfected T cells (middle and bottom) are analysed by FACS for viability (left) and β2-m expression (right).

To test the ability of this B2M specific TALEN to promote error-prone NHEJ events at the B2M locus, 2 or 10 μg of mRNA encoding TALEN were electroporated in Primary T cells using Pulse Agile technology according to the manufacturer protocol. Three days post transfection, cells were recovered and labeled with a specific β2-microglobulin antibody coupled to the PhycoErythrin fluorochrome. Cells are then analyzed by flow cytometry for viability and β2-m expression. The results are shown on FIG. 10. On the top panel, nearly 100% of untransfected T cells express β2-m (top right panel). Transfection of T cells with the specific B2M TALEN reduces dramatically β 2-m expression since 38% (middle right) and 80% of T cells (bottom right panel) become beta2-m negative when transfected with 2 μg or 10 μg of TALEN mRNA respectively. These data indicates that B2M knock-out in T cells can be achieved with high efficacy.

Production and Expression of the Single Chain Molecule B2M-UL18 in T Cells

HCMV UL18 encodes a type I transmembrane glycoprotein that shares a high level of AA sequence identity with MHC Class I molecules that associates with beta2-m and binds endogenous peptides. Since our goal is to express this molecule in T cells where B2M gene has been invalidated, our strategy is to produce a chimeric molecule where beta2-m and UL18 is fused as a single chain polypeptide. SEQ ID No 89 shows the amino-acid sequence of the chimeric protein. Lentiviral particles containing the chimeric B2M-UL18 are transduced into T cells. Expression of transgene is monitored by FACS analysis using a beta2-m antibody. The results from this experiment aim to show that a B2M-UL18 chimeric protein is efficiently expressed in T cells.

Production and Expression of NKG2D Ligands in T Cells

NKG2D natural ligands are transmembrane or GPI-anchored proteins. In order to achieve secretion of these molecules by T cells, the extra-cellular domains of NKG2D ligands have been fused in their N-terminus to a secretory peptide form. Amino-acid sequences of secreted chimeric NKG2D ligands are listed below (SEQ ID NO:90 to SEQ ID NO:97). Lentiviral particles containing the chimeric NKG2D ligands are transduced into T cells. Expression of transgene in culture supernatant is monitored by Western Blot analysis using specific antibodies. The results from this experiment aim to show that chimeric NKG2D ligand proteins are efficiently expressed in T cells.

Beta2-M Deficient CAR T Cells are not Recognized by Allogenic T Cells.

PBMCs from healthy donor A is co-cultured with irradiated or mitomycin-treated engineered beta2-m deficient T cells from donor B. As a control, PBMCs from healthy donor A is co-cultured with irradiated or mitomycin-treated engineered beta2-m positive T cells from donor B. 7 days later, cells proliferation from donor A is measured by XTT colorimetric assay or by CFSE dilution (FACS analysis). Although cell proliferation is observed in control, no or limited cell proliferation is observed when engineered T cells do not express beta2-m. The results from this experiment aim to show that alloreactive T cells are not able to recognize and proliferate against beta2-m deficient T cells.

Efficient Inhibition of NK Mediated Engineered T Cells Lysis

NK cells are purified from healthy donor A PBMCs. As targets, engineered T cells from healthy donor B are produced and listed below. a) engineered T cells (negative control), b) beta2-m deficient engineered T cells (positive control), c) beta2-m deficient engineered T cells expressing B2M-UL18 (SEQ ID No 89), d-k) beta2-m deficient engineered T cells expressing respectively SP-MICAed (SEQ ID No 90), SP-MICBed (SEQ ID No 91), SP-ULBP1ed (SEQ ID No 92), SP-ULBP2ed (SEQ ID No 93), SP-ULBP3ed (SEQ ID No 94), SP-N2DL4ed (SEQ ID No 95), SP-RET1Ged (SEQ ID No 96), SP-RAETILed (SEQ ID No 97). These sequences are reported in the following Table 10.

TABLE 10

Polypeptide sequence of a viral MHC homolog (UL18) and a panel of NKG2D ligands to be expressed according to the present invention.

| | SEQ ID NO: | Polypeptide sequence |
|---|---|---|
| Chimeric B2M-UL18 | 89 | MALPVTALLLPLALLLHAARPSRSVAL AVLALLSLSGLEAIQRTPKIQVYSRHP AENGKSNFLNCYVSGFHPSDIEVDLLK NGERIEKVEHSDLSFSKDWSFYLLYYT EFTPTEKDEYACRVNHVTLSQPKIVKW DRDMGGGGSGGGGSGGGGSGGGGSMTM WCLTLFVLWMLRVVGMHVLRYGYTGIF DDTSHMTLTVVGIFDGQHFFTYHVNSS DKASSRANGTISWMANVSAAYPTYLDG ERAKGDLIFNQTEQNLLELEIALGYRS QSVLTWTHECNTTENGSFVAGYEGFGW DGETLMELKDNLTLWTGPNYEISWLKQ NKTYIDGKIKNISEGDTTIQRNYLKGN CTQWSVIYSGFQTPVTHPVVKGGVRNQ NDNRAEAFCTSYGFFPGEINITFIHYG NKAPDDSEPQCNPLLPTFDGTFHQGCY VAIFCNQNYTCRVTHGNWTVEIPISVT SPDDSSSGEVPDHPTANKRYNTMTISS VLLALLLCALLFAFLHYFTTLKQYLRN LAFAWRYRKVRSS |
| SP-MICAed | 90 | MGGVLLTQRTLLSLVLALLFPSMASME PHSLRYNLTVLSWDGSVQSGFLTEVHL DGQPFLRCDRQKCRAKPQGQWAEDVLG NKTWDRETRDLTGNGKDLRMTLAHIKD QKEGLHSLQEIRVCEIHEDNSTRSSQH FYYDGELFLSQNLETKEWTMPQSSRAQ TLAMNVRNFLKEDAMKTKTHYHAMHAD CLQELRRYLKSGVVLRRTVPPMVNVTR SEASEGNITVTCRASGFYPWNITLSWR QDGVSLSHDTQQWGDVLPDGNGTYQTW VATRICQGEEQRFTCYMEHSGNHSTHP VPSGKVLVLQSHW |
| SP-MICBed | 91 | MGGVLLTQRTLLSLVLALLFPSMASMA EPHSLRYNLMVLSQDESVQSGFLAEGH LDGQPFLRYDRQKRRAKPQGQWAEDVL GAKTWDTETEDLTENGQDLRRTLTHIK DQKGGLHSLQEIRVCEIHEDSSTRGSR HFYYDGELFLSQNLETQESTVPQSSRA QTLAMNVTNFWKEDAMKTKTHYRAMQA DCLQKLQRYLKSGVAIRRTVPPMVNVT CSEVSEGNITVTCRASSFYPRNITLTW RQDGVSLSHNTQQWGDVLPDGNGTYQT WVATRIRQGEEQRFTCYMEHSGNHGTH PVPSGKVLVLQSQRTD |
| SP-ULBP1ed | 92 | MGGVLLTQRTLLSLVLALLFPSMASMG WVDTHCLCYDFIITPKSRPEPQWCEVQ GLVDERPFLHYDCVNHKAKAFASLGKK VNVTKTWEEQTETLRDVVDFLKGQLLD IQVENLIPIEPLTLQARMSCEHEAHGH GRGSWQFLFNGQKFLLFDSNNRKWTAL HPGAKKMTEKWEKNRDVTMFFQKISLG DCKMWLEEFLMYWEQMLDPT |
| SP-ULBP2ed | 93 | MGGVLLTQRTLLSLVLALLFPSMASMG RADPHSLCYDITVIPKFRPGPRWCAVQ GQVDEKTFLHYDCGNKTVTPVSPLGKK LNVTTAWKAQNPVLREVVDILTEQLRD IQLENYTPKEPLTLQARMSCEQKAEGH SSGSWQFSFDGQIELLFDSEKRMWTTV HPGARKMKEKWENDKVVAMSPHYFSMG DCIGWLEDFLMGMDSTLEPSAG |
| SP-ULBP3ed | 94 | MGGVLLTQRTLLSLVLALLFPSMASMD AHSLWYNFTIIHLPRHGQQWCEVQSQV DQKNFLSYDCGSDKVLSMGHLEEQLYA TDAWGKQLEMLREVGQRLRLELADTEL EDFTPSGPLTLQVRMSCECEADGYIRG SWQFSFDGRKFLLFDSNNRKWTVVHAG ARRMKEKWEKDSGLTTFFKMVSMRDCK SWLRDFLMHRKKRLEPT |
| SP-N2DL4ed | 95 | MGGVLLTQRTLLSLVLALLFPSMASMH SLCFNFTIKSLSRPGQPWCEAQVFLNK NLFLQYNSDNNMVKPLGLLGKKVYATS TWGELTQTLGEVGRDLRMLLCDIKPQI KTSDPSTLQVEMFCQREAERCTGASWQ |

TABLE 10-continued

Polypeptide sequence of a viral MHC homolog (UL18) and a panel of NKG2D ligands to be expressed according to the present invention.

| SEQ ID NO: | Polypeptide sequence |
|---|---|
| | FATNGEKSLLFDAMNMTWTVINHEASK IKETWKKDRGLEKYFRKLSKGDCDHWL REFLGHWEAMPEPTVSPVNASDIHWSS SSLPD |
| SP-RET1Ged 96 | MGGVLLTQRTLLSLVLALLFPSMASMG LADPHSLCYDITVIPKFRPGPRWCAVQ GQVDEKTFLHYDCGSKTVTPVSPLGKK LNVITAWKAQNPVLREVVDILTEQLLD IQLENYIPKEPLTLQARMSCEQKAEGH GSGSWQLSFDGQIFLLFDSENRMWTTV HPGARKMKEKWENDKDMTMSFHYISMG DCTGWLEDFLMGMDSTLEPSAGAPPTM SSGTAQPR |
| SP-RAETILed 97 | MGGVLLTQRTLLSLVLALLFPSMASMR RDDPHSLCYDITVIPKFRPGPRWCAVQ GQVDEKTFLHYDCGNKTVTPVSPLGKK LNVTMAWKAQNPVLREVVDILTEQLLD IQLENYTPKEPLTLQARMSCEQKAEGH SSGSWQFSIDGQTFLLFDSEKRMWTTV HPGARKMKEKWENDKDVAMSFHYISMG DCIGWLEDFLMGMDSTLEPSAG |

Cytotoxicity mediated by NK cells was determined by a CFSE labeling assay. Target cells were labeled with CFSE, washed in PBS, mixed with NK cells at various E:T cell ratios and incubated for 4 h at 37° C. Cells are then analysed by flow cytometry and percentages of CFSE positive engineered T cells are measured, indicating the survival of engineered T cells in the presence of NK cells. It is intended that although NK mediated cell lysis is observed in the positive control (beta2-m deficient engineered T cells), no or limited NK mediated cell lysis is observed when beta2-m deficient engineered T cells engineered T cells express B2M-UL18 (SEQ ID No 89) or secreted NKG2D ligands (SP-MICAed (SEQ ID No 90), SP-MICBed (SEQ ID No 91), SP-ULBP1ed (SEQ ID No 92), SP-ULBP2ed (SEQ ID No 93), SP-ULBP3ed (SEQ ID No 94), SP-N2DL4ed (SEQ ID No 95), SP-RET1Ged (SEQ ID No 96), SP-RAETILed (SEQ ID No 97). The results from this experiment aim to show that allogenic NK cells cytotoxicity activity is impaired when chimeric molecules, express in engineered T cells, act as decoy either for inhibitory signal receptor (B2M-UL18) or for stimulatory signal receptor (NKG2D ligands).

LIST OF REFERENCES CITED IN THE DESCRIPTION

Ashwell, J. D. and R. D. Klusner (1990). "Genetic and mutational analysis of the T-cell antigen receptor." *Annu Rev Immunol* 8: 139-67.

Betts, M. R., J. M. Brenchley, et al. (2003). "Sensitive and viable identification of antigen-specific CD8+ T cells by a flow cytometric assay for degranulation." *J Immunol Methods* 281(1-2): 65-78.

Bierer B. E. et al. (1993) "Cyclosporin A and FK506: molecular mechanisms of immunosuppression and probes for transplantation biology." *Curr Opin Immunol* 5(5): 763-73.

Bix M. et al (1991). "Rejection of class I MHC-deficient haemopoietic cells by irradiated MHC-matched mice." *Nature* 349(6307):329-31.

Boch, J., H. Scholze, et al. (2009). "Breaking the code of DNA binding specificity of TAL-type III effectors." *Science* 326(5959): 1509-12.

Cambier, J. C. (1995). "Antigen and Fc receptor signaling. The awesome power of the immunoreceptor tyrosine-based activation motif (ITAM)." *J Immunol* 155(7): 3281-5.

Carter L, et al. (2002). "PD-1:PD-L inhibitory pathway affects both CD4(+) and CD8(+) T cells and is overcome by IL-2". *Eur. J. Immunol.* 32 (3): 634-43.

Cong, L., F. A. Ran, et al. (2013). "Multiplex genome engineering using CRISPR/Cas systems." *Science* 339 (6121): 819-23.

Critchlow, S. E. and S. P. Jackson (1998). "DNA end-joining: from yeast to man." *Trends Biochem Sci* 23(10): 394-8.

Deltcheva, E., K. Chylinski, et al. (2011). "CRISPR RNA maturation by trans-encoded small RNA and host factor RNase III." *Nature* 471(7340): 602-7.

Gasiunas, G. et al. (2012). "Cas9-crRNA ribonucleoprotein complex mediates specific DNA cleavage for adaptive immunity in bacteria." *Proc Natl Acad Sci USA* 109(39): E2579-86.

Haseloff and Gerlach (1988). "Simple RNA enzymes with new and highly specific endoribonuclease activities." *Nature* 334: 585-591.

Jena, B., G. Dotti, et al. (2010). "Redirecting T-cell specificity by introducing a tumor-specific chimeric antigen receptor." *Blood* 116(7): 1035-44.

Jinek, M., K. Chylinski, et al. (2012). "A programmable dual-RNA-guided DNA endonuclease in adaptive bacterial immunity." *Science* 337(6096): 816-21.

Liu L et al. (1991). "Calcineurin is a common target of cyclophilin-cyclosporin A and FKBP-FK506 complexes." *Cell* 66(4): 807-15.

Ma, J. L, E. M. Kim, et al. (2003). "Yeast Mre11 and Rad1 proteins define a Ku-independent mechanism to repair double-strand breaks lacking overlapping end sequences." *Mol Cell Biol* 23(23): 8820-8.

Mach B., Steimle V, Reith W (1994). "MHC class II-deficient combined immunodeficiency: a disease of gene regulation". *Immunol. Rev.* 138 (1): 207-21.

Mali, P., L Yang, et al. (2013). "RNA-guided human genome engineering via Cas9." *Science* 339(6121): 823-6.

Moscou, M. J. and A. J. Bogdanove (2009). "A simple cipher governs DNA recognition by TAL effectors." *Science* 326(5959): 1501.

Park, T. S., S. A. Rosenberg, et al. (2011). "Treating cancer with genetically engineered T cells." *Trends Biotechnol* 29(11): 550-7.

Stoddard, B. L. (2005). "Homing endonuclease structure and function." *Q Rev Biophys* 38(1): 49-95.

Urnov F. D. et al. (2010) "Genome editing with engineered zinc finger nucleases" *Nature reviews Genetics* 11:636-646

The invention claimed is:

1. A therapeutic composition comprising engineered human T-cells expressing a Chimeric Antigen Receptor (CAR) that have lost surface expression of HLA-A, HLA-B, and HLA-C,
   wherein at least one gene encoding beta 2-microglobulin (B2M) is inactivated through expression in the T cells of a rare-cutting endonuclease able to selectively inactivate the gene encoding B2M,
   wherein said rare-cutting endonuclease inactivating the gene encoding B2M is a TALE-nuclease encoded by a polynucleotide having at least 90% identity with SEQ ID NO:81, SEQ ID NO:82, SEQ ID NO:84, SEQ ID NO:85, SEQ ID NO:87, or SEQ ID NO:88.

2. The therapeutic composition according to claim 1, wherein the gene encoding B2M is inactivated in the T cells by cleavage of the gene encoding B2M with a TALE-nuclease (TALEN) that cleaves a target site selected from SEQ ID NO:80, SEQ ID NO:83, and SEQ ID NO:86.

3. The therapeutic composition according to claim 2, wherein said TALEN is encoded by the polynucleotide sequences comprising SEQ ID NO:81 or SEQ ID NO:82.

4. The therapeutic composition according to claim 1, wherein said composition comprises at least 37% of engineered human T-cells that have lost surface expression of HLA-A, HLA-B, and HLA-C.

5. The therapeutic composition according to claim 1, wherein said Chimeric Antigen Receptor is directed against the B-lymphocyte antigen CD19.

6. The therapeutic composition according to claim 1, wherein said rare-cutting endonuclease inactivating the gene encoding B2M is a TALE-nuclease encoded by a polynucleotide having at least 90% identity with SEQ ID N0:81 or SEQ ID NO:82.

7. The therapeutic composition according to claim 1, wherein said rare-cutting endonuclease inactivating the gene encoding B2M is a TALE-nuclease encoded by a polynucleotide having at least 90% identity with SEQ ID N0:84 or SEQ ID NO:85.

8. The therapeutic composition according to claim 1, wherein said rare-cutting endonuclease inactivating the gene encoding B2M is a TALE-nuclease encoded by a polynucleotide having at least 90% identity with SEQ ID N0:87 or SEQ ID NO:88.

9. The therapeutic composition according to claim 1, wherein said gene encoding B2M is mutated within SEQ ID NO:80.

10. The therapeutic composition according to claim 1, wherein said gene encoding B2M is mutated within SEQ ID NO:83.

11. The therapeutic composition according to claim 1, wherein said gene encoding B2M is mutated within SEQ ID NO:86.

12. The therapeutic composition according to claim 1, wherein said T-cell further expresses at least one non-endogenous immune-suppressive polypeptide.

13. The therapeutic composition according to claim 12, wherein said at least one non-endogenous immune-suppressive polypeptide is selected from viral MHC homolog and NKG2D ligand.

14. The therapeutic composition according to claim 1, wherein said T-cell has a phenotype selected from [b2 m]$^-$[TCR]$^-$[CAR]$^+$, [b2 m]$^-$[TCR]$^-$ [viral MHC homolog]$^+$ [CAR]$^+$ and [b2 m]$^-$[TCR]$^-$[NKG2D ligand]$^+$[CAR]$^+$.

* * * * *